US008288385B2

(12) United States Patent
Caroff et al.

(10) Patent No.: US 8,288,385 B2
(45) Date of Patent: Oct. 16, 2012

(54) 6-(3-AZA-BICYCLO[3.1.0]HEX-3-YL)-2-PHENYL-PYRIMIDINES

(75) Inventors: Eva Caroff, Allschwil (CH); Kurt Hilpert, Allschwil (CH); Francis Hubler, Alschwil (CH); Emmanuel Meyer, Allschwil (CH); Dorte Renneberg, Allschwil (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 0 days.

(21) Appl. No.: 13/263,089

(22) PCT Filed: Apr. 7, 2010

(86) PCT No.: PCT/IB2010/051499
§ 371 (c)(1),
(2), (4) Date: Oct. 6, 2011

(87) PCT Pub. No.: WO2010/116328
PCT Pub. Date: Oct. 14, 2010

(65) Prior Publication Data
US 2012/0028989 A1    Feb. 2, 2012

(30) Foreign Application Priority Data
Apr. 8, 2009  (WO) ................ PCT/IB2009/051486

(51) Int. Cl.
*A61K 31/496*    (2006.01)
*C07D 403/14*    (2006.01)
(52) U.S. Cl. ................... 514/252.19; 544/295
(58) Field of Classification Search ........... 544/295; 514/252.19
See application file for complete search history.

(56) References Cited

U.S. PATENT DOCUMENTS
8,067,419 B2  11/2011  Binkert et al.

FOREIGN PATENT DOCUMENTS
| JP | 53073586 | 6/1978 |
|---|---|---|
| WO | WO 02/098856 | 12/2002 |
| WO | WO 2004/052366 | 6/2004 |
| WO | WO 2004/092189 | 10/2004 |
| WO | WO 2006/114774 | 11/2006 |
| WO | WO 2008/031556 | 3/2008 |
| WO | WO 2008/044217 | 4/2008 |
| WO | WO 2008/050301 | 5/2008 |
| WO | WO 2008/128647 | 10/2008 |
| WO | WO 2009/069100 | 6/2009 |
| WO | WO 2009/080226 | 7/2009 |
| WO | WO 2009/080227 | 7/2009 |
| WO | WO 2009/125365 | 10/2009 |
| WO | WO 2009/125366 | 10/2009 |
| WO | WO 2010/122504 | 10/2010 |

OTHER PUBLICATIONS

Brighty, K. E., et. al., "Synthesis of (1α, 5α, 6α)-6-Amino-3-azabicyclo[3.1.0]hexane, a Novel Achiral Diamine", SYNLETT, pp. 1097-1099, (Nov. 1996).
Gould, P. L., "Salt Selection for Basic Drugs", International Journal for Pharmaceutics, vol. 33, pp. 201-217, (1986).
Greene, T.W., et al., "Protective Groups in Organic Synthesis", Wiley-Interscience, (1999).
Parlow, J. J., et al., "Piperazinyl-glutamate-pyrimidines as Potent Orally Bioavailable P2Y$_{12}$ Antagonists for Inhibition of Platelet Aggregation", Bioorganic & Medicinal Chemistry Letters, vol. 19, pp. 4657-4663, (2009).
Parlow, J. J., et al., "Piperazinyl-glutamate-pyrimidines as Potent P2Y$_{12}$ Antagonists for Inhibition of Platelet Aggregation", Bioorganic & Medicinal Chemistry Letters, vol. 19, pp. 6148-6156, (2009).
Remington, The Science and Practice of Pharmacy, 21$^{st}$ Edition (2005), Part 5, "Pharmaceutical Manufacturing", [published by Lippincott Williams & Wilkins].
Caprie Steering Committee, "A randomized, blinded, trial of clopidogrel versus aspirin in patients at risk of ischaemic events (CAPRIE)", The Lancet, vol. 348, pp. 1329-1339, Nov. 16, 1996.
Parlow, John J. et al., "Piperazinyl-glutamate-pyrimidines as potent P2Y$_{12}$ antagonists for inhibition of platelet aggregation", 2009, Bioorganic & Medicinal Chemistry Letters, pp. 6148-6156.

*Primary Examiner* — Golam M M Shameem
*Assistant Examiner* — Karen Cheng
(74) *Attorney, Agent, or Firm* — Hoxie & Associates LLC

(57) ABSTRACT

The present invention relates to 6-(3-aza-bicyclo[3.1.0]hex-3-yl)-2-phenyl-pyrimidine derivatives and their use as P2Y$_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

16 Claims, No Drawings

6-(3-AZA-BICYCLO[3.1.0]HEX-3-YL)-2-PHENYL-PYRIMIDINES

CROSS REFERENCE TO RELATED APPLICATIONS

This application is a United States Application under 35 U.S.C. 371 claiming benefit of PCT Application No. PCT/IB2010/051499, filed on Apr. 7, 2010, which claims the benefit of PCT Application No. PCT/IB2009/051486, filed on Apr. 8, 2009, the contents of each of which are incorporated herein by reference in their entirety.

FIELD OF THE INVENTION

The present invention relates to certain 6-(3-aza-bicyclo[3.1.0]hex-3-yl)-2-phenyl-pyrimidine derivatives and their use as $P2Y_{12}$ receptor antagonists in the treatment and/or prevention of peripheral vascular, of visceral-, hepatic- and renal-vascular, of cardiovascular and of cerebrovascular diseases or conditions associated with platelet aggregation, including thrombosis in humans and other mammals.

BACKGROUND OF THE INVENTION

Haemostasis is referred to as the natural balance of maintaining the fluidity of the blood in the vascular system and preventing excessive blood loss subsequent to blood vessel injury by rapid formation of a solid blood clot. After vascular damage, contraction of the vessels and platelet adhesion occur immediately followed by aggregation of the platelets, activation of the coagulation cascade and finally also of the fibrinolytic system. Haemostatic abnormalities can lead to excessive bleeding or thrombosis, both life-threatening situations.

A series of antiplatelet agents have been developed over the past several years based on different mechanisms of action. The most widely used agent in antiplatelet therapy is aspirin, which irreversibly inhibits cyclooxygenase-1 and thereby affecting the thromboxane pathway. Although not optimally efficacious, treatment with aspirin remains the standard therapy against which new therapeutics are compared and judged.

Other drugs like the phosphodiesterase inhibitors dipyridamole and cilostazol, as well as the vitamin K antagonists (warfarin), are marketed but do not show all desirable features for such drugs. Three intravenously applicable, potent GPIIb/IIIa receptor antagonists (abciximab, eptifibatide, and tirofiban) blocking platelet aggregation are available on the market. Besides, some orally active GPIIb/IIIa antagonists (e.g. sibrafiban, xemilofiban or orbofiban) have not been successful in clinical development so far.

Adenosine 5'-diphosphate (ADP) is a key mediator in platelet activation and aggregation interfering with two platelet ADP receptors $P2Y_1$ and $P2Y_{12}$.

Antagonists of the platelet ADP receptor have been identified and display inhibition of platelet aggregation and antithrombotic activity. The most effective antagonists known so far are the thienopyridines ticlopidine, clopidogrel and CS-747, which have been used clinically as antithrombotic agents. It could be shown that these drugs, via their reactive metabolites, irreversibly block the ADP receptor subtype $P2Y_{12}$.

Some $P2Y_{12}$ antagonists like AR-C69931MX (Cangrelor) or AZD6140 have reached phase III clinical studies. These inhibitors are selective platelet ADP receptor antagonists, which inhibit ADP-dependent platelet aggregation, and are effective in vivo.

Piperazino-carbonylmethylaminocarbonyl-naphtyl or -quinolyl derivatives have been described as ADP receptor antagonists in WO 02/098856 and WO 2004/052366.

WO 2006/114774 describes 2-phenyl-4-(carbonylmethylaminocarbonyl)-pyrimidine derivatives as $P2Y_{12}$ receptor antagonists. However, unlike the invention compounds, the compounds disclosed in WO 2006/114774 do not have any 3-aza-bicyclo[3.1.0]hex-3-yl substitution on the pyrimidine core.

DESCRIPTION OF THE INVENTION

The inventors have now surprisingly found that the 6-(3-aza-bicyclo[3.1.0]hex-3-yl)-2-phenyl-pyrimidine derivatives of formula I described hereafter also show $P2Y_{12}$ receptor antagonist properties.

Various embodiments of the invention are presented hereafter:
1) The present invention firstly relates to the compounds of formula I

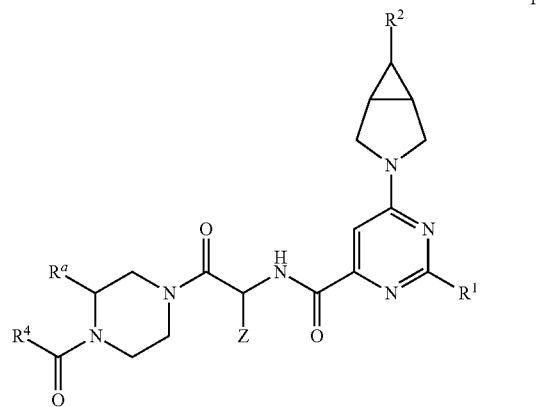

wherein
$R^1$ represents phenyl which is unsubstituted or mono-, di- or tri-substituted (preferably unsubstituted or mono- or di-substituted and more preferably unsubstituted or mono-substituted), wherein the substituents are independently selected from the group consisting of halogen, $(C_1-C_4)$alkyl and $(C_1-C_3)$fluoroalkyl;
Z represents hydrogen, $(C_1-C_4)$alkyl, cyclopropyl, cyclopropylmethyl, hydroxy-$(C_1-C_3)$alkyl, carboxy-$(C_1-C_3)$alkyl, cyano-$(C_1-C_3)$alkyl, $P(O)(R^6)_2$—$(C_1-C_3)$alkyl, 1H-tetrazol-5-yl-$(C_1-C_3)$alkyl or benzyl;
$R^2$ represents cyano, —COOH, —CONH$_2$, —COOR$^3$, hydroxy-$(C_1-C_3)$alkyl, $(C_1-C_2)$alkoxy-$(C_1-C_2)$alkyl, carboxy-$(C_1-C_3)$alkyl, 1H-tetrazol-5-yl or —NHR$^5$;
with the proviso that, if $R^2$ represents —COOR$^3$, Z represents carboxy-$(C_1-C_3)$alkyl or $P(O)(R^6)_2$—$(C_1-C_3)$alkyl;
$R^a$ represents hydrogen or methyl;
$R^3$ represents $(C_1-C_4)$alkyl;
$R^4$ represents $(C_1-C_6)$alkoxy or benzyloxy;
$R^5$ represents hydrogen or tert-butoxycarbonyl;
$R^6$ represents hydroxy, $(C_1-C_4)$alkoxy, $R^7$—OCH$_2$O— or $R^8$—$(C_1-C_4)$alkyl-NH—;
$R^7$ represents $(C_1-C_4)$alkylcarbonyl or $(C_1-C_4)$alkoxycarbonyl; and
$R^8$ represents $(C_1-C_4)$alkoxycarbonyl;
and to the salts (in particular pharmaceutically acceptable salts) of such compounds.

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art.

The compounds of formula I are $P2Y_{12}$ receptor antagonists. Accordingly, they are useful in therapy (including combination therapy), where they can be widely used as inhibitors of platelet activation, aggregation and degranulation, as promoters of platelet disaggregation or as anti-thrombotic agents.

The following paragraphs provide definitions of the various chemical moieties for the compounds according to the invention. Said definitions are intended to apply uniformly throughout the specification and claims unless an otherwise expressly set out definition provides a broader or narrower definition.

The term "halogen" refers to fluorine, chlorine, bromine or iodine, preferably to fluorine or chlorine and more preferably to fluorine.

The term "alkyl", used alone or in combination, refers to a straight or branched chain alkyl group containing one to four carbon atoms. The term "$(C_x\text{-}C_y)$alkyl" (x and y each being an integer), refers to an alkyl group as defined before containing x to y carbon atoms. For example a $(C_1\text{-}C_4)$alkyl group contains from one to four carbon atoms. Representative examples of alkyl groups include methyl, ethyl, n-propyl, iso-propyl, n-butyl, iso-butyl, sec-butyl and tert-butyl.

In case $(C_1\text{-}C_4)$alkyl is substituent for $R^1$ the term preferably refers to methyl and ethyl, and most preferably to methyl.

In case "Z" represents $(C_1\text{-}C_4)$alkyl the term preferably refers to methyl, ethyl, n-propyl, iso-propyl, n-butyl, iso-butyl and tert-butyl, more preferably to methyl, ethyl and iso-propyl, and most preferably to iso-propyl.

In case "$R^3$" represents $(C_1\text{-}C_4)$alkyl the term preferably refers to methyl and ethyl, and most preferably to ethyl.

The term "fluoroalkyl" refers to an alkyl group as defined before containing one to three carbon atoms in which one or more (and possibly all) hydrogen atoms have been replaced with fluorine. The term "$(C_x\text{-}C_y)$fluoroalkyl" (x and y each being an integer) refers to a fluoroalkyl group as defined before containing x to y carbon atoms. For example a $(C_1\text{-}C_3)$fluoroalkyl group contains from one to three carbon atoms in which one to seven hydrogen atoms have been replaced with fluorine. Representative examples of fluoroalkyl groups include trifluoromethyl and 2,2,2-trifluoroethyl. Preferred are $(C_1)$fluoroalkyl groups such as trifluoromethyl and most preferred is trifluoromethyl.

The term "hydroxy-$(C_x\text{-}C_y)$alkyl" (x and y each being an integer) refers to an alkyl group as defined before containing x to y carbon atoms wherein one hydrogen atom has been replaced by hydroxy. For example a hydroxy-$(C_1\text{-}C_3)$alkyl group refers to an alkyl group as defined before containing 1 to 3 carbon atoms wherein one hydrogen atom has been replaced by hydroxy. Representative examples of hydroxy-$(C_x\text{-}C_y)$alkyl groups include hydroxy-methyl, 1-hydroxy-ethyl, 2-hydroxy-ethyl, 1-hydroxy-propyl, 2-hydroxy-propyl, 3-hydroxy-propyl and 1-hydroxy-1-methyl-ethyl.

In case "Z" represents hydroxy-$(C_1\text{-}C_3)$alkyl the term preferably refers to 1-hydroxy-ethyl.

In case "$R^2$" represents hydroxy-$(C_1\text{-}C_3)$alkyl the term preferably refers to hydroxy-methyl.

The term "carboxy-$(C_x\text{-}C_y)$alkyl" (x and y each being an integer) refers to an alkyl group as defined before containing x to y carbon atoms wherein one hydrogen atom has been replaced by —COOH. For example a carboxy-$(C_1\text{-}C_3)$alkyl group refers to an alkyl group as defined before containing 1 to 3 carbon atoms wherein one hydrogen atom has been replaced by —COOH. Representative examples of carboxy-$(C_x\text{-}C_y)$alkyl groups include carboxy-methyl, 1-carboxy-ethyl, 2-carboxy-ethyl, 1-carboxy-propyl, 2-carboxy-propyl, 3-carboxy-propyl and 1-carboxy-1-methyl-ethyl.

In case "Z" represents carboxy-$(C_1\text{-}C_3)$alkyl the term preferably refers to carboxy-methyl and 2-carboxy-ethyl and most preferably to 2-carboxy-ethyl.

In case "$R^2$" represents carboxy-$(C_1\text{-}C_3)$alkyl the term preferably refers to carboxy-methyl and 2-carboxy-ethyl and most preferably to carboxy-methyl.

The term "cyano-$(C_x\text{-}C_y)$alkyl" (x and y each being an integer) refers to an alkyl group as defined before containing x to y carbon atoms wherein one hydrogen atom has been replaced by cyano. For example a cyano-$(C_1\text{-}C_3)$alkyl group refers to an alkyl group as defined before containing 1 to 3 carbon atoms wherein one hydrogen atom has been replaced by cyano. Representative examples of cyano-$(C_x\text{-}C_y)$alkyl groups include cyano-methyl, 1-cyano-ethyl, 2-cyano-ethyl, 1-cyano-propyl, 2-cyano-propyl, 3-cyano-propyl and 1-cyano-1-methyl-ethyl. Preferred are cyano-methyl and 2-cyano-ethyl and most preferred is cyano-methyl.

The term "$P(O)(R^6)_2$—$(C_x\text{-}C_y)$alkyl" (x and y each being an integer) refers to an alkyl group as defined before containing x to y carbon atoms wherein one hydrogen atom has been replaced by a $(R^6)_2(O)P$— group which group is attached to the alkyl group via the phosphor atom. For example a $P(O)(R^6)_2$—$(C_1\text{-}C_3)$alkyl group refers to an alkyl group as defined before containing 1 to 3 carbon atoms wherein one hydrogen atom has been replaced by a $(R^6)_2(O)P$— group. Representative examples of $P(O)(R^6)_2$—$(C_x\text{-}C_y)$alkyl groups include $P(O)(R^6)_2$-methyl, 1-[$P(O)(R^6)_2$]-ethyl, 2-[$P(O)(R^6)_2$]-ethyl, 1-[$P(O)(R^6)_2$]-propyl, 2-[$P(O)(R^6)_2$]-propyl, 3-[$P(O)(R^6)_2$]-propyl and 1-[$P(O)(R^6)_2$]-1-methyl-ethyl. Preferred are $P(O)(R^6)_2$-methyl and 2-[$P(O)(R^6)_2$]-ethyl and most preferred is $P(O)(R^6)_2$-methyl.

The term "1H-tetrazol-5-yl-$(C_x\text{-}C_y)$alkyl" (x and y each being an integer) refers to an alkyl group as defined before containing x to y carbon atoms wherein one hydrogen atom has been replaced by 1H-tetrazol-5-yl. For example a 1H-tetrazol-5-yl-$(C_1\text{-}C_3)$alkyl group refers to an alkyl group as defined before containing 1 to 3 carbon atoms wherein one hydrogen atom has been replaced by 1H-tetrazol-5-yl. Representative examples of 1H-tetrazol-5-yl-$(C_x\text{-}C_y)$alkyl groups include 1H-tetrazol-5-yl-methyl, 1-(1H-tetrazol-5-yl)-ethyl, 2-(1H-tetrazol-5-yl)-ethyl, 1-(1H-tetrazol-5-yl)-propyl, 2-(1H-tetrazol-5-yl)-propyl, 3-(1H-tetrazol-5-yl)-propyl and 1-methyl-1-(1H-tetrazol-5-yl)-ethyl. Preferred are 1H-tetrazol-5-yl-methyl and 2-(1H-tetrazol-5-yl)-ethyl, and most preferred is 2-(1H-tetrazol-5-yl)-ethyl.

The term "$R^8$—$(C_x\text{-}C_y)$alkyl-NH—" (x and y each being an integer) refers to an amino group wherein one hydrogen atom has been replaced by an alkyl group as defined before containing x to y carbon atoms, wherein the alkyl group is substituted with $R^8$. For example a $R^8$—$(C_1\text{-}C_4)$alkyl-NH— group refers to an amino group wherein one hydrogen atom has been replaced by an alkyl group as defined before containing 1 to 4 carbon atoms, wherein the alkyl group is substituted with $R^8$. Preferably the substituent $R^8$ and the nitrogen atom of the amino group are attached to the same carbon atom of the alkyl group. Examples of $R^8$—$(C_x\text{-}C_y)$alkyl-NH— groups include, but are not limited to, 1-alkoxycarbonyl-ethylamino and notably 1-ethoxycarbonyl-ethylamino.

The term "$(C_x\text{-}C_y)$alkylcarbonyl (x and y each being an integer) refers to a group of the formula $(C_x\text{-}C_y)$alkyl-C(O)— wherein the $(C_x-C_y)$alkyl group is an alkyl group as defined before containing x to y carbon atoms. For example a $(C_1-C_4)$alkylcarbonyl group refers to a group of the formula $(C_1-C_4)$alkyl-C(O)— wherein the $(C_1-C_4)$alkyl group is an alkyl group as defined before containing 1 to 4 carbon atoms. Representative examples of $(C_x-C_y)$alkylcarbonyl groups include methylcarbonyl(acetyl) and ethylcarbonyl. Preferred is acetyl.

The term "alkoxy", used alone or in combination, refers to a straight or branched chain alkoxy group containing one to six carbon atoms. The term "$(C_x-C_y)$alkoxy" (x and y each being an integer), refers to an alkoxy group as defined before containing x to y carbon atoms. For example a $(C_1-C_6)$alkoxy group contains from one to six carbon atoms. Representative examples of alkoxy groups include methoxy, ethoxy, n-propoxy, iso-propoxy, n-butoxy, iso-butoxy, sec-butoxy, tert-butoxy, n-pentoxy, neopentyloxy, iso-pentyloxy, n-hexyloxy and iso-hexyloxy.

In case "$R^4$" represents $(C_1-C_6)$alkoxy the term preferably refers to ethoxy, n-propoxy, n-butoxy, n-pentoxy and n-hexyloxy, and most preferably to n-butoxy.

In case "$R^6$" represents $(C_1-C_4)$alkoxy the term preferably refers to methoxy, ethoxy and n-propoxy, and most preferably to ethoxy.

The term "$(C_x-C_y)$alkoxy-$(C_x-C_y)$alkyl" (x, x', y and y' each being an integer) refers to an alkyl group as defined before containing x to y carbon atoms wherein one hydrogen atom has been replaced by $(C_x-C_y)$alkoxy as defined before containing x' to y' carbon atoms. For example a "$(C_1-C_2)$alkoxy-$(C_1-C_2)$alkyl" group refers to an alkyl group as defined before containing 1 to 2 carbon atoms wherein one hydrogen atom has been replaced by an alkoxy group as defined before containing 1 to 2 carbon atoms. Representative examples of $(C_x-C_y)$alkoxy-$(C_x-C_y)$alkyl groups include methoxy-methyl, ethoxy-methyl, 1-methoxy-ethyl, 2-methoxy-ethyl, 1-ethoxy-ethyl and 2-ethoxy-ethyl. Preferred is methoxy-methyl.

The term "$(C_x-C_y)$alkoxycarbonyl" (x and y each being an integer) refers to a group of the formula $(C_x-C_y)$alkoxy-C(O)— wherein the $(C_x-C_y)$alkoxy group is an alkoxy group as defined before containing x to y carbon atoms. For example a "$(C_1-C_4)$alkoxycarbonyl" group refers to a group of the formula $(C_1-C_4)$alkoxy-C(O)— wherein the $(C_1-C_4)$alkoxy group is an alkoxy group as defined before containing 1 to 4 carbon atoms. Representative examples of $(C_x-C_y)$alkoxycarbonyl groups include methoxycarbonyl, ethoxycarbonyl, n-propoxycarbonyl, iso-propoxycarbonyl, n-butoxycarbonyl, iso-butoxycarbonyl, sec-butoxycarbonyl and tert-butoxycarbonyl.

In case "$R^7$" represents $(C_1-C_4)$alkoxycarbonyl the term preferably refers to methoxycarbonyl and ethoxycarbonyl, and most preferably to ethoxycarbonyl.

In case "$R^8$" represents $(C_1-C_4)$alkoxycarbonyl the term preferably refers to methoxycarbonyl and ethoxycarbonyl, and most preferably to ethoxycarbonyl.

The term "$(C_x-C_y)$alkoxycarbonyl-$(C_x-C_y)$alkyl" (x, x', y and y' each being an integer) refers to an alkyl group as defined before containing x to y carbon atoms wherein one hydrogen atom has been replaced by an $(C_x-C_y)$alkoxycarbonyl-group as defined before containing x' to y' carbon atoms. For example a "$(C_1-C_4)$alkoxycarbonyl-$(C_1-C_3)$alkyl" group refers to an alkyl group as defined before containing 1 to 3 carbon atoms wherein one hydrogen atom has been replaced by an alkoxycarbonyl group as defined before containing 1 to 4 carbon atoms. Representative examples of $(C_x-C_y)$alkoxycarbonyl-$(C_x-C_y)$alkyl groups include $(C_x-C_y)$alkoxycarbonyl-methyl, 2-$(C_x-C_y)$alkoxycarbonyl-ethyl and 3-$(C_x-C_y)$alkoxycarbonyl-propyl, wherein the $(C_x-C_y)$alkoxycarbonyl group represents for example methoxycarbonyl, ethoxycarbonyl, n-propoxycarbonyl, iso-propoxycarbonyl, n-butoxycarbonyl, iso-butoxycarbonyl, sec-butoxycarbonyl and tert-butoxycarbonyl.

Besides, the following paragraphs provide definitions of various other terms. Said definitions are intended to apply uniformly throughout the specification and claims unless an otherwise expressly set out definition provides a broader or narrower definition.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

The term "room temperature" as used herein refers to a temperature of 25° C.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" (or alternatively the term "around") placed before a temperature "Y" refers in the current application to an interval extending from the temperature Y minus 10° C. to Y plus 10° C., and preferably to an interval extending from Y minus 5° C. to Y plus 5° C.

2) A further embodiment of the invention relates to compounds of formula I according to embodiment 1), wherein
$R^1$ represents phenyl which is unsubstituted or mono-substituted with halogen (especially fluorine), $(C_1-C_2)$alkyl (especially methyl) or $(C_1)$fluoroalkyl (especially trifluoromethyl);
Z represents hydrogen, $(C_1-C_4)$alkyl, cyclopropyl, cyclopropylmethyl, hydroxy-$(C_1-C_2)$alkyl (especially 1-hydroxy-ethyl), carboxy-$(C_1-C_2)$alkyl (especially 2-carboxy-ethyl), cyano-$(C_1-C_2)$alkyl (especially cyano-methyl), $P(O)(R^6)_2$—$(C_1-C_2)$alkyl (especially $P(O)(R^6)_2$-methyl), 1H-tetrazol-5-yl-$(C_1-C_2)$alkyl (especially 2-(1H-tetrazol-5-yl)-ethyl) or benzyl;
$R^2$ represents cyano, —COOH, —CONH$_2$, —COOR$^3$, hydroxy-$(C_1-C_2)$alkyl (especially hydroxy-methyl), methoxy-methyl, carboxy-$(C_1-C_2)$alkyl (especially carboxy-methyl or 2-carboxy-ethyl), 1H-tetrazol-5-yl or —NHR$^5$;
with the proviso that, if $R^2$ represents —COOR$^3$, Z represents carboxy-$(C_1-C_2)$alkyl or $P(O)(R^6)_2$—$(C_1-C_2)$alkyl;
$R^a$ represents hydrogen or methyl;
$R^3$ represents $(C_1-C_2)$alkyl (especially ethyl);
$R^4$ represents $(C_1-C_6)$alkoxy or benzyloxy;
$R^5$ represents hydrogen or tert-butoxycarbonyl;
$R^6$ represents hydroxy, $R^7$—OCH$_2$O— or $R^8$—$(C_1-C_4)$alkyl-NH— (especially hydroxy or $R^7$—OCH$_2$O—);
$R^7$ represents $(C_1-C_2)$alkylcarbonyl (especially acetyl) or $(C_1-C_2)$alkoxycarbonyl (especially ethoxycarbonyl);
$R^8$ represents $(C_1-C_2)$alkoxycarbonyl (especially ethoxycarbonyl);
and to the salts (in particular pharmaceutically acceptable salts) of such compounds.

3) A further embodiment of the invention relates to compounds of formula I according to embodiment 1) or 2), wherein
$R^1$ represents phenyl which is unsubstituted or mono-substituted with fluorine, methyl or trifluoromethyl;
Z represents hydrogen, $(C_1-C_4)$alkyl (especially iso-propyl), cyclopropyl, 1-hydroxy-ethyl, 2-carboxy-ethyl, cyano-methyl, or 2-(1H-tetrazol-5-yl)-ethyl;
$R^2$ represents cyano, —COOH, —CONH$_2$, hydroxy-methyl, methoxy-methyl, carboxy-methyl, 2-carboxy-ethyl, 1H-tetrazol-5-yl or —NHR$^5$;

$R^a$ represents hydrogen;
$R^4$ represents $(C_1-C_6)$alkoxy; and
$R^5$ represents hydrogen or tert-butoxycarbonyl;
and to the salts (in particular pharmaceutically acceptable salts) of such compounds.

4) A further embodiment of the invention relates to compounds of formula I according to embodiment 1) or 2), wherein
$R^1$ represents phenyl which is unsubstituted or mono-substituted with halogen, $(C_1-C_2)$alkyl or trifluoromethyl;
and to the salts (in particular pharmaceutically acceptable salts) of such compounds.

5) A further embodiment of the invention relates to compounds of formula I according to any one of embodiments 1) to 4), wherein
$R^1$ represents phenyl which is unsubstituted or mono-substituted with fluorine, methyl or trifluoromethyl;
and to the salts (in particular pharmaceutically acceptable salts) of such compounds.

6) A further embodiment of the invention relates to compounds of formula I according to embodiment 1), 2), 4) or 5), wherein
Z represents hydrogen, $(C_1-C_4)$alkyl, cyclopropyl, cyclopropylmethyl, hydroxy-$(C_1-C_2)$alkyl (especially 1-hydroxy-ethyl), carboxy-$(C_1-C_2)$alkyl (especially 2-carboxy-ethyl), cyano-$(C_1-C_2)$alkyl (especially cyano-methyl), $P(O)(R^6)_2$—$(C_1-C_2)$alkyl (especially $P(O)(R^6)_2$-methyl), 1H-tetrazol-5-yl-$(C_1-C_2)$alkyl (especially 2-(1H-tetrazol-5-yl)-ethyl) or benzyl; and to the salts (in particular pharmaceutically acceptable salts) of such compounds.

7) A further embodiment of the invention relates to compounds of formula I according to any one of embodiments 1), 2) or 4) to 6), wherein
Z represents hydrogen, $(C_1-C_4)$alkyl (especially iso-propyl), cyclopropyl, 1-hydroxy-ethyl, 2-carboxy-ethyl, cyano-methyl, $P(O)(R^6)_2$-methyl (especially phosphono-methyl or [bis-acetoxymethoxy-phosphoryl]-methyl) or 2-(1H-tetrazol-5-yl)-ethyl;
and to the salts (in particular pharmaceutically acceptable salts) of such compounds.

8) A further embodiment of the invention relates to compounds of formula I according to any one of embodiments 1) to 7), wherein
Z represents iso-propyl, cyclopropyl, 1-hydroxy-ethyl, 2-carboxy-ethyl, or 2-(1H-tetrazol-5-yl)-ethyl;
and to the salts (in particular pharmaceutically acceptable salts) of such compounds.

9) A further embodiment of the invention relates to compounds of formula I according to any one of embodiments 1) to 8), wherein
Z represents iso-propyl, cyclopropyl, 1-hydroxy-ethyl, or 2-(1H-tetrazol-5-yl)-ethyl;
and to the salts (in particular pharmaceutically acceptable salts) of such compounds.

10) A further embodiment of the invention relates to compounds of formula I according to any one of embodiments 1) to 9), wherein
Z represents iso-propyl;
and to the salts (in particular pharmaceutically acceptable salts) of such compounds.

11) A further embodiment of the invention relates to compounds of formula I according to any one of embodiments 1) to 9), wherein
Z represents 2-(1H-tetrazol-5-yl)-ethyl;
and to the salts (in particular pharmaceutically acceptable salts) of such compounds.

12) A further embodiment of the invention relates to compounds of formula I according to any one of embodiments 1) to 8), wherein
Z represents 2-carboxy-ethyl;
and to the salts (in particular pharmaceutically acceptable salts) of such compounds.

13) A further embodiment of the invention relates to compounds of formula I according to any one of embodiments 1), 2) or 4 to 6), wherein
Z represents $P(O)(R^6)_2$—$(C_1-C_2)$alkyl (especially $P(O)(R^6)_2$-methyl);
and to the salts (in particular pharmaceutically acceptable salts) of such compounds.

14) A further embodiment of the invention relates to compounds of formula I according to any one of embodiments 1), 2) or 4 to 7), wherein
Z represents $P(O)(R^6)_2$-methyl (especially phosphono-methyl or [bis-acetoxymethoxy-phosphoryl]-methyl);
and to the salts (in particular pharmaceutically acceptable salts) of such compounds.

15) A further embodiment of the invention relates to compounds of formula I according to any one of embodiments 1) to 14), wherein
$R^2$ represents cyano, —COOH, —$CONH_2$, hydroxy-methyl, methoxy-methyl, carboxy-methyl, 2-carboxy-ethyl, 1H-tetrazol-5-yl or —$NHR^5$;
and to the salts (in particular pharmaceutically acceptable salts) of such compounds.

16) A further embodiment of the invention relates to compounds of formula I according to any one of embodiments 1) to 15), wherein
$R^2$ represents cyano, —COOH, —$CONH_2$, carboxy-methyl, 1H-tetrazol-5-yl or —$NHR^5$;
and to the salts (in particular pharmaceutically acceptable salts) of such compounds.

17) A further embodiment of the invention relates to compounds of formula I according to any one of embodiments 1) to 15), wherein
$R^2$ represents hydroxy-methyl or methoxy-methyl;
and to the salts (in particular pharmaceutically acceptable salts) of such compounds.

18) A further embodiment of the invention relates to compounds of formula I according to any one of embodiments 1) to 17), wherein
$R^a$ represents hydrogen;
and to the salts (in particular pharmaceutically acceptable salts) of such compounds.

19) A further embodiment of the invention relates to compounds of formula I according to any one of embodiments 1), 2) or 4) to 17), wherein
$R^a$ represents methyl;
and to the salts (in particular pharmaceutically acceptable salts) of such compounds.

20) A further embodiment of the invention relates to compounds of formula I according to any one of embodiments 1) to 19), wherein
$R^4$ represents $(C_1-C_6)$alkoxy;
and to the salts (in particular pharmaceutically acceptable salts) of such compounds.

21) A further embodiment of the invention relates to compounds of formula I according to any one of embodiments 1) to 20), wherein
$R^4$ represents ethoxy, n-propoxy, n-butoxy, n-pentoxy or n-hexyloxy;
and to the salts (in particular pharmaceutically acceptable salts) of such compounds.

22) A further embodiment of the invention relates to compounds of formula I according to any one of embodiments 1) to 21), wherein $R^4$ represents n-butoxy;

and to the salts (in particular pharmaceutically acceptable salts) of such compounds.

23) A further embodiment of the invention relates to compounds of formula I according to any one of embodiments 1) to 22), wherein $R^5$ represents hydrogen;

and to the salts (in particular pharmaceutically acceptable salts) of such compounds.

24) A further embodiment of the invention relates to compounds of formula I according to any one of embodiments 1), 2), 4) to 7) or 13) to 23), wherein $R^6$ represents hydroxy, $R^7$—OCH$_2$O— or $R^8$—(C$_1$-C$_4$)alkyl-NH— (especially hydroxy or $R^7$—OCH$_2$O—);

and to the salts (in particular pharmaceutically acceptable salts) of such compounds.

25) A further embodiment of the invention relates to compounds of formula I according to any one of embodiments 1), 2), 4) to 7) or 13) to 24), wherein $R^6$ represents hydroxy;

and to the salts (in particular pharmaceutically acceptable salts) of such compounds.

26) A further embodiment of the invention relates to compounds of formula I according to any one of embodiments 1), 2), 4) to 7) or 13) to 24), wherein $R^6$ represents $R^7$—OCH$_2$O— or $R^8$—(C$_1$-C$_4$)alkyl-NH— (especially $R^7$—OCH$_2$O—);

and to the salts (in particular pharmaceutically acceptable salts) of such compounds.

27) A further embodiment of the invention relates to compounds of formula I according to any one of embodiments 1), 2), 4) to 7), 13) to 24) or 26), wherein $R^7$ represents (C$_1$-C$_2$)alkylcarbonyl (especially acetyl) or (C$_1$-C$_2$)alkoxycarbonyl (especially ethoxycarbonyl);

and to the salts (in particular pharmaceutically acceptable salts) of such compounds.

28) A further embodiment of the invention relates to compounds of formula I according to any one of embodiments 1), 2), 4) to 7), 13) to 24) or 26), wherein $R^7$ represents acetyl;

and to the salts (in particular pharmaceutically acceptable salts) of such compounds.

29) A further embodiment of the invention relates to compounds of formula I according to any one of embodiments 1), 2), 4) to 7), 13) to 24) or 26), wherein $R^8$ represents (C$_1$-C$_2$)alkoxycarbonyl (especially ethoxycarbonyl);

and to the salts (in particular pharmaceutically acceptable salts) of such compounds.

30) A preferred embodiment of the invention relates to compounds of formula I according to any one of embodiments 1) to 29), wherein, in case "Z" is different from hydrogen, the stereogenic center of the amino acid moiety has a configuration as depicted in formula $I_{ST}$ below

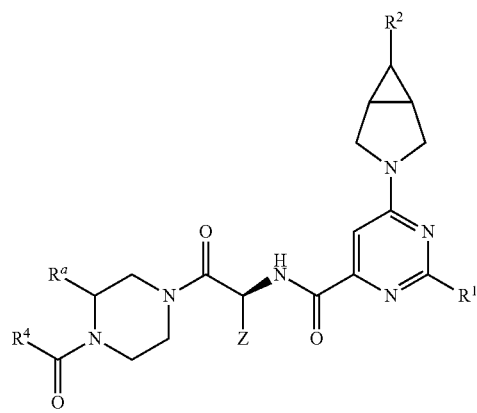

and to the salts (in particular pharmaceutically acceptable salts) of such compounds.

31) A preferred embodiment of the invention relates to compounds of formula I according to any one of embodiments 1) to 30), wherein the 3-aza-bicyclo[3.1.0]hex-3-yl moiety has a configuration as depicted in formula ABH$_1$ below

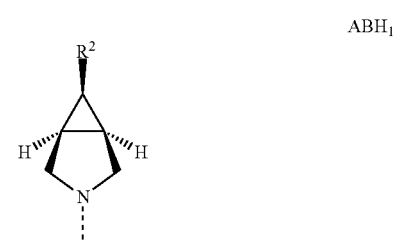

and to the salts (in particular pharmaceutically acceptable salts) of such compounds.

32) Another preferred embodiment of the invention relates to compounds of formula I according to any one of embodiments 1) to 30), wherein the 3-aza-bicyclo[3.1.0]hex-3-yl moiety has a configuration as depicted in formula ABH$_2$ below

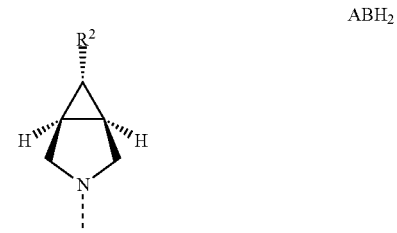

and to the salts (in particular pharmaceutically acceptable salts) of such compounds.

33) A preferred embodiment of the invention relates to compounds of formula I according to any one of embodiments 1) to 32), wherein, in case $R^a$ represents methyl, the stereogenic center within the piperazine moiety is (R)-configurated;

and to the salts (in particular pharmaceutically acceptable salts) of such compounds.

34) Preferred compounds of formula (I) as defined in embodiment 1) are selected from the group consisting of:

(1α,5α,6α)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid;

(1α,5α,6β)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid;

(1α,5α,6α)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid ethyl ester;

(1α,5α,6β)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid ethyl ester;

4-((S)-2-{[6-((1α,5α,6α)-6-tert-Butoxycarbonylamino-3-aza-bicyclo[3.1.0]hex-3-yl)-2-phenyl-pyrimidine-4-carbonyl]-amino}-4-carboxy-butyryl)-piperazine-1-carboxylic acid butyl ester;

4-((S)-2-{[6-((1α,5α,6β)-6-tert-Butoxycarbonylamino-3-aza-bicyclo[3.1.0]hex-3-yl)-2-phenyl-pyrimidine-4-carbonyl]-amino}-4-carboxy-butyryl)-piperazine-1-carboxylic acid butyl ester;

4-((S)-2-{[6-((1α,5α,6α)-6-Amino-3-aza-bicyclo[3.1.0]hex-3-yl)-2-phenyl-pyrimidine-4-carbonyl]-amino}-4-carboxy-butyryl)-piperazine-1-carboxylic acid butyl ester;

4-((S)-2-{[6-((1α,5α,6β)-6-Amino-3-aza-bicyclo[3.1.0]hex-3-yl)-2-phenyl-pyrimidine-4-carbonyl]-amino}-4-carboxy-butyryl)-piperazine-1-carboxylic acid butyl ester;

4-((S)-4-Carboxy-2-{[6-((1α,5α,6α)-6-hydroxymethyl-3-aza-bicyclo[3.1.0]hex-3-yl)-2-phenyl-pyrimidine-4-carbonyl]-amino}-butyryl)-piperazine-1-carboxylic acid butyl ester;

4-((S)-4-Carboxy-2-{[6-((1α,5α,6α)-6-methoxymethyl-3-aza-bicyclo[3.1.0]hex-3-yl)-2-phenyl-pyrimidine-4-carbonyl]-amino}-butyryl)-piperazine-1-carboxylic acid butyl ester;

(1α,5α,6β)-3-{6-[(S)-1-(4-Butoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid;

(1α,5α,6α)-3-{6-[(S)-1-(4-Butoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid;

(1α,5α,6β)-3-{6-[(S)-1-(4-Ethoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid;

(1α,5α,6β)-3-{6-[(S)-2-Methyl-1-(4-propoxycarbonyl-piperazine-1-carbonyl)-propylcarbamoyl]-2-phenyl-pyrimidin-4-yl}-3-aza-bicyclo[3.1.0]hexane-6-carboxylic acid;

(1α,5α,6β)-3-{6-[(S)-2-Methyl-1-(4-pentyloxycarbonyl-piperazine-1-carbonyl)-propylcarbamoyl]-2-phenyl-pyrimidin-4-yl}-3-aza-bicyclo[3.1.0]hexane-6-carboxylic acid;

(1α,5α,6β)-3-{6-[(S)-1-(4-Hexyloxycarbonyl-piperazine-1-carbonyl)-2-methyl-propylcarbamoyl]-2-phenyl-pyrimidin-4-yl}-3-aza-bicyclo[3.1.0]hexane-6-carboxylic acid;

4-((S)-2-{[6-((1α,5α,6α)-6-Carbamoyl-3-aza-bicyclo[3.1.0]hex-3-yl)-2-phenyl-pyrimidine-4-carbonyl]-amino}-3-methyl-butyryl)-piperazine-1-carboxylic acid butyl ester;

4-((S)-2-{[6-((1α,5α,6α)-6-Cyano-3-aza-bicyclo[3.1.0]hex-3-yl)-2-phenyl-pyrimidine-4-carbonyl]amino}-3-methyl-butyryl)-piperazine-1-carboxylic acid butyl ester;

4-[(S)-3-Methyl-2-({2-phenyl-6-[(1α,5α,6α)-6-(1H-tetrazol-5-yl)-3-aza-bicyclo[3.1.0]hex-3-yl]-pyrimidine-4-carbonyl}-amino)-butyryl]-piperazine-1-carboxylic acid butyl ester;

4-((S)-2-{[6-((1α,5α,6β)-6-Carbamoyl-3-aza-bicyclo[3.1.0]hex-3-yl)-2-phenyl-pyrimidine-4-carbonyl]-amino}-3-methyl-butyryl)-piperazine-1-carboxylic acid butyl ester;

4-((S)-2-{[6-((1α,5α,6β)-6-Cyano-3-aza-bicyclo[3.1.0]hex-3-yl)-2-phenyl-pyrimidine-4-carbonyl]-amino}-3-methyl-butyryl)-piperazine-1-carboxylic acid butyl ester;

4-[(S)-3-Methyl-2-({2-phenyl-6-[(1α,5α,6β)-6-(1H-tetrazol-5-yl)-3-aza-bicyclo[3.1.0]hex-3-yl]-pyrimidine-4-carbonyl}-amino)-butyryl]-piperazine-1-carboxylic acid butyl ester;

4-((S)-2-{[6-((1α,5α,6β)-6-Amino-3-aza-bicyclo[3.1.0]hex-3-yl)-2-phenyl-pyrimidine-4-carbonyl]amino}-3-methyl-butyryl)-piperazine-1-carboxylic acid butyl ester;

4-((S)-2-{[6-((1α,5α,6α)-6-Carboxymethyl-3-aza-bicyclo[3.1.0]hex-3-yl)-2-phenyl-pyrimidine-4-carbonyl]-amino}-3-methyl-butyryl)-piperazine-1-carboxylic acid butyl ester;

4-((S)-2-{[6-((1α,5α,6β)-6-Carboxymethyl-3-aza-bicyclo[3.1.0]hex-3-yl)-2-phenyl-pyrimidine-4-carbonyl]-amino}-3-methyl-butyryl)-piperazine-1-carboxylic acid butyl ester;

4-[(S)-2-({6-[1α,5α,6β)-6-(2-Carboxy-ethyl)-3-aza-bicyclo[3.1.0]hex-3-yl]-2-phenyl-pyrimidine-4-carbonyl}-amino)-3-methyl-butyryl]-piperazine-1-carboxylic acid butyl ester;

4-[(S)-2-({6-[(1α,5α,6α)-6-(2-Carboxy-ethyl)-3-aza-bicyclo[3.1.0]hex-3-yl]-2-phenyl-pyrimidine-4-carbonyl}-amino)-3-methyl-butyryl]-piperazine-1-carboxylic acid butyl ester;

(1α,5α,6β)-3-[6-[(S)-1-(4-Butoxycarbonyl-piperazine-1-carbonyl)-2-methyl-propylcarbamoyl]-2-(4-fluoro-phenyl)-pyrimidin-4-yl]-3-aza-bicyclo[3.1.0]hexane-6-carboxylic acid;

(1α,5α,6β)-3-{6-[(S)-1-(4-Butoxycarbonyl-piperazine-1-carbonyl)-2-methyl-propylcarbamoyl]-2-p-tolyl-pyrimidin-4-yl}-3-aza-bicyclo[3.1.0]hexane-6-carboxylic acid;

(1α,5α,6β)-3-[6-[(S)-1-(4-Butoxycarbonyl-piperazine-1-carbonyl)-2-methyl-propylcarbamoyl]-2-(3-trifluoromethyl-phenyl)-pyrimidin-4-yl]-3-aza-bicyclo[3.1.0]hexane-6-carboxylic acid;

(1α,5α,6β)-3-{6-[(S)-1-((R)-4-Butoxycarbonyl-3-methyl-piperazine-1-carbonyl)-2-methyl-propylcarbamoyl]-2-phenyl-pyrimidin-4-yl}-3-aza-bicyclo[3.1.0]hexane-6-carboxylic acid;

(1α,5α,6β)-3-{6-[(S)-1-((R)-4-Benzyloxycarbonyl-3-methyl-piperazine-1-carbonyl)-2-methyl-propylcarbamoyl]-2-phenyl-pyrimidin-4-yl}-3-aza-bicyclo[3.1.0]hexane-6-carboxylic acid;

(1α,5α,6β)-3-{6-[2-(4-Butoxycarbonyl-piperazin-1-yl)-2-oxo-ethylcarbamoyl]-2-phenyl-pyrimidin-4-yl}-3-aza-bicyclo[3.1.0]hexane-6-carboxylic acid;

(1α,5α,6α)-3-{6-[(S)-2-(4-Butoxycarbonyl-piperazin-1-yl)-1-methyl-2-oxo-ethylcarbamoyl]-2-phenyl-pyrimidin-4-yl}-3-aza-bicyclo[3.1.0]hexane-6-carboxylic acid;

(1α,5α,6β)-3-{6-[(S)-2-(4-Butoxycarbonyl-piperazin-1-yl)-1-methyl-2-oxo-ethylcarbamoyl]-2-phenyl-pyrimidin-4-yl}-3-aza-bicyclo[3.1.0]hexane-6-carboxylic acid;

(1α,5α,6β)-3-{6-[(S)-1-(4-Butoxycarbonyl-piperazine-1-carbonyl)-propylcarbamoyl]-2-phenyl-pyrimidin-4-yl}-3-aza-bicyclo[3.1.0]hexane-6-carboxylic acid;

(1α,5α,6β)-3-{6-[(S)-1-(4-Butoxycarbonyl-piperazine-1-carbonyl)-butylcarbamoyl]-2-phenyl-pyrimidin-4-yl}-3-aza-bicyclo[3.1.0]hexane-6-carboxylic acid;

(1α,5α,6β)-3-{6-[(S)-1-(4-Butoxycarbonyl-piperazine-1-carbonyl)-pentylcarbamoyl]-2-phenyl-pyrimidin-4-yl}-3-aza-bicyclo[3.1.0]hexane-6-carboxylic acid;

(1α,5α,6β)-3-{6-[(S)-1-(4-Butoxycarbonyl-piperazine-1-carbonyl)-3-methyl-butylcarbamoyl]-2-phenyl-pyrimidin-4-yl}-3-aza-bicyclo[3.1.0]hexane-6-carboxylic acid;
(1α,5α,6β)-3-{6-[(S)-2-(4-Butoxycarbonyl-piperazin-1-yl)-1-cyclopropylmethyl-2-oxo-ethylcarbamoyl]-2-phenyl-pyrimidin-4-yl}-3-aza-bicyclo[3.1.0]hexane-6-carboxylic acid;
(1α,5α,6β)-3-{6-[(S)-2-(4-Butoxycarbonyl-piperazin-1-yl)-1-cyclopropyl-2-oxo-ethylcarbamoyl]-2-phenyl-pyrimidin-4-yl}-3-aza-bicyclo[3.1.0]hexane-6-carboxylic acid;
(1α,5α,6β)-3-{6-[(1S,2R)-1-(4-Butoxycarbonyl-piperazine-1-carbonyl)-2-hydroxy-propylcarbamoyl]-2-phenyl-pyrimidin-4-yl}-3-aza-bicyclo[3.1.0]hexane-6-carboxylic acid;
(1α,5α,6β)-3-{6-[(S)-1-(4-Butoxycarbonyl-piperazine-1-carbonyl)-2,2-dimethyl-propylcarbamoyl]-2-phenyl-pyrimidin-4-yl}-3-aza-bicyclo[3.1.0]hexane-6-carboxylic acid;
(1α,5α,6α)-3-{6-[(S)-1-(4-Butoxycarbonyl-piperazine-1-carbonyl)-2,2-dimethyl-propylcarbamoyl]-2-phenyl-pyrimidin-4-yl}-3-aza-bicyclo[3.1.0]hexane-6-carboxylic acid;
(1α,5α,6β)-3-{6-[(S)-1-Benzyl-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid;
(1α,5α,6α)-3-{6-[(S)-1-Benzyl-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid;
(1α,5α,6β)-3-[6-[(S)-1-(4-Butoxycarbonyl-piperazine-1-carbonyl)-2-methyl-propylcarbamoyl]-2-(2-fluoro-phenyl)-pyrimidin-4-yl]-3-aza-bicyclo[3.1.0]hexane-6-carboxylic acid;
(1α,5α,6β)-3-{6-[(S)-1-(4-Butoxycarbonyl-piperazine-1-carbonyl)-2-cyano-ethylcarbamoyl]-2-phenyl-pyrimidin-4-yl}-3-aza-bicyclo[3.1.0]hexane-6-carboxylic acid;
(1α,5α,6β)-3-{6-[(S)-1-(4-Butoxycarbonyl-piperazine-1-carbonyl)-3-(1H-tetrazol-5-yl)-propylcarbamoyl]-2-phenyl-pyrimidin-4-yl}-3-aza-bicyclo[3.1.0]hexane-6-carboxylic acid;
(1α,5α,6α)-3-{6-[(R)-2-(4-Butoxycarbonyl-piperazin-1-yl)-1-(diethoxy-phosphorylmethyl)-2-oxo-ethylcarbamoyl]-2-phenyl-pyrimidin-4-yl}-3-aza-bicyclo[3.1.0]hexane-6-carboxylic acid ethyl ester;
(1α,5α,6α)-3-{6-[(R)-2-(4-Butoxycarbonyl-piperazin-1-yl)-2-oxo-1-phosphonomethyl-ethylcarbamoyl]-2-phenyl-pyrimidin-4-yl}-3-aza-bicyclo[3.1.0]hexane-6-carboxylic acid ethyl ester;
(1α,5α,6α)-3-{6-[(R)-1-(Bis-acetoxymethoxy-phosphorylmethyl)-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid ethyl ester;
N,N'-Bis-((S)-1-Ethoxycarbonylethyl)-(R)-2-[(4-[(1α,5α,6α)-6-ethoxycarbonyl-3-aza-bicyclo[3.1.0]hex-3-yl]-2-phenyl-pyrimidin-6-carbonyl)-amino]-3-oxo-3-(4-butoxy-carbonyl-piperazin-1-yl)-propyl-phosphonic acid diamide; and
(1α,5α,6α)-3-{6-[(R)-1-(Bis-ethoxycarbonyloxymethoxy-phosphorylmethyl)-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid ethyl ester;
or a salt (in particular a pharmaceutically acceptable salt) of such a compound;
wherein it is well understood that any stereogenic center of any above listed compound, which is not explicitly assigned, may be in absolute (R)- or (S)-configuration.

35) A further object of the invention is the compounds of formula I, as defined in one of embodiments 1) to 34) above, or their pharmaceutically acceptable salts, as medicaments.

The compounds of formula I and their pharmaceutically acceptable salts can be used as medicaments, e.g. in the form of pharmaceutical compositions for enteral or parenteral administration.

36) The invention thus also relates to pharmaceutical compositions containing at least one compound according to one of embodiments 1) to 34) above, or a pharmaceutically acceptable salt thereof, and a pharmaceutically acceptable carrier, diluent or excipient. In particular, the invention relates to pharmaceutical compositions containing at least one compound of formula I and one or more pharmaceutically acceptable carriers, diluents or excipients.

The production of the pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

37) The compounds according to formula I as defined in one of embodiments 1) to 34) above and the pharmaceutically acceptable salts thereof may be used for the preparation of a medicament, and are suitable:
for the treatment or prophylaxis of diseases including stable angina, unstable angina, myocardial infarction, embolism (including complications of atherosclerosis, notably embolic stroke), arterial thrombosis (including primary arterial thrombotic complications of atherosclerosis, notably thrombotic stroke), venous thrombosis (notably deep vein thrombosis), thrombosis secondary to vascular damage or to inflammation (including vasculitis, arteritis and glomerulonephritis), venoocclusive diseases, transient ischaemic attacks, peripheral vascular diseases, myocardial infarction with or without thrombolysis, myeloproliferative disease, thrombocythaemia, sickle cell disease, inflammatory bowel disease, thrombotic thrombocytopaenic purpura, haemolytic uraemic syndrome;
for preventing thrombotic complications of septicaemia, adult respiratory distress syndrome, anti-phospholipid syndrome, heparin-induced thrombocytopaenia and pre-eclampsia/eclampsia;
for preventing cardiovascular complications after certain surgery procedures (notably coronary revascularisation like angioplasty (PTCA), other vascular graft surgery, endarterectomy or stent placement) or after accidental trauma;
for preventing organ graft rejection;
for preventing complications in conditions in which vasospasms lead to vasoconstriction and thus tissue-ischemia or tissue-death (necrosis).

38) Therefore, a particular object of this invention is the use of a compound of formula I as defined in one of embodiments 1) to 34) above, or of a pharmaceutically acceptable salt thereof, for the manufacture of a medicament for the uses listed in embodiment 37) above, and for the manufacture of a medicament for the treatment of occlusive vascular disorders in general.

39) More generally, the invention relates to the use of a compound of formula I as defined in one of embodiments 1) to 34) above, or of a pharmaceutically acceptable salt thereof, for the manufacture of a medicament for the treatment and/or prevention of occlusive vascular disorders as well as to the use of a compound of formula I for the manufacture of a medicament for the treatment and/or prevention of peripheral vascular, of visceral-, hepatic- and renal-vascular, of cardiovascular and of cerebrovascular diseases or conditions associated with platelet aggregation, including thrombosis in humans and other mammals.

40) Among the above-mentioned uses of compounds of formula I or of pharmaceutically acceptable salts thereof for the manufacture of medicaments according to embodiment 38) above, the uses for manufacturing medicaments for the treatment or prophylaxis of myocardial infarction, arterial thrombosis (notably thrombotic stroke), transient ischaemic attacks, peripheral vascular disease and stable and unstable angina will be preferred.

41) The invention further relates to the use of a compound of formula I according to one of embodiments 1) to 34) above, or of a pharmaceutically acceptable salt thereof, for the preservation of blood products in vitro (e.g. the preservation of platelet concentrates), or for the prevention of occlusion in extra-corporeal blood or blood product treatment machines (such as renal dialysis machines or plasmapheresis machines).

42) The invention also relates to methods of treatment for the disorders mentioned in embodiment 37) above, said methods comprising the administration to a patient in need thereof of an effective amount of a compound of formula I according to one of embodiments 1) to 34), or of a pharmaceutically acceptable salt of such a compound.

The present invention also includes isotopically labelled, especially $^2$H (deuterium) labelled compounds of formula I, which compounds are identical to the compounds of formula I except that one or more atoms have each been replaced by an atom having the same atomic number but an atomic mass different from the atomic mass usually found in nature. Isotopically labelled, especially $^2$H (deuterium) labelled compounds of formula I and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula I are not isotopically labelled, or they are labelled only with one or more deuterium atoms. In a sub-embodiment, the compounds of formula I are not isotopically labelled at all. Isotopically labelled compounds of formula I may be prepared in analogy to the methods described hereinafter, but using the appropriate isotopic variation of suitable reagents or starting materials.

Any reference to a compound of formula I in this text is to be understood as referring also to the salts (and especially the pharmaceutically acceptable salts) of such compounds, as appropriate and expedient. The preferences indicated for the compounds of formula I of course apply mutatis mutandis to the salts and pharmaceutically acceptable salts of the compounds of formula I. The same applies to these compounds as medicaments, to pharmaceutical compositions containing these compounds as active principles, to the uses of these compounds for the manufacture of a medicament for the treatment of the diseases according to this invention or to the compounds for the treatment of the diseases according to this invention.

According to the invention, the compounds of formula I can be prepared by the process described below.
Preparation of the Compounds of Formula I
Abbreviations:
The following abbreviations are used throughout the specification and the examples:

| | |
|---|---|
| AcOH | acetic acid |
| ADP | adenosine diphosphate |
| aq. | aqueous |
| Bn | benzyl |
| Boc | tert-butoxycarbonyl |
| BSA | bovine serum albumin |
| n-BuLi | n-butyllithium |
| Burgess reagent | (methoxycarbonylsulfamoyl)triethylammonium hydroxide |
| Cbz | benzyloxycarbonyl |
| CC | column chromatography |
| CV | column volume |
| DCC | N,N'-dicyclohexylcarbodiimide |
| DCM | dichloromethane |
| DIBAL | diisobutylaluminum hydride |
| DIPEA | diisopropylethylamine |
| DMAP | 4-dimethylaminopyridine |
| DMF | N,N-dimethylformamide |
| DMP | Dess-Martin periodinane |
| DMPU | N,N'-dimethylpropyleneurea |
| dpm | decays per minute |
| DPPA | diphenyl phosphoryl azide |
| EA | ethyl acetate |
| EDCI | N-(3-dimethylaminopropyl)-N'-ethylcarbodiimide hydrochloride |
| EDTA | Ethylenediaminetetraacetic acid |
| Et | ethyl |
| EtOH | ethanol |
| Et$_2$O | diethyl ether |
| HATU | 2-(7-aza-1H-benzotriazole-1-yl)-1,1,3,3-tetramethyluronium hexafluorophosphate |
| Hept | heptane |
| HOBT | 1-hydroxybenzotriazole |
| HV | high vacuum |
| LC-MS | Liquid Chromatography - Mass Spectrometry |
| Me | methyl |
| MeCN | acetonitrile |
| MeI | methyl iodide |
| MeOH | methanol |
| NaHMDS | sodium bis(trimethylsilyl)amide |
| NMM | N-methylmorpholine |
| NMP | N-methylpyrrolidone |
| org. | organic |
| Pd/C | palladium on carbon |
| Ph | phenyl |
| PyBOP | benzotriazole-1-yl-oxy-tris-pyrrolidino-phosphonium hexafluorophosphate |
| RT | room temperature |
| SDS | sodium dodecyl sulfate |
| TBAF | tetrabutylammonium fluoride |
| TBDMS | tert-butyldimethylsilyl |
| tBu | tert-butyl |
| TEA | triethylamine |
| TFA | trifluoroacetic acid |
| THF | tetrahydrofuran |
| TLC | thin layer chromatography |
| t$_R$ | retention time |
| Tris | tris(hydroxymethyl)aminomethane |

General Preparation Routes:
A further aspect of the invention is a process for the preparation of compounds of formula (I). Compounds of formula (I) of the present invention can be prepared according to the general sequence of reactions outlined in the schemes below wherein Z, $R^1$, $R^2$, $R^3$, $R^4$, $R^5$, $R^6$, $R^7$, $R^8$ and $R^a$ are as defined for formula (I). The compounds obtained may also be converted into pharmaceutically acceptable salts thereof in a manner known per se.

In general, all chemical transformations can be performed according to well-known standard methodologies as described in the literature or as described in the procedures below or in the experimental part.

The various compounds of formula I can be prepared using the general routes summarized in Scheme 1 hereafter.

suitable protecting group for an amine function such as a Boc group which can be removed under acidic conditions. Other suitable amine function protection groups and protection and deprotection methods are well known to one skilled in the art Scheme 1

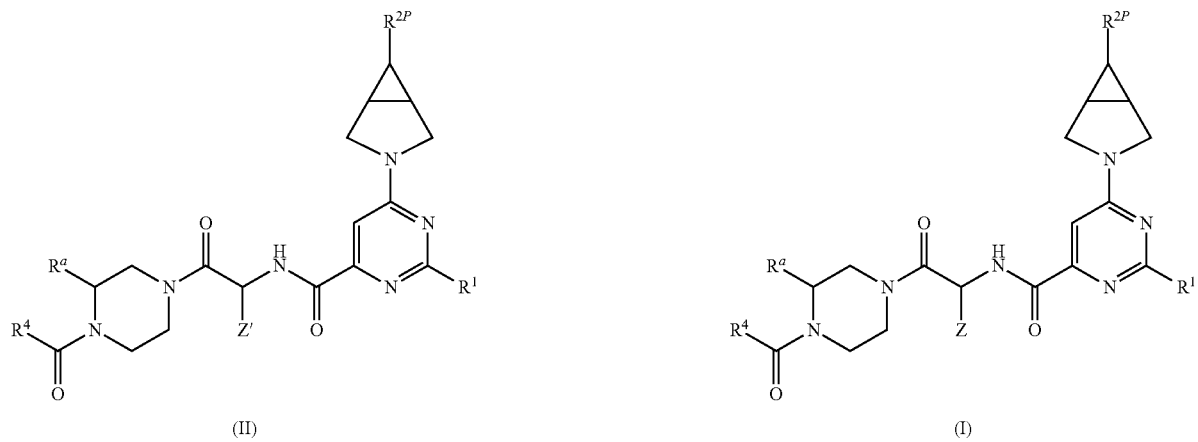

| | |
|---|---|
| $Z' = (C_1-C_4)$alkoxycarbonyl-$(C_1-C_3)$alkyl $(R^{2P} = R^2)$ | $Z = $ carboxy-$(C_1-C_3)$alkyl |
| $Z' = $ cyano-$(C_1-C_3)$alkyl $(R^{2P} = R^2)$ | $Z = $ 1H-tetrazol-5-yl-$(C_1-C_3)$alkyl |
| $R^{2P} = $ -COOR$^3$ $(Z' = Z)$ | $R^2 = $ —COOH |
| $R^{2P} = (C_1-C_4)$alkoxycarbonyl-$(C_1-C_3)$alkyl $(Z' = Z)$ | $R^2 = $ carboxy-$(C_1-C_3)$alkyl |
| $R^{2P} = $ —NH—PG$_1$ $(Z' = Z)$ | $R^2 = $ —NH$_2$ |
| $R^{2P} = $ —CONH$_2$ $(Z' = Z)$ | $R^2 = $ cyano or 1H-tetrazol-5-yl |
| $R^{2P} = $ PG$_2$—O—$(C_1-C_3)$alkyl $(Z' = Z)$ | $R^2 = $ hydroxy-$(C_1-C_3)$alkyl |

The acids of formula I wherein Z is carboxy-$(C_1-C_3)$alkyl can be obtained (Scheme 1) by hydrolysis of the corresponding compounds of formula II wherein Z' is $(C_1-C_4)$alkoxycarbonyl-$(C_1-C_3)$alkyl under standard conditions, either under basic conditions using standard reagents such as NaOH or LiOH in a mixture of water and a suitable organic solvent such as THF, MeOH or EtOH, or under acidic conditions using standard reagents such as TFA in a suitable organic solvent such as DCM.

The tetrazole derivatives of formula I wherein Z is 1H-tetrazol-5-yl-$(C_1-C_3)$alkyl can be prepared (Scheme 1) by conversion of the corresponding cyano derivatives of formula II wherein Z' is cyano-$(C_1-C_3)$alkyl using either the well known methodology with sodium azide or alternatively using trimethylsilylazide in the presence of TBAF.

The compounds of formula I wherein R$^2$ is —COOH or carboxy-$(C_1-C_3)$alkyl can be obtained (Scheme 1) by hydrolysis of the corresponding esters of formula II wherein R$^{2P}$ is —COOR$^3$ or $(C_1-C_4)$alkoxycarbonyl-$(C_1-C_3)$alkyl, under standard conditions such as those already described for the synthesis of the compounds of formula I wherein Z is carboxy-$(C_1-C_3)$alkyl.

The compounds of formula I wherein R$^2$ is —NH$_2$ can be obtained (Scheme 1) by deprotection of the protected amines of formula II wherein R$^{2P}$ is —NH-PG$_1$ with PG$_1$ being a (see notably "Protective groups in organic synthesis", Greene T. W. and Wuts P. G. M., Wiley-Interscience, 1999).

The compounds of formula I wherein R$^2$ is 1H-tetrazol-5-yl can be prepared (Scheme 1) in a two step sequence comprising of conversion of the corresponding amide derivative of formula II wherein R$^{2P}$ is —CONH$_2$ with Burgess reagent to the respective cyano derivative (R$^2$=cyano); and conversion of the cyano derivative using the well-known methodology with sodium azide, optionally in the presence of zinc dibromide, to the respective tetrazole derivative.

The compounds of formula I wherein R$^2$ is hydroxy-$(C_1$-$C_3)$alkyl can be obtained (Scheme 1) by deprotection of the protected alcohols of formula II wherein R$^{2P}$ is PG$_2$-O—$(C_1$-$C_3)$alkyl with PG$_2$ being a suitable protecting group for an alcohol function such as a silyl protecting group like TBDMS which can be removed under acidic conditions. Other suitable alcohol function protection groups and protection and deprotection methods are well known to one skilled in the art (see notably "Protective groups in organic synthesis", Greene T. W. and Wuts P. G. M., Wiley-Interscience, 1999).

Compounds of formula I, wherein Z represents P(O)(R$^6$)$_2$—$(C_1$-$C_3)$alkyl, can be prepared using the general routes summarized in Scheme 1a hereafter.

Scheme 1a

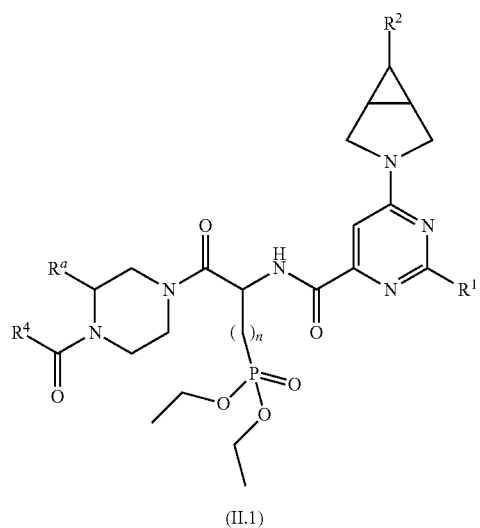

(II.1)

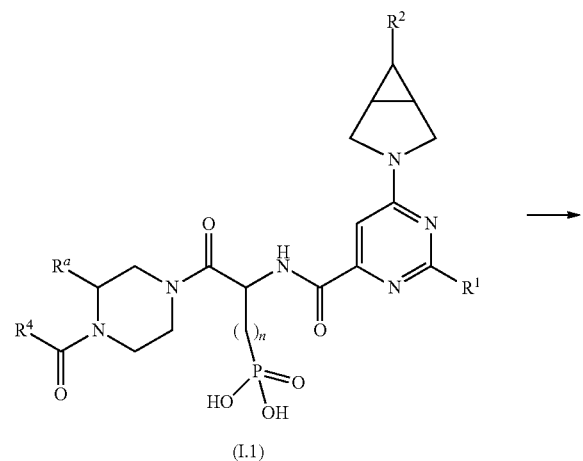

(I.1)

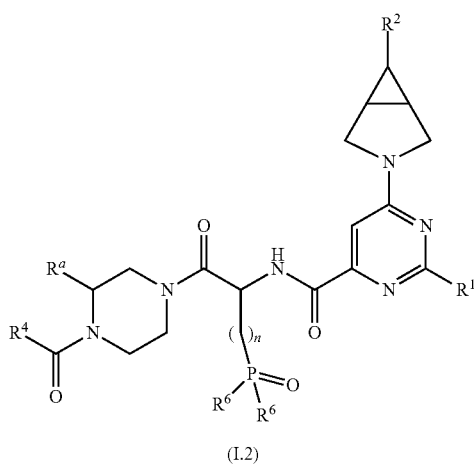

(I.2)

Synthesis of Phosphonic Acid Derivatives Wherein n Represents 1, 2 or 3 and $R^6$ Represents $R^7$—OCH$_2$O— or $R^8$—(C$_1$-C$_4$)alkyl-NH—

The compounds of formula I.1, wherein $R^6$ represents hydroxy, can be prepared by treating the compounds of formula II.1 with HCl optionally in the presence of water, in a suitable organic solvent such as THF, EA, dioxane or Et$_2$O and preferably at a temperature around RT, or with trimethylsilyl bromide or trimethylsilyl iodide in a suitable solvent such as DCM or MeCN and preferably at a temperature around RT (scheme 1a).

The compounds of formula I.2, wherein $R^6$ represents $R^7$—OCH$_2$O—, can be prepared by the reaction between a phosphonic acid of formula I.1 and an appropriate halide derivative of formula $R^7$—OCH$_2$—X, X being chloride, bromide or iodide, in the presence of a suitable base (e.g. NEt$_3$, DIPEA) in a suitable solvent such as DMF, NMP or DMPU, optionally in the presence of NaI and preferably at a temperature between 45 and 90° C. (scheme 1a).

The compounds of formula I.2, wherein $R^6$ represents $R^8$—(C$_1$-C$_4$)alkyl-NH—, can be prepared by the reaction between a phosphonic acid of formula I.1 and an appropriate amino acid alkyl ester (preferably an α-amino acid alkyl ester) of formula $R^8$—(C$_1$-C$_4$)alkyl-NH$_2$ in the presence of a suitable base (e.g. NEt$_3$) and an activating mixture of reagents such as a combination of 2,2'-dipyridyl disulfide and PPh$_3$ in a suitable solvent such as anhydrous pyridine and preferably at a temperature of about 60° C. (scheme 1a).

Preparation of the Compounds of Formula II and of Formula II.1

The compounds of formula II can be prepared using the route summarized in Scheme 2 and 2a hereafter. It is to be understood that for some meanings of the residues Z' and $R^{2P}$ the compounds of formula II are also compounds of formula I.

The compounds of formula V wherein Z' is hydrogen, (C$_1$-C$_4$)alkyl, cyclopropyl, cyclopropylmethyl, hydroxy-(C$_1$-C$_3$)alkyl, cyano-(C$_1$-C$_3$)alkyl, P(O)(R$^6$)$_2$—(C$_1$-C$_3$)alkyl (R$^6$=ethoxy), (C$_1$-C$_4$)alkoxycarbonyl-(C$_1$-C$_3$)alkyl or benzyl can be obtained (Scheme 2) by coupling the piperazine derivative of formula III wherein Z' is hydrogen, (C$_1$-C$_4$) alkyl, cyclopropyl, cyclopropylmethyl, hydroxy-(C$_1$-C$_3$) alkyl, cyano-(C$_1$-C$_3$)alkyl, P(O)(R$^6$)$_2$—(C$_1$-C$_3$)alkyl (R$^6$=ethoxy), (C$_1$-C$_4$)alkoxycarbonyl-(C$_1$-C$_3$)alkyl or benzyl with a compound of formula IV using standard peptide coupling methods such as PyBOP or HATU, in the presence of a suitable base such as NEt$_3$, DIPEA or N-methylmorpholine and in a suitable solvent such as DCM, THF or DMF, preferably at a temperature around RT.

The resulting intermediate of formula V can then be converted into a compound of formula II or of formula II.1 wherein Z' is hydrogen, (C$_1$-C$_4$)alkyl, cyclopropyl, cyclopropylmethyl, hydroxy-(C$_1$-C$_3$)alkyl, cyano-(C$_1$-C$_3$)alkyl, P(O)(R$^6$)$_2$—(C$_1$-C$_3$)alkyl (R$^6$=ethoxy), (C$_1$-C$_4$)alkoxycarbonyl-(C$_1$-C$_3$)alkyl or benzyl and $R^{2P}$ is —CONH$_2$, —COOR$^3$, (C$_1$-C$_4$)alkoxycarbonyl-(C$_1$-C$_3$)alkyl, PG$_2$-O—(C$_1$-C$_3$) alkyl, (C$_1$-C$_2$)alkoxy-(C$_1$-C$_2$)alkyl, or —NH-PG$_1$ by aromatic nucleophilic substitution reaction with a compound of formula VI wherein $R^{2P}$ is —CONH$_2$, —COOR$^3$, (C$_1$-C$_4$) alkoxycarbonyl-(C$_1$-C$_3$)alkyl, PG$_2$-O—(C$_1$-C$_3$)alkyl, (C$_1$-C$_2$)alkoxy-(C$_1$-C$_2$)alkyl or —NH-PG$_1$ optionally in the presence of a suitable base such as NEt$_3$, DIPEA or N-methylmorpholine, the reaction being carried out in a suitable solvent such as DCM, THF, MeCN or DMF and preferably between RT and 70° C.

Scheme 2
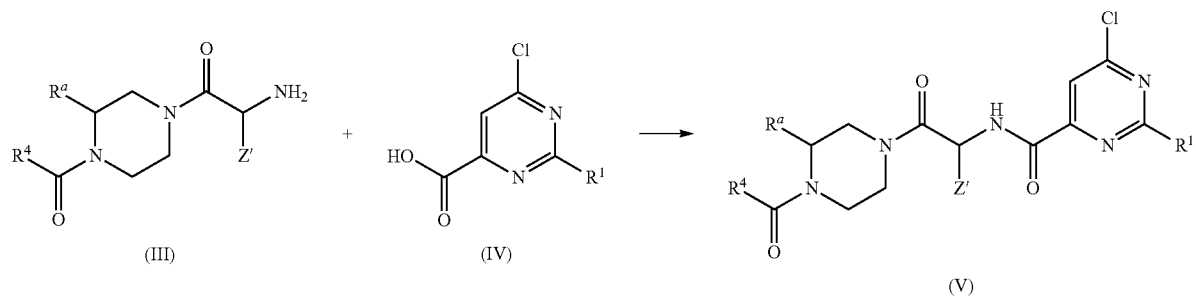
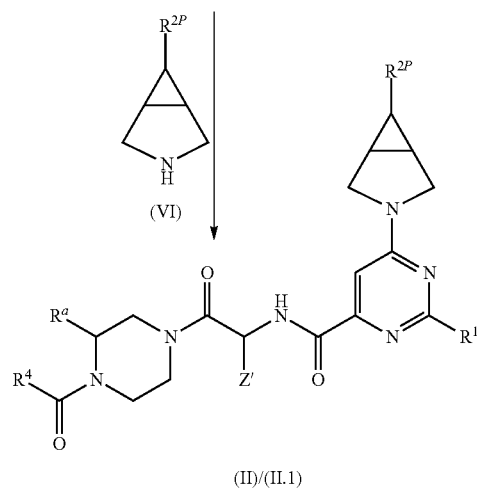
Alternatively, the compounds of formula II can be prepared using the route summarized in Scheme 2a hereafter.
Scheme 2a
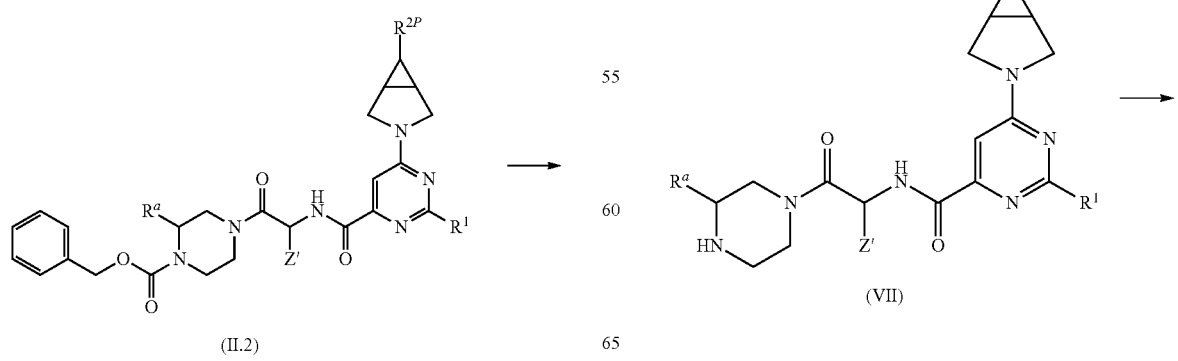
-continued

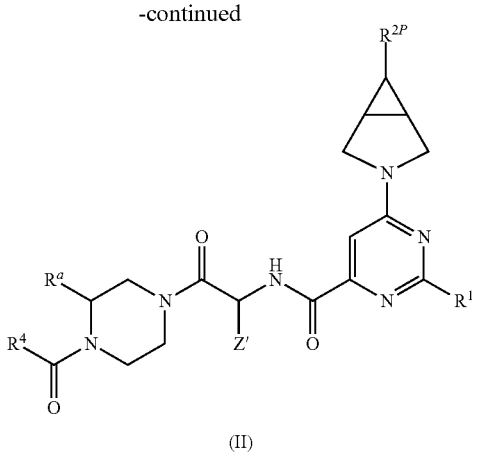

(II)

The compounds of formula II.2, prepared according to scheme 2 (R⁴=benzyloxy), can be hydrogenated (e.g. palladium on charcoal in EtOH, MeOH or EA, under hydrogen) to give the compounds of formula VII. Reaction of the compounds of formula VII with a reagent of formula R⁴COCl (R⁴ being $(C_1-C_6)$alkoxy) in presence of a suitable base such as NEt$_3$ or DIPEA in a suitable solvent such as DCM and between 0° C. and RT leads to compounds of formula II wherein R⁴ is $(C_1-C_6)$alkoxy.

Preparation of the Compounds of Formula IV

The compounds of formula IV can be prepared using the route described in WO06114774, general preparation routes, preparation of the compounds of formula IV, Scheme 4a.

Preparation of the Compounds of Formula VI

The compounds of formula VI wherein $R^{2P}$ is —COOR³ or —CONH$_2$ can be prepared using the route summarized in Scheme 3 hereafter.

Scheme 3

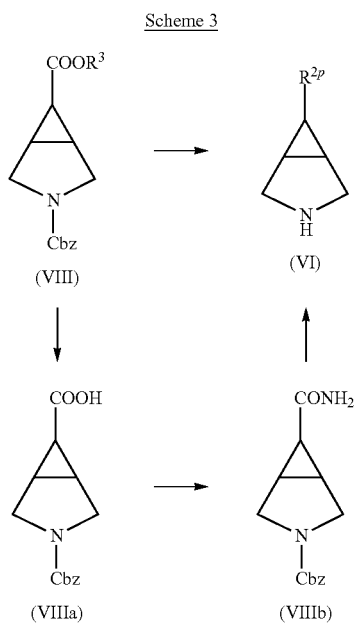

The acid derivative (VIIIa) can be obtained by a saponification reaction of a compound of formula VIII using standard conditions such as those already described for the synthesis of the compounds of formula I. Subsequent reaction of the acid derivative with NH$_4$OH in the presence of isobutyryl chloroformate, a base such as NMM in a suitable solvent such as THF, preferably between −15° C. and RT, gives access to the amide derivative (VIIIb). The amide derivative VIIIb as well as the ester derivative of formula VIII can be deprotected to give the compounds of formula VI using standard methods for the removal of a Cbz group that are well known to one skilled in the art (e.g. palladium on charcoal in EtOH, MeOH or EA, under hydrogen).

The compounds of formula VI wherein $R^{2P}$ is NH-PG$_1$ can be prepared (Scheme 3a) by converting the acid derivative VIIIa into the corresponding amine derivative of formula IX via a Curtius rearrangement under standard conditions using DPPA in a suitable solvent such as toluene or THF between RT and reflux, and optionally by adding tert-butanol. The intermediate of formula IX can be selectively deprotected at the ring nitrogen atom (in the presence of PG$_1$) using standard methods for the removal of a Cbz group such as those already described for the synthesis of the compounds of formula VI wherein $R^{2P}$ is —COOR³ or —CONH$_2$ (see Scheme 3).

Scheme 3a

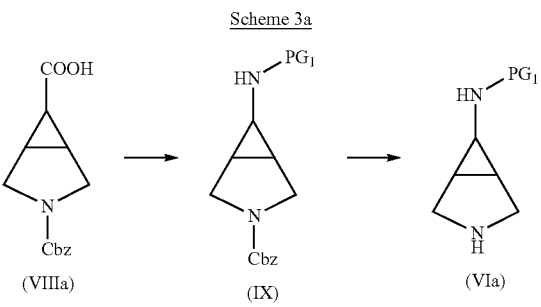

Synthesis of Compounds of Formula VI Wherein $R^{2P}$ is NH-PG$_1$

The compounds of formula VI wherein $R^{2P}$ is $(C_1-C_2)$alkoxy-$(C_1-C_2)$alkyl or PG$_2$-O-$(C_1-C_3)$alkyl (PG$_2$ being a suitable protecting group for an alcohol function such as a silyl protecting group) can be prepared using the route summarized in Scheme 3b hereafter. The alcohol derivative of formula XI can be obtained by reduction of the ester function of a compound of formula X using a reducing agent such as DIBAL in a suitable solvent such as DCM between −10° C. and RT. The alcohol function can then be protected with a suitable protecting group for an alcohol function such as a silyl protecting group like TBDMS to give the compound of formula XII wherein R⁹ is PG$_2$. Suitable alcohol function protection groups and protection and deprotection methods are well known to one skilled in the art (see notably "Protective groups in organic synthesis", Greene T. W. and Wuts P. G. M., Wiley-Interscience, 1999).

O-alkylation of an alcohol derivative of formula XI can be performed using an alkylating agent of formula R⁹-LG (wherein LG represents a leaving group such as a halogen atom), in adequate solvents like THF or DMF, in the presence of an appropriate base such as NaH, yielding the compound of formula XII wherein R⁹ is $(C_1-C_2)$alkyl. The different intermediates of formula XII can be finally deprotected to give compounds of formula VIb wherein R⁹ is $(C_1-C_2)$alkyl or PG$_2$, using standard conditions for the removal of a Cbz group as described above.

Scheme 3b

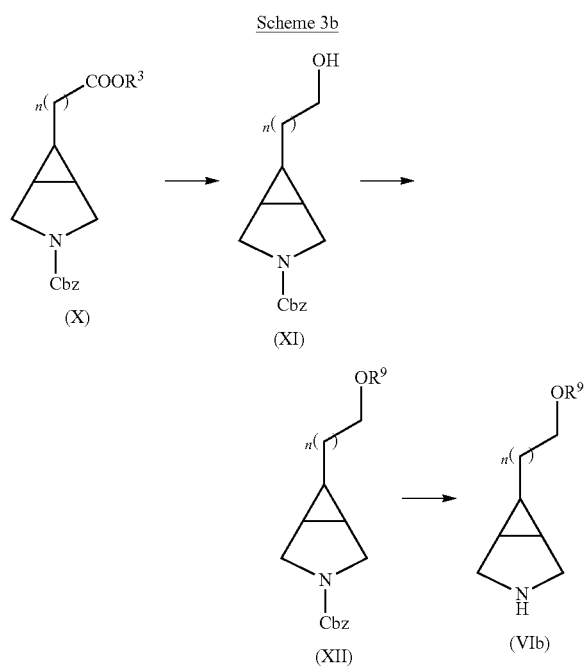

Synthesis of Compounds of Formula VI Wherein $R^{2P}$ is $(C_1-C_2)$alkoxy-$(C_1-C_2)$alkyl or $PG_2$-O—$(C_1-C_3)$alkyl($R^9$=$(C_1-C_2)$alkyl and n=0, 1 or $R^9$=$PG_2$ and n=0, 1, 2)

The compounds of formula VI wherein $R^{2P}$ is $(C_1-C_4)$ alkoxycarbonyl-$(C_1-C_3)$alkyl can be prepared by the route described in Scheme 3c. The alcohol derivatives of formula XI can be oxidized using known oxidizing reagents such as Dess-Martins-Periodinane, in presence of a suitable base such as sodium bicarbonate, in a suitable solvent such as DCM and preferably at a temperature around RT. The intermediate aldehydes of formula XIII can be converted into an elongated aldehyde of formula XIV via a Wittig olefination using methoxymethyltriphenyl-phosphonium chloride in the presence of a suitable base such as NaHMDS and in an adequate solvent such as THF, preferably at a temperature between −78° C. and RT. The obtained enolether can then be hydrolyzed to the corresponding elongated aldehyde derivative of formula XIV under standard conditions (e.g. HCl in acetone). Subsequent oxidation of the elongated aldehyde derivative to form the acid derivative of formula XV can be carried out under conditions of the Pinnick oxidation, using sodium chlorite in the presence of 2-methyl-2-butene, in a suitable solvent such as tert-butanol and at a temperature around RT. Esterification of the acid derivative of formula XV under standard conditions (e.g. $R^3$OH, DCC, DMAP in DCM) gives the intermediate of formula XVI. Cleavage of the Cbz group yields the compound of formula VIc wherein n is 0, 1 or 2.

Scheme 3c

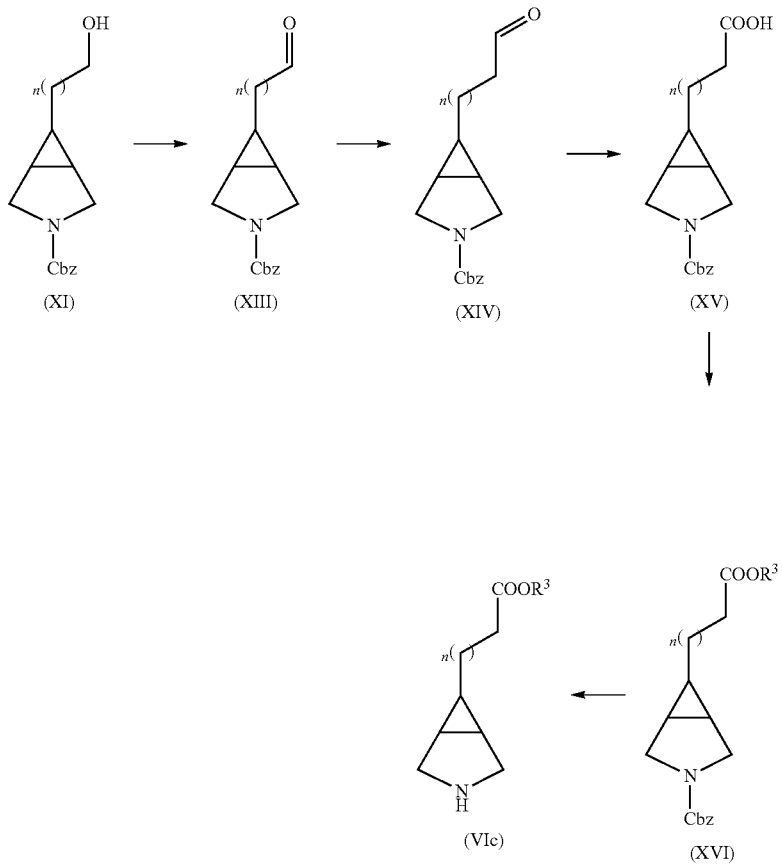

Synthesis of Compounds of Formula VI Wherein $R^{2P}$ is $(C_1-C_4)$alkoxycarbonyl-$(C_1-C_3)$alkyl (n=0, 1 or 2)

Alternatively the compounds of formula VI wherein $R^{2P}$ is $(C_1-C_4)$alkoxycarbonyl-$(C_2-C_3)$alkyl can be prepared by the route described in Scheme 3d. The intermediate aldehydes of formula XIII can be converted into an α,β-unsaturated ester of formula XVII using standard conditions for a Wittig olefination, using a suitable reagent of formula $Ph_3P=CH—COOR^3$, in a suitable solvent such as THF and preferably heating at a temperature around 75° C. Cbz removal from the intermediates of formula XVII gives, under hydrogenation conditions as described above, access to the ester derivative of formula VId wherein n is 0 or 1.

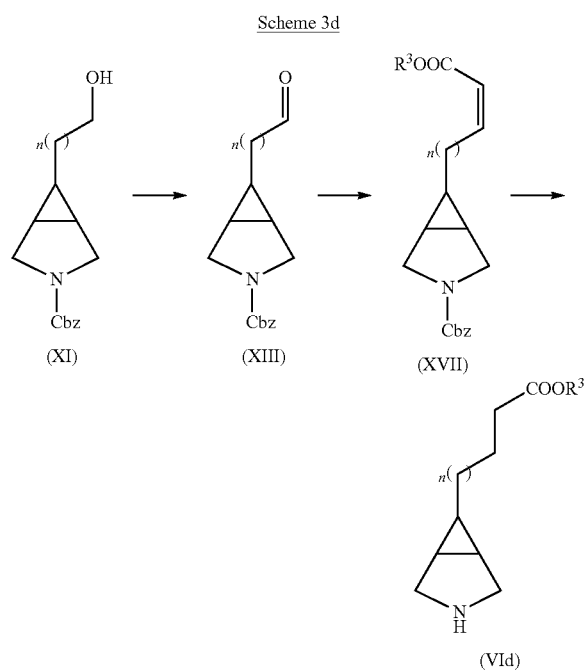

Synthesis of Compounds of Formula VI Wherein $R^{2P}$ is $(C_1-C_4)$alkoxycarbonyl-$(C_2-C_3)$alkyl (n=0 or 1)

Preparation of the Compounds of Formula VIII

The compounds of formula VIII and X (n=0) can be prepared using the route described by Brighty K. E. et al in *Synlett* (1996), 1097-1099.

Preparation of the Compounds of Formula X

The compounds of formula X wherein n is 1 can be prepared by chain elongation of the compounds of formula X wherein n is 0, by performing successively the first step described in Scheme 3b followed by the first four steps described in Scheme 3c.

The compounds of formula X wherein n is 2 can be prepared by chain elongation of the compounds of formula X wherein n is 1, following the same procedure as described for the preparation of the compounds of formula X wherein n is 1.

Preparation of the Compounds of Formula III

The compounds of formula III can be prepared using the route summarized in Scheme 4 hereafter.

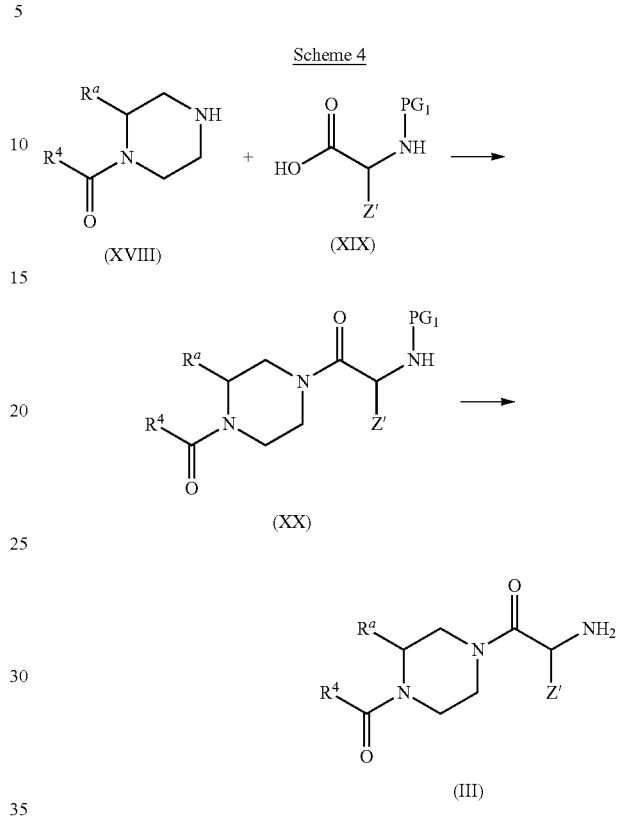

A compound of formula XVIII can be coupled with the acid derivative of formula XIX (wherein $PG_1$ is a suitable protecting group for an amine function like Boc and Z' is hydrogen, $(C_1-C_4)$alkyl, cyclopropyl, cyclopropylmethyl, hydroxy-$(C_1-C_3)$alkyl, $(C_1-C_4)$alkoxycarbonyl-$(C_1-C_3)$alkyl, cyano-$(C_1-C_3)$alkyl, benzyl or $P(O)(R^6)_2$—$(C_1-C_3)$alkyl ($R^6$=ethoxy)) using standard peptide coupling reagents such as HOBT, EDCI, optionally in the presence of DMAP, optionally in the presence of a base such as DIPEA, in a suitable solvent such as DCM or a mixture of DCM and THF, at a temperature around RT. The resulting intermediate of formula XX can then be deprotected using standard methods such as TFA in DCM (see e.g. "Protective groups in organic synthesis", Greene T. W. and Wuts P. G. M., Wiley-Interscience, 1999) to yield the compound of formula III.

Preparation of the Compounds of Formula XVIII

The compounds of formula XVIII, if not commercially available, can be prepared using the route described in WO06114774, general preparation routes, preparation of the compounds of formula V, Scheme 5.

Preparation of the Compounds of Formula XIX

If not commercially available, these compounds can be prepared according to standard methods by the skilled artisan from commercially available compounds.

The compounds of formula XIX wherein Z' is $P(O)(R^6)_2$-methyl, $R^6$ being $(C_1-C_4)$alkoxy and preferably ethoxy, can be prepared using the route summarized in Scheme 5a hereafter.

Scheme 5a

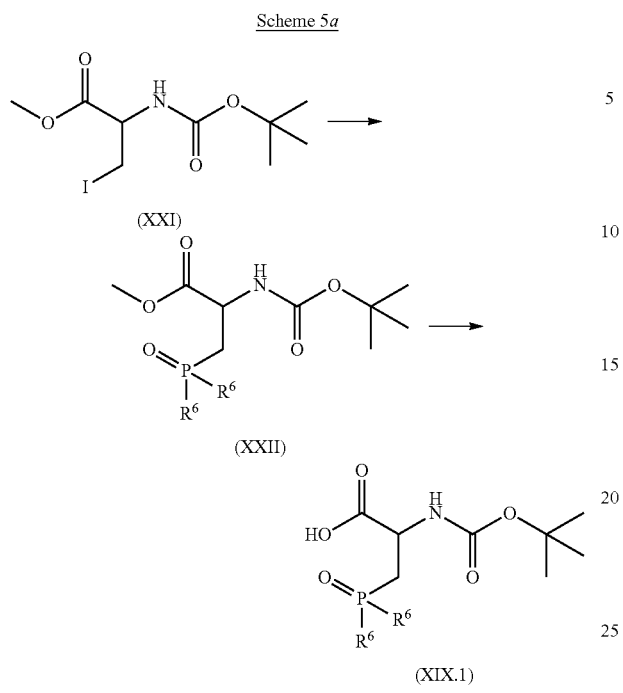

The compounds of formula XIX.1 can be obtained in two steps starting from commercially available Boc-3-iodo-Ala-OMe XXI in an Arbuzov reaction e.g. using P(R⁶)₃, R⁶ being (C₁-C₄)alkoxy and preferably ethyl, at reflux to give compounds XXII followed by a saponification reaction using standard basic conditions such as those already described for Scheme 1 to give compounds of formula XIX.1.

The compounds of formula XIX wherein Z' is 2-[P(O)(R⁶)₂]-ethyl, R⁶ being (C₁-C₄)alkoxy and preferably ethoxy, can be prepared using the route summarized in Scheme 5b hereafter.

Scheme 5b

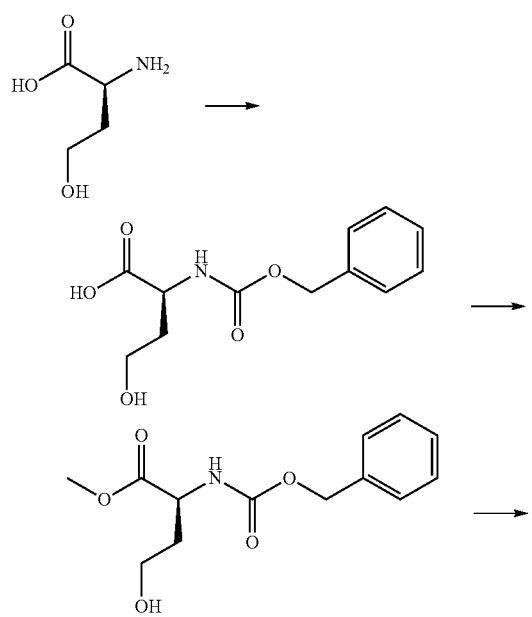

Homoserine is first protected on the nitrogen with a Cbz group using standard conditions known to one skilled in the art (eg. Cbz-Cl, aq. NaOH in dioxane). The dicyclohexylamine salt of the obtained molecule is prepared and the methyl ester is formed using MeI in DMF at a temperature around RT. The hydroxy function is then substituted by a bromide using standard conditions such as PPh₃ and CBr₄, in a suitable solvent such as CH₂Cl₂, preferably between 0° C. and RT. The next two steps are performed using conditions such as those already described for the synthesis of the compounds of formula XIX.1 (see Scheme 5a).

The compounds of formula XIX wherein Z' is 3-[P(O)(R⁶)₂]-propyl, R⁶ being (C₁-C₄)alkoxy and preferably ethoxy, can be prepared using the route summarized in Scheme 5c hereafter.

Scheme 5c

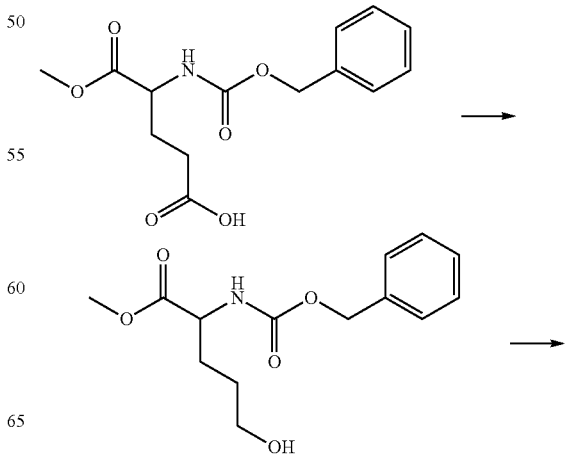

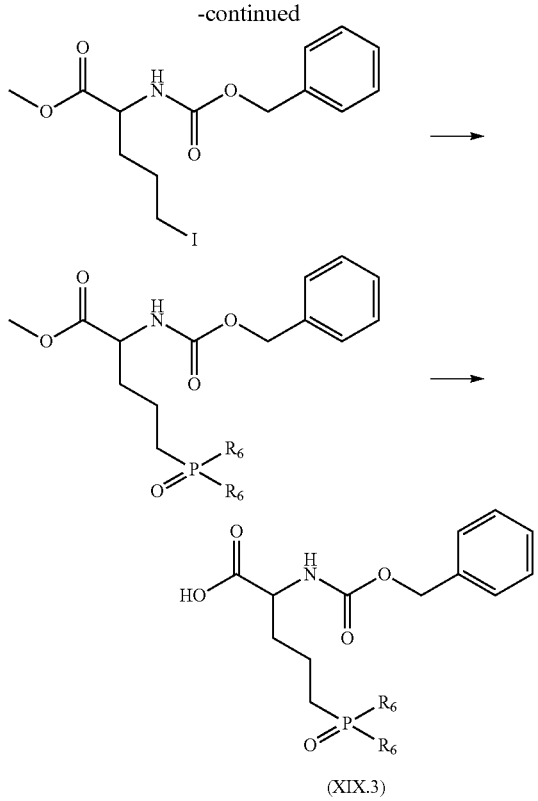

(XIX.3)

The hydroxy compound can be obtained by forming a mixed anhydride on the acid function of Cbz-Glu-OMe using a chloroformate reagent, in the presence of a suitable base such as N-methylmorpholine, in a suitable solvent such as THF, and preferably at about −15° C. The mixed anhydride is reduced by using a suitable reducing agent such as $NaBH_4$ in presence of MeOH, at a temperature around −15° C. The hydroxy function can then be substituted by an iodide using standard conditions such as imidazole, $PPh_3$ and $I_2$, in a suitable solvent such as THF, preferably between 0° C. and RT. The next two steps can be performed using conditions such as those already described for the synthesis of the compounds of formula XIX.1 (see Scheme 5a).

EXAMPLES

Characterization Methods Used:

The LC-MS retention times have been obtained using the following elution conditions:

A X-terra column (MS C18 5 μm, 4.6×50 mm) was used. The two elution solvents were as follows: solvent A=water+0.06% formic acid; solvent B=acetonitrile+0.06% formic acid. The eluent flow rate was 3 ml/min and the characteristics of the eluting mixture proportion in function of the time t from start of the elution are summarized in the table below (a linear gradient being used between two consecutive time points):

| t (min)      | 0  | 1  | 1.25 | 1.30 | 1.75 |
|--------------|----|----|------|------|------|
| Solvent A (%) | 95 | 5  | 5    | 95   | 95   |
| Solvent B (%) | 5  | 95 | 95   | 5    | 5    |

Preparative LC-MS Methods Used:

The purifications by preparative LC-MS have been performed using the conditions described hereafter.

If not indicated otherwise the following conditions are used: A Zorbax® column (PrepHT SB.Aq 5 mm, 21.2×50 mm) was used. The two elution solvents were as follows: solvent A=water+0.2% formic acid; solvent B=acetonitrile+0.2% formic acid. The eluent flow rate was 95 ml/min and the characteristics of the eluting mixture proportion in function of the time t from start of the elution are summarized in the tables below (a linear gradient being used between two consecutive time points):

I) Preparative LC-MS (I):

| t (min)      | 0    | 0.6  | 3.3  | 3.9  | 4.5 | 5.1 | 5.2  | 6    |
|--------------|------|------|------|------|-----|-----|------|------|
| Solvent A (%) | 89.5 | 89.5 | 68.5 | 68.5 | 0   | 0   | 89.5 | 89.5 |
| Solvent B (%) | 10.5 | 10.5 | 31.5 | 31.5 | 100 | 100 | 10.5 | 10.5 |

II) Preparative LC-MS (II):

| t (min)      | 0  | 0.6 | 3.3 | 3.9 | 4.5 | 5.1 | 5.2 | 6  |
|--------------|----|-----|-----|-----|-----|-----|-----|-----|
| Solvent A (%) | 79 | 79  | 58  | 58  | 0   | 0   | 79  | 79 |
| Solvent B (%) | 21 | 21  | 42  | 42  | 100 | 100 | 21  | 21 |

III) Preparative LC-MS (III):

| t (min)      | 0    | 0.6  | 3.3  | 3.9  | 4.5 | 5.1 | 5.2  | 6    |
|--------------|------|------|------|------|-----|-----|------|------|
| Solvent A (%) | 68.5 | 68.5 | 42   | 42   | 0   | 0   | 68.5 | 68.5 |
| Solvent B (%) | 31.5 | 31.5 | 58   | 58   | 100 | 100 | 31.5 | 31.5 |

IV) Preparative LC-MS (IV):

| t (min)      | 0  | 0.6 | 3.3  | 3.9  | 4.5 | 5.1 | 5.2 | 6  |
|--------------|----|-----|------|------|-----|-----|-----|-----|
| Solvent A (%) | 58 | 58  | 31.6 | 31.6 | 0   | 0   | 58  | 58 |
| Solvent B (%) | 42 | 42  | 68.4 | 68.4 | 100 | 100 | 42  | 42 |

V) Preparative LC-MS (V):

| t (min)      | 0  | 0.6 | 3.3 | 3.9 | 4.5 | 5.1 | 5.2 | 6  |
|--------------|----|-----|-----|-----|-----|-----|-----|-----|
| Solvent A (%) | 42 | 42  | 21  | 21  | 0   | 0   | 42  | 42 |
| Solvent B (%) | 58 | 58  | 79  | 79  | 100 | 100 | 58  | 58 |

VI) Preparative LC-MS (VI):

Phenomenex® column (Luna C18 10 u 22.5×5 cm); eluent: solvent $A=H_2O+0.5\%$ $HCO_2H$; solvent $B=CH_3CN+0.5\%$ $HCO_2H$; flow: 50 mL/min;

| t (min)      | 0   | 1.0 | 3.6 | 4.1 | 4.8 | 5.1 | 5.3 |
|--------------|-----|-----|-----|-----|-----|-----|-----|
| Solvent A (%) | 100 | 100 | 60  | 5   | 5   | 100 | 100 |
| Solvent B (%) | 0   | 0   | 40  | 95  | 95  | 0   | 0   |

In the following examples, intermediate A refers to 6-chloro-2-phenyl-pyrimidine-4-carboxylic acid, prepared as described in WO06114774, Example 24, intermediate 24.3.

Example 1

(1α,5α,6α)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid 1.1. (1α,5α,6α)-3-Aza-bicyclo[3.1.0]hexane-3,6-dicarboxylic acid 3-benzyl ester 6-ethyl ester A solution of ethyl diazoacetate (31 mL) in dichloroethane (240 mL) was added slowly (over 5 h) to a mixture of benzyl 3-pyrroline-1-carboxylate (10.6 mL) and rhodium(II)acetate (141 mg) in dichloroethane (120 mL) heated to 80° C. The solvent was evaporated off and the residue was taken up in Hept/EA 1/1 and filtered through neutral alumina. The filtrate was evaporated off and the residue was purified by CC (Hept/EA 3/1 to 2/1) to afford 4.63 g of the desired exo isomer (1α,5α,6α)-3-aza-bicyclo[3.1.0]hexane-3,6-dicarboxylic acid 3-benzyl ester 6-ethyl ester as well as 3.11 g of the endo isomer (1α,5α,6β)-3-aza-bicyclo[3.1.0]hexane-3,6-dicarboxylic acid 3-benzyl ester 6-ethyl ester. LC-MS: (Exo isomer) $t_R$=1.00 min; [M+H]$^+$: 290.30.

1.2. (1α,5α,6α)-3-Aza-bicyclo[3.1.0]hexane-6-carboxylic acid ethyl ester

Intermediate 1.1 (200 mg) was hydrogenated in EtOH (3 ml) with Pd/C (wet, 5%, 80 mg) for 7 h. The mixture was filtered through celite and evaporated off. HV drying afforded 100 mg of the desired compound as orange oil.
LC-MS: $t_R$=0.35 min; [M+H]$^+$: 156.25.
$^1$H-NMR (CDCl$_3$): 4.13 (q, 2H); 3.09 (d, 2H); 2.98 (d, 2H); 2.03 (s, 2H); 1.46 (s, 1H); 1.28 (t, 3H).

1.3. 4-benzyl-piperazine-1-carboxylic acid butyl ester

To a solution of 1-benzyl-piperazine (1.97 ml) and NEt$_3$ (1.9 ml) in DCM (100 ml) was added n-butyl chloroformate (1.47 ml). The mixture was stirred at RT for 2 h. Water was added, the org. phase separated, dried (Na$_2$SO$_4$) and evaporated off to give 3.13 g of a yellow oil.
LC-MS: $t_R$=0.73 min; [M+H]$^+$: 277.42.

1.4. Piperazine-1-carboxylic acid butyl ester

This compound was prepared using a method analogous to that of Example 1, step 1.2, intermediate 1.3 replacing intermediate 1.1.
LC-MS: $t_R$=0.54 min; [M+H+MeCN]$^+$: 226.39.

1.5. 4-((S)-2-benzyloxycarbonylamino-4-tert-butoxycarbonyl-butyryl)-piperazine-1-carboxylic acid butyl ester Cbz-(L)Glu(OtBu)-OH (10 g), HOBT hydrate (5 g), EDCI hydrochloride (6.3 g), intermediate 1.4 (6 g) and DIPEA (10 mL) were dissolved in DCM/THF (1/1, 84 mL). The mixture was stirred at RT for 1 h. DCM and an aq. NaHCO$_3$ solution were added to the mixture and the phases were separated. The org. phase was washed with a 1M NaHSO$_4$ solution, dried (Na$_2$SO$_4$) and evaporated off. CC of the crude (EA/Hept 1/2) offered 13.8 g of the desired compound.
LC-MS: $t_R$=1.04 min; [M+H]$^+$: 506.49.

1.6. 4-((S)-2-amino-4-tert-butoxycarbonyl-butyryl)-piperazine-1-carboxylic acid butyl ester acetic acid salt This compound was prepared using a method analogous to that of Example 1, step 1.2, intermediate 1.5 replacing intermediate 1.1 and using EtOH/AcOH (100/1) instead of EtOH.
LC-MS: $t_R$=0.75 min; [M+H]$^+$: 372.49.

1.7. 4-{(S)-4-tert-butoxycarbonyl-2-[(6-chloro-2-phenyl-pyrimidine-4-carbonyl)-amino]-butyryl}-piperazine-1-carboxylic acid butyl ester A solution of Intermediate A (630 mg) and PyBOP (1.54 g) in DCM (20 ml) was allowed to stir at RT for 10 min. Intermediate 1.6 (1 g) and DIPEA (0.55 mL) were added. The mixture was stirred for 3 h at RT. An aq. NaHCO$_3$ solution was added and the org. phase was further washed with H$_2$O, dried (Na$_2$SO$_4$) and evaporated off. CC (EA/Hept 8/92 to 66/34) of the crude offered 970 mg of the desired compound.
LC-MS: $t_R$=1.18 min; [M+H]$^+$: 588.16.

1.8. (1α,5α,6α)-3-{6-[(S)-3-tert-Butoxycarbonyl-1-(4-butoxycarbonyl-piperazine-1-carbonyl)-propylcarbamoyl]-2-phenyl-pyrimidin-4-yl}-3-aza-bicyclo[3.1.0]hexane-6-carboxylic acid ethyl ester To a solution of intermediate 1.7 (150 mg) in THF (2 mL) were added intermediate 1.2 (47 mg) and DIPEA (96 μL). The resulting mixture was stirred at 60° C. until complete conversion. Water and DCM were added and the phases were separated. The aq. phases were washed with DCM and the combined org. phases were dried (Na$_2$SO$_4$) and evaporated off to afford 202 mg of the desired compound as yellow foam.
LC-MS: $t_R$=1.19 min; [M+H]$^+$: 707.25.

1.9. (1α,5α,6α)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid A solution of intermediate 1.8 (100 mg) in EtOH (0.6 mL) was treated with a solution of lithium hydroxide (LiOH.H$_2$O, 24 mg in H$_2$O/MeOH 0.2 mL/0.5 mL). After stirring overnight at RT, the mixture was concentrated and H$_2$O and Et$_2$O were added. The aq. phase was acidified (1M HCl solution) and extracted with Et$_2$O. The resulting org. phase was dried (Na$_2$SO$_4$) and evaporated off. CC (EA/MeOH 9/1 to 1/1) of the crude afforded 41 mg of the desired compound as beige powder.
LC-MS: $t_R$=0.97 min; [M+H]$^+$: 623.21.

Example 2

(1α,5α,6β)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid 2.1. (1α,5α,6β)-3-Aza-bicyclo[3.1.0]hexane-3,6-dicarboxylic acid 3-benzyl ester 6-ethyl ester The compound was obtained together with intermediate 1.1 as described in Example 1, step 1.1.
LC-MS: (Endo isomer) $t_R$=0.97 min; [M+H]$^+$: 290.32.

2.2. (1α,5α,6β)-3-Aza-bicyclo[3.1.0]hexane-6-carboxylic acid ethyl ester

This compound was prepared using a method analogous to that of Example 1, step 1.2, intermediate 2.1 replacing intermediate 1.1.
$^1$H-NMR (CDCl$_3$): 4.15 (q, 2H); 3.26 (d, 2H); 3.12 (d, 2H); 1.92 (d, 2H); 1.70 (t, 1H); 1.30 (t, 3H).

2.3. (1α,5α,6β)-3-{6-[(S)-3-tert-Butoxycarbonyl-1-(4-butoxycarbonyl-piperazine-1-carbonyl)-propyl-carbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 2.2 replacing intermediate 1.2.
LC-MS: $t_R$=1.13 min; [M+H]$^+$: 707.33.

2.4. (1α,5α,6β)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 2.3 replacing intermediate 1.8.
LC-MS: $t_R$=0.97 min; [M+H]$^+$: 623.25.

Example 3

(1α,5α,6α)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid ethyl ester To a solution of intermediate 1.8 (87 mg) in DCM (3 mL) was added TFA (0.47 mL). The reaction mixture was stirred at RT for 4 h and the solvents were evaporated off. CC (EA/MeOH 9/1) afforded 81 mg of the desired compound as orange foam.
LC-MS: $t_R$=1.07 min; [M+H]$^+$: 651.31.

Example 4

(1α,5α,6β)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid ethyl ester This compound was prepared using a method analogous to that of Example 3, intermediate 2.3 replacing intermediate 1.8.
LC-MS: $t_R$=1.05 min; [M+H]$^+$: 651.33.

Example 5

4-((S)-2-{[6-((1α,5α,6α)-6-tert-Butoxycarbonylamino-3-aza-bicyclo[3.1.0]hex-3-yl)-2-phenyl-pyrimidine-4-carbonyl]amino}-4-carboxy-butyryl)-piperazine-1-carboxylic acid butyl ester

5.1. (1α,5α,6α)-3-Aza-bicyclo[3.1.0]hexane-3,6-dicarboxylic acid 3-benzyl ester This compound was prepared using a method analogous to that of Example 1, step 1.9, intermediate 1.1 replacing intermediate 1.8.
LC-MS: $t_R$=0.85 min; [M+H]$^+$: 262.27.

5.2. (1α,5α,6α)-6-tert-Butoxycarbonylamino-3-aza-bicyclo[3.1.0]hexane-3-carboxylic acid benzyl ester To a solution of intermediate 5.1 (198 mg) in toluene (5 mL) were added TEA (0.211 mL), diphenylphosphoryl azide (0.164 mL) and tert-butanol (0.711 mL). The reaction mixture was stirred at RT for 1 h and was refluxed overnight. The mixture was concentrated off and the residue was purified by CC (EA/Hept 1/2) to afford 79 mg of the desired compound as orange oil.
LC-MS: $t_R$=0.96 min; [M+H]$^+$: 333.14.

5.3. (1α,5α,6α)-(3-Aza-bicyclo[3.1.0]hex-6-yl)-carbamic acid tert-butyl ester This compound was prepared using a method analogous to that of Example 1, step 1.2, intermediate 5.2 replacing intermediate 1.1.
LC-MS: $t_R$=0.57 min; [M+H]$^+$: 199.57.

5.4. 4-((S)-4-tert-Butoxycarbonyl-2-{[6-((1α,5α,6α)-6-tert-butoxycarbonylamino-3-aza-bicyclo[3.1.0]hex-3-yl)-2-phenyl-pyrimidine-4-carbonyl]-amino}-butyryl)-piperazine-1-carboxylic acid butyl ester This compound was prepared using a method analogous to that of Example 1, step 1.8, intermediate 5.3 replacing intermediate 1.2.
LC-MS: $t_R$=1.18 min; [M+H]$^+$: 750.37.

5.5. 4-((S)-2-{[6-((1α,5α,6α)-6-tert-Butoxycarbonylamino-3-aza-bicyclo[3.1.0]hex-3-yl)-2-phenyl-pyrimidine-4-carbonyl]-amino}-4-carboxy-butyryl)-piperazine-1-carboxylic acid butyl ester This compound was prepared using a method analogous to that of Example 1, step 1.9, intermediate 5.4 replacing intermediate 1.8.
LC-MS: $t_R$=1.06 min; [M+H]$^+$: 694.13.

Example 6

4-((S)-2-{[6-((1α,5α,6β)-6-tert-Butoxycarbonylamino-3-aza-bicyclo[3.1.0]hex-3-yl)-2-phenyl-pyrimidine-4-carbonyl]-amino}-4-carboxy-butyryl)-piperazine-1-carboxylic acid butyl ester

6.1. (1α,5α,6β)-3-Aza-bicyclo[3.1.0]hexane-3,6-dicarboxylic acid 3-benzyl ester This compound was prepared using a method analogous to that of Example 1, step 1.9, intermediate 2.1 replacing intermediate 1.8.
LC-MS: $t_R$=0.84 min; [M+H]$^+$: 262.33.

6.2. (1α,5α,6β)-6-tert-Butoxycarbonylamino-3-aza-bicyclo[3.1.0]hexane-3-carboxylic acid benzyl ester This compound was prepared using a method analogous to that of Example 5, step 5.2, intermediate 6.1 replacing intermediate 5.1.
LC-MS: $t_R$=0.98 min; [M+H]$^+$: 333.29.

6.3. (1α,5α,6β)-(3-Aza-bicyclo[3.1.0]hex-6-yl)-carbamic acid tert-butyl ester This compound was prepared using a method analogous to that of Example 1, step 1.2, intermediate 6.2 replacing intermediate 1.1.
LC-MS: $t_R$=0.55 min; [M+H]$^+$: 199.56.

6.4. 4-((S)-4-tert-Butoxycarbonyl-2-{[6-((1α,5α,6β)-6-tert-butoxycarbonylamino-3-aza-bicyclo[3.1.0]hex-3-yl)-2-phenyl-pyrimidine-4-carbonyl]-amino}-butyryl)-piperazine-1-carboxylic acid butyl ester This compound was prepared using a method analogous to that of Example 1, step 1.8, intermediate 6.3 replacing intermediate 1.2.
LC-MS: $t_R$=1.16 min; [M+H]$^+$: 750.38.

6.5. 4-((S)-2-{[6-((1α,5α,6β)-6-tert-Butoxycarbonylamino-3-aza-bicyclo[3.1.0]hex-3-yl)-2-phenyl-pyrimidine-4-carbonyl]-amino}-4-carboxy-butyryl)-piperazine-1-carboxylic acid butyl ester This compound was prepared using a method analogous to that of Example 1, step 1.9, intermediate 6.4 replacing intermediate 1.8.
LC-MS: $t_R$=1.04 min; [M+H]$^+$: 694.15.

Example 7

4-((S)-2-{[6-(1α,5α,6α)-6-Amino-3-aza-bicyclo[3.1.0]hex-3-yl)-2-phenyl-pyrimidine-4-carbonyl]-amino}-4-carboxy-butyryl)-piperazine-1-carboxylic acid butyl ester This compound was prepared using a method analogous to that of Example 3, intermediate 5.4 replacing intermediate 1.8.
LC-MS: $t_R$=0.83 min; [M+H]$^+$: 594.23.

Example 8

4-((S)-2-{[6-((1α,5α,6β)-6-Amino-3-aza-bicyclo[3.1.0]hex-3-yl)-2-phenyl-pyrimidine-4-carbonyl]-amino}-4-carboxy-butyryl)-piperazine-1-carboxylic acid butyl ester This compound was prepared using a method analogous to that of Example 3, intermediate 6.4 replacing intermediate 1.8.
LC-MS: $t_R$=0.84 min; [M+H]$^+$: 594.23.

Example 9

4-((S)-4-Carboxy-2-{[6-((1α,5α,6α)-6-hydroxymethyl-3-aza-bicyclo[3.1.0]hex-3-yl)-2-phenyl-pyrimidine-4-carbonyl]-amino}-butyryl)-piperazine-1-carboxylic acid butyl ester

9.1. (1α,5α,6α)-6-Hydroxymethyl-3-aza-bicyclo[3.1.0]hexane-3-carboxylic acid benzyl ester A solution of intermediate 1.1 (400 mg) in DCM (20 mL) was cooled to −10° C. A 1M solution of DIBAL in DCM (5.5 mL) was added dropwise and the reaction mixture was allowed to warm to RT over 2 h. Aq. NaHCO$_3$ was added and the phases were separated. The org. phase was washed with diluted NaOH solution. The aq. phases were extracted back with DCM and EA. The org. phases were combined, dried (MgSO$_4$) and evaporated off to afford 309 mg of the desired compound as orange oil.
LC-MS: $t_R$=0.83 min; [M+H]$^+$: 248.34.

9.2. (1α,5α,6α)-6-(tert-Butyl-dimethyl-silanyloxymethyl)-3-aza-bicyclo[3.1.0]hexane-3-carboxylic acid benzyl ester To a solution of intermediate 9.1 (150 mg) in DCM (2 mL) was added TBDMSCl (100 mg) and imidazole (41 mg). The reaction mixture was stirred at RT for 3 h, further TBDMSCl (45 mg) and imidazole (20 mg) were added and the reaction mixture was stirred for another 2 h. Water was added and the phases were separated. The org. phase was washed with aq. NH$_4$Cl solution, dried (MgSO$_4$) and evaporated off to afford 222 mg of the desired compound as orange oil.
LC-MS: $t_R$=1.18 min; [M+H]$^+$: 362.19.

9.3. (1α,5α,6α)-6-(tert-Butyl-dimethyl-silanyloxymethyl)-3-aza-bicyclo[3.1.0]hexane This compound was prepared using a method analogous to that of Example 1, step 1.2, intermediate 9.2 replacing intermediate 1.1.
LC-MS: $t_R$=0.75 min; [M+H]$^+$: 228.15.

9.4. 4-[(S)-4-tert-Butoxycarbonyl-2-({6-[(1α,5α,6α)-6-(tert-butyl-dimethyl-silanyloxymethyl)-3-aza-bicyclo[3.1.0]hex-3-yl]-2-phenyl-pyrimidine-4-carbonyl}-amino)-butyryl]-piperazine-1-carboxylic acid butyl ester This compound was prepared using a method analogous to that of Example 1, step 1.8, intermediate 9.3 replacing intermediate 1.2.
LC-MS: $t_R$=1.30 min; [M+H]$^+$: 779.26.

9.5. 4-((S)-4-Carboxy-2-{[6-((1α,5α,6α)-6-hydroxymethyl-3-aza-bicyclo[3.1.0]hex-3-yl)-2-phenyl-pyrimidine-4-carbonyl]-amino}-butyryl)-piperazine-1-carboxylic acid butyl ester This compound was prepared using a method analogous to that of Example 3, intermediate 9.4 replacing intermediate 1.8.
LC-MS: $t_R$=0.96 min; [M+H]$^+$: 609.34.

Example 10

4-((S)-4-Carboxy-2-{[6-((1α,5α,6α)-6-methoxymethyl-3-aza-bicyclo[3.1.0]hex-3-yl)-2-phenyl-pyrimidine-4-carbonyl]-amino}-butyryl)-piperazine-1-carboxylic acid butyl ester

10.1 (1α,5α,6α)-6-Methoxymethyl-3-aza-bicyclo[3.1.0]hexane-3-carboxylic acid benzyl ester To an ice-cold solution of intermediate 9.1 (150 mg) in THF (4.5 mL) was added NaH (60% in mineral oil, 72 mg), followed by MeI (0.114 mL). The reaction mixture was allowed to warm to RT and was stirred at RT for 48 h. Water and EA were added and the phases were separated. The org. phase was washed with water, dried (MgSO$_4$) and evaporated off. The crude was purified by preparative TLC (EA/Hept 1/1) to afford 128 mg of the desired compound as orange oil.
LC-MS: $t_R$=0.91 min; [M+H]$^+$: 262.11.

10.2 (1α,5α,6α)-6-Methoxymethyl-3-aza-bicyclo[3.1.0]hexane

This compound was prepared using a method analogous to that of Example 1, step 1.2, intermediate 10.1 replacing intermediate 1.1.
$^1$H-NMR (CDCl$_3$): 3.33 (s, 3H); 2.99 (d, 2H); 2.82 (d, 2H); 1.42 (s, 2H); 1.31 (s, 1H); 1.00-0.87 (m, 3H).

10.3. 4-((S)-4-tert-Butoxycarbonyl-2-{[6-((1α,5α,6α)-6-methoxymethyl-3-aza-bicyclo[3.1.0]hex-3-yl)-2-phenyl-pyrimidine-4-carbonyl]-amino}-butyryl)-piperazine-1-carboxylic acid butyl ester This compound was prepared using a method analogous to that of Example 1, step 1.8, intermediate 10.2 replacing intermediate 1.2. The compound was purified by CC (EA).
LC-MS: $t_R$=1.18 min; [M+H]$^+$: 679.32.

10.4. 4-((S)-4-Carboxy-2-{[6-((1α,5α,6α)-6-methoxymethyl-3-aza-bicyclo[3.1.0]hex-3-yl)-2-phenyl-pyrimidine-4-carbonyl]-amino}-butyryl)-piperazine-1-carboxylic acid butyl ester This compound was prepared using a method analogous to that of Example 3, intermediate 10.3 replacing intermediate 1.8.
LC-MS: $t_R$=1.04 min; [M+H]$^+$: 623.28.

Example 11

(1α,5α,6β)-3-{6-[(S)-1-(4-Butoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid 11.1. 4-((S)-2-tert-Butoxycarbonylamino-3-methyl-butyryl)-piperazine-1-carboxylic acid butyl ester To a solution of Boc-(L)-Val-OH (400 mg) in DCM (12 mL) were added DIPEA (0.991 mL), DMAP (22 mg), HOBT hydrate (298 mg), EDCI hydrochloride (423 mg) and intermediate 1.4 (343 mg). The mixture was stirred at RT for 6 h. An aq. NaHCO$_3$ solution was added to the mixture and the phases were separated. The org. phase was washed with brine, dried (MgSO$_4$) and evaporated off to afford 844 mg of the desired compound as beige oil.
LC-MS: $t_R$=1.02 min; [M+H]$^+$: 386.42.

11.2. 4-((S)-2-Amino-3-methyl-butyryl)-piperazine-1-carboxylic acid butyl ester trifluoroacetate salt This compound was prepared using a method analogous to that of Example 3, intermediate 11.1 replacing intermediate 1.8.
LC-MS: $t_R$=0.71 min; [M+H]$^+$: 286.25.

11.3. 4-((S)-2-{[6-(Benzotriazol-1-yloxy)-2-phenyl-pyrimidine-4-carbonyl]-amino}-3-methyl-butyryl)-piperazine-1-carboxylic acid butyl ester This compound was prepared using a method analogous to that of Example 1, step 1.7, intermediate 11.2 replacing intermediate 1.6. The compound was however purified by CC (Hept/EA 1/1).
LC-MS: $t_R$=1.16 min; [M+H]$^+$: 601.07.

11.4. (1α,5α,6β)-3-{6-[(S)-1-(4-Butoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 11.3 replacing intermediate 1.7 and intermediate 2.2 replacing intermediate 1.2. The compound was however purified by CC (Hept/EA 1/1).
LC-MS: $t_R$=1.11 min; [M+H]$^+$: 621.29.

11.5. (1α,5α,6β)-3-{6-[(S)-1-(4-Butoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 11.4 replacing intermediate 1.8. The compound was however purified by CC (EA/MeOH 9/1).
LC-MS: $t_R$=1.07 min; [M+H]$^+$: 593.05.

Example 12

(1α,5α,6α)-3-{6-[(S)-1-(4-Butoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid 12.1. (1α,5α,6α)-3-{6-[(S)-1-(4-Butoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 11.4 replacing intermediate 1.7. The compound was however purified by CC (Hept/EA 1/1 to EA).
LC-MS: $t_R$=1.17 min; [M+H]$^+$: 621.11.

12.2. (1α,5α,6α)-3-{6-[(S)-1-(4-Butoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 12.1 replacing intermediate 1.8.
LC-MS: $t_R$=1.07 min; [M+H]$^+$: 593.11.

Example 13

(1α,5α,6β)-3-{6-[(S)-1-(4-Ethoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid 13.1. 4-((S)-2-tert-Butoxycarbonylamino-3-methyl-butyryl)-piperazine-1-carboxylic acid benzyl ester To a solution of Boc-(L)-Val-OH (2 g) in DCM (5 mL) was added DIPEA (4.7 mL) and HATU (5.2 g). After stirring at RT for 10 min, a solution of piperazine-1-carboxylic acid benzyl ester in DCM (5 mL) was added and the resulting reaction mixture was stirred at RT for 2 h. Water was added and the phases were separated. The org. phase was washed with brine, dried (MgSO$_4$) and evaporated off to give 9.3 g of the desired compound as beige oil.

LC-MS: $t_R$=1.03 min; [M+H]$^+$: 419.93.

13.2. 4-((S)-2-Amino-3-methyl-butyryl)-piperazine-1-carboxylic acid benzyl ester This compound was prepared using a method analogous to that of Example 3, intermediate 13.1 replacing intermediate 1.8.

LC-MS: $t_R$=0.74 min; [M+H]$^+$: 319.26.

13.3. 4-{(S)-2-[(6-Chloro-2-phenyl-pyrimidine-4-carbonyl)-amino]-3-methyl-butyryl}-piperazine-1-carboxylic acid benzyl ester This compound was prepared using a method analogous to that of Example 1, step 1.7, intermediate 13.2 replacing intermediate 1.6. The compound was however purified by CC (Hept/EA 7/3).

LC-MS: $t_R$=1.16 min; [M+H]$^+$: 535.96.

13.4. (1α,5α,6β)-3-{6-[(S)-1-(4-Benzyloxycarbonyl-piperazine-1-carbonyl)-2-methyl-propylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 13.3 replacing intermediate 1.7 and intermediate 2.2 replacing intermediate 1.2.

LC-MS: $t_R$=1.16 min; [M+H]$^+$: 655.06.

13.5. (1α,5α,6β)-3-{6-[(S)-2-Methyl-1-(piperazine-1-carbonyl)-propylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.2, intermediate 13.4 replacing intermediate 1.1.

LC-MS: $t_R$=0.88 min; [M+H]$^+$: 521.07.

13.6. (1α,5α,6β)-3-{6-[(S)-1-(4-Ethoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid ethyl ester To an ice-cold solution of intermediate 13.5 (147 mg) and NEt$_3$ (47 μL) in DCM (3 mL) was added ethylchloroformate (27 μL). The reaction mixture was allowed to warm to RT and was stirred at RT for 1 h. Water was added, the org. phase separated, washed with water, dried (Na$_2$SO$_4$) and evaporated off. The crude was purified by CC (Hept/EA 1/1) to give 89 mg of colorless oil.

LC-MS: $t_R$=1.10 min; [M+H]$^+$: 592.98.

13.7. (1α,5α,6β)-3-{6-[(S)-1-(4-Ethoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 13.6 replacing intermediate 1.8.

LC-MS: $t_R$=1.01 min; [M+H]$^+$: 565.03.

Example 14

(1α,5α,6β)-3-{6-[(S)-2-Methyl-1-(4-propoxycarbonyl-piperazine-1-carbonyl)-propylcarbamoyl]-2-phenyl-pyrimidin-4-yl}-3-aza-bicyclo[3.1.0]hexane-6-carboxylic acid

14.1. (1α,5α,6β)-3-{6-[(S)-2-Methyl-1-(4-propoxycarbonyl-piperazine-1-carbonyl)-propylcarbamoyl]-2-phenyl-pyrimidin-4-yl}-3-aza-bicyclo[3.1.0]hexane-6-carboxylic acid ethyl ester This compound was prepared using a method analogous to that of Example 13, step 13.6, propylchloroformate replacing ethylchloroformate.

LC-MS: $t_R$=1.13 min; [M+H]$^+$: 606.90.

14.2. (1α,5α,6β)-3-{6-[(S)-2-Methyl-1-(4-propoxycarbonyl-piperazine-1-carbonyl)-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 14.1 replacing intermediate 1.8. The compound was however purified by preparative LC-MS (IV).

LC-MS: $t_R$=1.04 min; [M+H]$^+$: 578.98.

Example 15

(1α,5α,6β)-3-{6-[(S)-2-Methyl-1-(4-pentyloxycarbonyl-piperazine-1-carbonyl)-propylcarbamoyl]-2-phenyl-pyrimidin-4-yl}-3-aza-bicyclo[3.1.0]hexane-6-carboxylic acid

15.1. (1α,5α,6β)-3-{6-[(S)-2-Methyl-1-(4-pentyloxycarbonyl-piperazine-1-carbonyl)-propylcarbamoyl]-2-phenyl-pyrimidin-4-yl}-3-aza-bicyclo[3.1.0]hexane-6-carboxylic acid ethyl ester This compound was prepared using a method analogous to that of Example 13, step 13.6, pentylchloroformate replacing ethylchloroformate.

LC-MS: $t_R$=1.18 min; [M+H]$^+$: 635.03.

15.2. (1α,5α,6β)-3-{6-[(S)-2-Methyl-1-(4-pentyloxycarbonyl-piperazine-1-carbonyl)-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 15.1 replacing intermediate 1.8.

LC-MS: $t_R$=1.10 min; [M+H]$^+$: 606.85.

Example 16

(1α,5α,6β)-3-{6-[(S)-1-(4-Hexyloxycarbonyl-piperazine-1-carbonyl)-2-methyl-propylcarbamoyl]-2-phenyl-pyrimidin-4-yl}-3-aza-bicyclo[3.1.0]hexane-6-carboxylic acid

16.1. (1α,5α,6β)-3-{6-[(S)-1-(4-Hexyloxycarbonyl-piperazine-1-carbonyl)-2-methyl-propylcarbamoyl]-2-phenyl-pyrimidin-4-yl}-3-aza-bicyclo[3.1.0]hexane-6-carboxylic acid ethyl ester This compound was prepared using a method analogous to that of Example 13, step 13.6, hexylchloroformate replacing ethylchloroformate.

LC-MS: $t_R$=1.21 min; [M+H]$^+$: 649.07.

16.2. (1α,5α,6β)-3-{6-[(S)-1-(4-Hexyloxycarbonyl-piperazine-1-carbonyl)-2-methyl-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 16.1 replacing intermediate 1.8. The compound was however purified by preparative LC-MS (II).

LC-MS: $t_R$=1.13 min; [M+H]$^+$: 621.03.

Example 17

4-((S)-2-{[6-((1α,5α,6α)-6-Carbamoyl-3-aza-bicyclo[3.1.0]hex-3-yl)-2-phenyl-pyrimidine-4-carbonyl]-amino}-3-methyl-butyryl)-piperazine-1-carboxylic acid butyl ester

17.1. (1α,5α,6α)-6-Carbamoyl-3-aza-bicyclo[3.1.0]hexane-3-carboxylic acid benzyl ester To a −15° C. cooled solution of intermediate 5.1 (840 mg) in THF (40 mL) was added NMM (0.39 mL) followed by isobutylchloroformate (0.46 mL) dropwise. The reaction mixture was stirred at −15° C. for 20 min NH$_4$OH (25% in H$_2$O, 0.48 mL) was added, the mixture was allowed to warm to RT and stirred at RT for 2 h. NH$_4$OH (25% in water, 0.24 mL) was added and the mixture was stirred at RT for 1 h. Aq. 1M KHSO$_4$ was added and the mixture was extracted with EA. The org. phases were washed with water, dried (Na$_2$SO$_4$) and evaporated off to afford 662 mg of the desired compound as beige solid.

LC-MS: $t_R$=0.81 min; [M+H]$^+$: 261.10.

17.2. (1α,5α,6α)-3-Aza-bicyclo[3.1.0]hexane-6-carboxylic acid amide

This compound was prepared using a method analogous to that of Example 1, step 1.2, intermediate 17.1 replacing intermediate 1.1.

LC-MS: $t_R$=0.19 min; [M+H]$^+$: 127.48.

17.3. 4-((S)-2-{[6-((1α,5α,6α)-6-Carbamoyl-3-aza-bicyclo[3.1.0]hex-3-yl)-2-phenyl-pyrimidine-4-carbonyl]-amino}-3-methyl-butyryl)-piperazine-1-carboxylic acid butyl ester This compound was prepared using a method analogous to that of Example 1, step 1.8, intermediate 11.3 replacing intermediate 1.7 and intermediate 17.2 replacing intermediate 1.2. The compound was however purified by CC (Hept/EA 1/2 followed by EA/MeOH 1/1).

LC-MS: $t_R$=1.07 min; [M+H]$^+$: 592.04.

Example 18

4-((S)-2-{[6-((1α,5α,6α)-6-Cyano-3-aza-bicyclo[3.1.0]hex-3-yl)-2-phenyl-pyrimidine-4-carbonyl]-amino}-3-methyl-butyryl)-piperazine-1-carboxylic acid butyl ester To a solution of intermediate 17.3 (256 mg) in DCM (12.5 mL) was added Burgess reagent (361 mg). The reaction mixture was stirred at RT for 2 h 30 and was concentrated under vacuum. The residue was purified by CC (Hept/EA 1/5). The obtained impure compound was taken up in EA, washed with water, sat. NH$_4$Cl and sat. NaHCO$_3$, dried (Na$_2$SO$_4$) and evaporated off. The residue was again purified by CC (Hept/EA 1/5) to afford 218 mg of the desired compound as white solid.

LC-MS: $t_R$=1.13 min; [M+H]$^+$: 574.10.

Example 19

4-[(S)-3-Methyl-2-({2-phenyl-6-[1α,5α,6α)-6-(1H-tetrazol-5-yl)-3-aza-bicyclo[3.1.0]hex-3-yl]-pyrimidine-4-carbonyl}-amino)-butyryl]-piperazine-1-carboxylic acid butyl ester To compound of Example 18 (110 mg) was added NaN$_3$ (13.7 mg) followed by ZnBr$_2$ (43 mg) and water (0.8 mL). The reaction mixture was stirred at 110° C. in a microwave oven overnight. NaN$_3$ (7 mg) followed by ZnBr$_2$ (21 mg) were added and the mixture was further heated at 110° C. overnight. The mixture was acidified and EA was added. The phases were separated and the aq. phase was washed with EA. The combined org. phases were dried (MgSO$_4$) and evaporated off. CC of the crude (Ea/MeOH 9/1) afforded 88 mg of the desired compound as white solid.

LC-MS: $t_R$=1.08 min; [M+H]$^+$: 617.08.

Example 20

4-((S)-2-{[6-((1α,5α,6β)-6-Carbamoyl-3-aza-bicyclo[3.1.0]hex-3-yl)-2-phenyl-pyrimidine-4-carbonyl]-amino}-3-methyl-butyryl)-piperazine-1-carboxylic acid butyl ester

20.1. (1α,5α,6β)-6-Carbamoyl-3-aza-bicyclo[3.1.0]hexane-3-carboxylic acid benzyl ester This compound was prepared using a method analogous to that of Example 17, step 17.1, intermediate 6.1 replacing intermediate 5.1.

LC-MS: $t_R$=0.74 min; [M+H]$^+$: 261.13.

20.2. (1α,5α,6β)-3-Aza-bicyclo[3.1.0]hexane-6-carboxylic acid amide

This compound was prepared using a method analogous to that of Example 1, step 1.2, intermediate 20.1 replacing intermediate 1.1.

LC-MS: $t_R$=0.19 min; [M+H]$^+$: 127.47.

20.3. 4-((S)-2-{[6-((1α,5α,6β)-6-Carbamoyl-3-aza-bicyclo[3.1.0]hex-3-yl)-2-phenyl-pyrimidine-4-carbonyl]-amino}-3-methyl-butyryl)-piperazine-1-carboxylic acid butyl ester This compound was prepared using a method analogous to that of Example 17, step 17.3, intermediate 20.2 replacing intermediate 17.2. The compound was however purified by CC (EA/MeOH 9/1 performed twice).

LC-MS: $t_R$=1.02 min; [M+H]$^+$: 592.02.

Example 21

4-((S)-2-{[6-((1α,5α,6β)-6-Cyano-3-aza-bicyclo[3.1.0]hex-3-yl)-2-phenyl-pyrimidine-4-carbonyl]-amino}-3-methyl-butyryl)-piperazine-1-carboxylic acid butyl ester This compound was prepared using a method analogous to that of Example 18, intermediate 20.3 replacing intermediate 17.3.

LC-MS: $t_R$=1.11 min; [M+H]$^+$: 574.01.

Example 22

4-[(S)-3-Methyl-2-({2-phenyl-6-[1α,5α,6β]-6-(1H-tetrazol-5-yl)-3-aza-bicyclo[3.1.0]hex-3-yl]-pyrimidine-4-carbonyl}-amino)-butyryl]-piperazine-1-carboxylic acid butyl ester

This compound was prepared using a method analogous to that of Example 19, compound of Example 21 replacing compound of Example 18.
LC-MS: $t_R$=1.03 min; [M+H]⁺: 617.09.

Example 23

4-((S)-2-{[6-((1α,5α,6β)-6-Amino-3-aza-bicyclo[3.1.0]hex-3-yl)-2-phenyl-pyrimidine-4-carbonyl]-amino}-3-methyl-butyryl)-piperazine-1-carboxylic acid butyl ester

23.1. 4-{(S)-2-[(6-Chloro-2-phenyl-pyrimidine-4-carbonyl)-amino]-3-methyl-butyryl}-piperazine-1-carboxylic acid butyl ester This compound was obtained together with intermediate 11.3 by performing the reaction described in Example 11, step 11.3.
LC-MS: $t_R$=1.16 min; [M+H]⁺: 502.05.

23.2. 4-((S)-2-{[6-((1α,5α,6β)-6-tert-Butoxycarbonylamino-3-aza-bicyclo[3.1.0]hex-3-yl)-2-phenyl-pyrimidine-4-carbonyl]-amino}-3-methyl-butyryl)-piperazine-1-carboxylic acid butyl ester This compound was prepared using a method analogous to that of Example 1, step 1.8, intermediate 23.1 replacing intermediate 1.7 and intermediate 6.3 replacing intermediate 1.2. The compound was purified by CC (Hept/EA 1/1 to EA).
LC-MS: $t_R$=1.15 min; [M+H]⁺: 64.10.

23.3. 4-((S)-2-{[6-((1α,5α,6β)-6-Amino-3-aza-bicyclo[3.1.0]hex-3-yl)-2-phenyl-pyrimidine-4-carbonyl]-amino}-3-methyl-butyryl)-piperazine-1-carboxylic acid butyl ester This compound was prepared using a method analogous to that of Example 3, intermediate 23.2 replacing intermediate 1.8. The compound was however purified by CC (EA to EA/MeOH 1/1).
LC-MS: $t_R$=0.91 min; [M+H]⁺: 564.09.

Example 24

4-((S)-2-{[6-((1α,5α,6α)-6-Carboxymethyl-3-aza-bicyclo[3.1.0]hex-3-yl)-2-phenyl-pyrimidine-4-carbonyl]-amino}-3-methyl-butyryl)-piperazine-1-carboxylic acid butyl ester

24.1. (1α,5α,6α)-6-Hydroxymethyl-3-aza-bicyclo[3.1.0]hexane-3-carboxylic acid benzyl ester To a −25° C. cooled solution of intermediate 1.1 (3 g) in DCM (150 mL) was added dropwise a solution of DIBAL (1M in THF, 42 mL). The reaction mixture was stirred at −25° C. for 10 min. Sat. aq. NaHCO₃ was added and the org. phase was washed with water. The aq. phases were extracted with DCM and EA, the combined org. phases were dried (MgSO₄) and evaporated off to afford 1.28 g of the desired compound as orange oil.
LC-MS: $t_R$=0.79 min; [M+H]⁺: 248.06.

24.2. (1α,5α,6α)-6-Formyl-3-aza-bicyclo[3.1.0]hexane-3-carboxylic acid benzyl ester DMP (15% in DCM, 20 mL) was added to a solution of intermediate 24.1 (1.27 g) in DCM (20 mL) at RT. After stirring for 2 h 40 at RT, sat. aq. NaHCO₃ was added and the phases were separated. The org. phase was dried (MgSO₄) and evaporated off. CC (Hept/EA 12/88 to EA) of the crude afforded 620 mg of the desired compound as orange oil.
LC-MS: $t_R$=0.86 min; [M+H]⁺: 246.04.

24.3. (1α,5α,6α)-6-(2-Methoxy-vinyl)-3-aza-bicyclo[3.1.0]hexane-3-carboxylic acid benzyl ester To a −78° C. cooled solution of (methoxymethyl)-triphenylphosphoniumchloride (1.81 g) in THF (5 mL) was added sodium bis(trimethylsilyl)amide (1.07 g). The reaction mixture was stirred at −78° C. for 1 h and a solution of intermediate 24.2 (260 mg) in THF (0.3 mL) was added. The reaction mixture was stirred at −78° C. for 30 min and at RT for 1 h. EA and water were added, the org. phase was dried (MgSO₄) and evaporated off. CC (Hept/EA 1/1) of the crude afforded 249 mg of the desired compound as orange oil.
LC-MS: $t_R$=1.04 min; [M+H]⁺: 274.12.

24.4. (1α,5α,6α)-6-(2-Oxo-ethyl)-3-aza-bicyclo[3.1.0]hexane-3-carboxylic acid benzyl ester A solution of HCl (25% in water, 2.2 mL) was added to a solution of intermediate 24.3 (172 mg) in acetone (4.4 mL). After 5 min stirring, the mixture was poured into sat. aq. NaHCO₃ and extracted with EA. The org. phase was dried (MgSO₄) and evaporated off to afford 159 mg of the desired compound as orange oil.
LC-MS: $t_R$=0.91 min; [M+H]⁺: 260.12.

24.5. (1α,5α,6α)-6-Carboxymethyl-3-aza-bicyclo[3.1.0]hexane-3-carboxylic acid benzyl ester To a ice-cooled solution of intermediate 24.4 (155 mg) in tBuOH (12.5 mL) and 2-methyl-2-butene (0.632 mL) was added NaClO₂ (81 mg). The ice bath was removed, the reaction mixture was stirred at RT overnight and was evaporated off. The residue was taken up in water/DCM. The phases were separated, the aq. phase was acidified with aq. HCl 25% and extracted with DCM. The combined org. phases were dried (MgSO₄) and evaporated off to afford 185 mg of the desired compound as orange oil.
LC-MS: $t_R$=0.87 min; [M+H]⁺: 276.12.

24.6. (1α,5α,6α)-6-Ethoxycarbonylmethyl-3-aza-bicyclo[3.1.0]hexane-3-carboxylic acid benzyl ester To a solution of intermediate 24.5 (180 mg) in DCM (6 mL) was added EtOH (0.114 mL), DMAP (80 mg) and DCC (135 mg). The reaction mixture was stirred at RT overnight. Water was added and the mixture was extracted with DCM. The combined org. phases were dried (MgSO₄) and evaporated off to afford 364 mg of the desired compound as orange solid.
LC-MS: $t_R$=1.01 min; [M+H]⁺: 304.16.

24.7. (1α,5α,6α)-(3-Aza-bicyclo[3.1.0]hex-6-yl)-acetic acid ethyl ester

This compound was prepared using a method analogous to that of Example 1, step 1.2, intermediate 24.6 replacing intermediate 1.1.
LC-MS: $t_R$=0.45 min; [M+H]$^+$: 170.15.

24.8. 4-((S)-2-{[6-((1α,5α,6α)-6-Ethoxycarbonylmethyl-3-aza-bicyclo[3.1.0]hex-3-yl)-2-phenyl-pyrimidine-4-carbonyl]-amino}-3-methyl-butyryl)-piperazine-1-carboxylic acid butyl ester This compound was prepared using a method analogous to that of Example 1, step 1.8, intermediate 24.7 replacing intermediate 1.2 and intermediate 11.3 replacing intermediate 1.7. The compound was purified by CC (Hept/EA 1/2).
LC-MS: $t_R$=1.18 min; [M+H]$^+$: 635.11.

24.9. 4-((S)-2-{[6-((1α,5α,6α)-6-Carboxymethyl-3-aza-bicyclo[3.1.0]hex-3-yl)-2-phenyl-pyrimidine-4-carbonyl]-amino}-3-methyl-butyryl)-piperazine-1-carboxylic acid butyl ester This compound was prepared using a method analogous to that of Example 1, step 1.9, intermediate 24.8 replacing intermediate 1.8.
LC-MS: $t_R$=1.08 min; [M+H]$^+$: 606.94.

Example 25

4-((S)-2-{[6-((1α,5α,6β)-6-Carboxymethyl-3-aza-bicyclo[3.1.0]hex-3-yl)-2-phenyl-pyrimidine-4-carbonyl]-amino}-3-methyl-butyryl)-piperazine-1-carboxylic acid butyl ester

25.1. (1α,5α,6β)-6-Hydroxymethyl-3-aza-bicyclo[3.1.0]hexane-3-carboxylic acid benzyl ester This compound was prepared using a method analogous to that of Example 24, step 24.1, intermediate 1.2 replacing intermediate 1.1.
LC-MS: $t_R$=0.78 min; [M+H]$^+$: 248.06.

25.2. (1α,5α,6β)-6-Formyl-3-aza-bicyclo[3.1.0]hexane-3-carboxylic acid benzyl ester This compound was prepared using a method analogous to that of Example 24, step 24.2, intermediate 25.1 replacing intermediate 24.1.
LC-MS: $t_R$=0.84 min; [M+H]$^+$: 246.03.

25.3. (1α,5α,6β)-6-(2-Methoxy-vinyl)-3-aza-bicyclo[3.1.0]hexane-3-carboxylic acid benzyl ester This compound was prepared using a method analogous to that of Example 24, step 24.3, intermediate 25.2 replacing intermediate 24.2.
LC-MS: $t_R$=1.02 min; [M+H]$^+$: 274.15.

25.4. (1α,5α,6β)-6-(2-Oxo-ethyl)-3-aza-bicyclo[3.1.0]hexane-3-carboxylic acid benzyl ester This compound was prepared using a method analogous to that of Example 24, step 24.4, intermediate 25.3 replacing intermediate 24.3.
LC-MS: $t_R$=0.91 min; [M+H]$^+$: 260.13.

25.5. (1α,5α,6β)-6-Carboxymethyl-3-aza-bicyclo[3.1.0]hexane-3-carboxylic acid benzyl ester This compound was prepared using a method analogous to that of Example 24, step 24.5, intermediate 25.4 replacing intermediate 24.4.
LC-MS: $t_R$=0.87 min; [M+H]$^+$: 276.17.

25.6. (1α,5α,6β)-6-Ethoxycarbonylmethyl-3-aza-bicyclo[3.1.0]hexane-3-carboxylic acid benzyl ester This compound was prepared using a method analogous to that of Example 24, step 24.6, intermediate 25.5 replacing intermediate 24.5.
LC-MS: $t_R$=1.02 min; [M+H]$^+$: 304.16.

25.7. (1α,5α,6β)-(3-Aza-bicyclo[3.1.0]hex-6-yl)-acetic acid ethyl ester

This compound was prepared using a method analogous to that of Example 24, step 24.7, intermediate 25.6 replacing intermediate 24.6.
LC-MS: $t_R$=0.47 min; [M+H]$^+$: 170.12.

25.8. 4-((S)-2-{[6-((1α,5α,6β)-6-Ethoxycarbonylmethyl-3-aza-bicyclo[3.1.0]hex-3-yl)-2-phenyl-pyrimidine-4-carbonyl]-amino}-3-methyl-butyryl)-piperazine-1-carboxylic acid butyl ester This compound was prepared using a method analogous to that of Example 1, step 1.8, intermediate 25.7 replacing intermediate 1.2 and intermediate 11.3 replacing intermediate 1.7. The compound was purified by CC (Hept/EA 1/2).
LC-MS: $t_R$=1.18 min; [M+H]$^+$: 635.11.

25.9. 4-((S)-2-{[6-((1α,5α,6β)-6-Carboxymethyl-3-aza-bicyclo[3.1.0]hex-3-yl)-2-phenyl-pyrimidine-4-carbonyl]-amino}-3-methyl-butyryl)-piperazine-1-carboxylic acid butyl ester This compound was prepared using a method analogous to that of Example 24, step 24.9, intermediate 25.8 replacing intermediate 24.8.
LC-MS: $t_R$=1.09 min; [M+H]$^+$: 606.81.

Example 26

4-[(S)-2-({6-[(1α,5α,6β)-6-(2-Carboxy-ethyl)-3-aza-bicyclo[3.1.0]hex-3-yl]-2-phenyl-pyrimidine-4-carbonyl}-amino)-3-methyl-butyryl]-piperazine-1-carboxylic acid butyl ester

26.1. (1α,5α,6β)-6-((E)-2-Methoxycarbonyl-vinyl)-3-aza-bicyclo[3.1.0]hexane-3-carboxylic acid benzyl ester A mixture of (methoxycarbonylmethylene)triphenylphosphorane (266 mg) and intermediate 25.2 (65 mg) in dry THF (3 mL) was stirred at 75° C. for 1 h 30. Water/EA were added, the org. phase was dried (MgSO$_4$) and evaporated off. The crude was taken up in Hept/EA 1/1 and filtered through a pad of silica. The filtrate was concentrated under vacuum and purified by CC (Hept/EA 1/1) to afford 43 mg of the desired compound as pale yellow oil.
LC-MS: $t_R$=1.00 min; [M+H]$^+$: 302.10.

26.2. (1α,5α,6β)-3-(3-Aza-bicyclo[3.1.0]hex-6-yl)-propionic acid methyl ester

This compound was prepared using a method analogous to that of Example 1, step 1.2, intermediate 26.1 replacing intermediate 1.1.
LC-MS: $t_R$=0.49 min; [M+H]$^+$: 170.12.

26.3. 4-[(S)-2-({6-[(1α,5α,6β)-6-(2-Methoxycarbonyl-ethyl)-3-aza-bicyclo[3.1.0]hex-3-yl]-2-phenyl-pyrimidine-4-carbonyl}-amino)-3-methyl-butyryl]-piperazine-1-carboxylic acid butyl ester This compound was prepared using a method analogous to that of Example 1, step 1.8, intermediate 26.2 replacing intermediate 1.2 and intermediate 11.3 replacing intermediate 1.7. The compound was purified by CC (Hept/EA 1/1 to 1/2 followed by Hept/EA 1/2).
LC-MS: $t_R$=1.18 min; [M+H]$^+$: 635.02.

26.4. 4-[(S)-2-({6-[(1α,5α,6β)-6-(2-Carboxy-ethyl)-3-aza-bicyclo[3.1.0]hex-3-yl]-2-phenyl-pyrimidine-4-carbonyl}-amino)-3-methyl-butyryl]-piperazine-1-carboxylic acid butyl ester This compound was prepared using a method analogous to that of Example 1, step 1.9, intermediate 26.3 replacing intermediate 1.8.
LC-MS: $t_R$=1.11 min; [M+H]$^+$: 621.03.

Example 27

4-[(S)-2-({6-[(1α,5α,6α)-6-(2-Carboxy-ethyl)-3-aza-bicyclo[3.1.0]hex-3-yl]-2-phenyl-pyrimidine-4-carbonyl}-amino)-3-methyl-butyryl]-piperazine-1-carboxylic acid butyl ester 27.1. (1α,5α,6α)-6-((E)-2-Methoxycarbonyl-vinyl)-3-aza-bicyclo[3.1.0]hexane-3-carboxylic acid benzyl ester This compound was prepared using a method analogous to that of Example 26, step 26.1, intermediate 24.2 replacing intermediate 25.2. The compound was purified by CC (Hept/EA 12/88 to EA).
LC-MS: $t_R$=1.01 min; [M+H]$^+$: 302.09.

27.2. (1α,5α,6α)-3-(3-Aza-bicyclo[3.1.0]hex-6-yl)-propionic acid methyl ester

This compound was prepared using a method analogous to that of Example 1, step 1.2, intermediate 27.1 replacing intermediate 1.1.
LC-MS: $t_R$=0.49 min; [M+H]$^+$: 170.12.

27.3. 4-[(S)-2-({6-[(1α,5α,6α)-6-(2-Methoxycarbonyl-ethyl)-3-aza-bicyclo[3.1.0]hex-3-yl]-2-phenyl-pyrimidine-4-carbonyl}-amino)-3-methyl-butyryl]-piperazine-1-carboxylic acid butyl ester This compound was prepared using a method analogous to that of Example 1, step 1.8, intermediate 27.2 replacing intermediate 1.2 and intermediate 11.3 replacing intermediate 1.7. The compound was purified by CC (Hept/EA 1/1 to 1/2)
LC-MS: $t_R$=1.19 min; [M+H]$^+$: 635.09. .

27.4. 4-[(S)-2-({6-[(1α,5α,6α)-6-(2-Carboxy-ethyl)-3-aza-bicyclo[3.1.0]hex-3-yl]-2-phenyl-pyrimidine-4-carbonyl}-amino)-3-methyl-butyryl]-piperazine-1-carboxylic acid butyl ester This compound was prepared using a method analogous to that of Example 1, step 1.9, intermediate 27.3 replacing intermediate 1.8. The compound was however purified by CC (EA/MeOH 9/1).
LC-MS: $t_R$=1.11 min; [M+H]$^+$: 621.02.

Example 28

(1α,5α,6β)-3-[6-[(S)-1-(4-Butoxycarbonyl-piperazine-1-carbonyl)-2-methyl-propylcarbamoyl]-2-(4-fluoro-phenyl)-pyrimidin-4-yl]-3-aza-bicyclo[3.1.0] hexane-6-carboxylic acid 28.1. 4-fluoro-benzamidine To an ice-cold solution of hexamethyldisilazane (7 mL) in Et$_2$O (40 mL) was added n-BuLi (1.6M in hexanes, 20.6 mL), followed by a solution of 4-fluorobenzonitrile (2 g) in Et$_2$O (10 ml). After stirring at 0° C. for 10 min, the mixture was allowed to warm to RT and was stirred at RT for 20 h. The mixture was acidified to pH 1 by adding a 1M HCl solution and was washed with CHCl$_3$. The aq. layer was then basified to pH 14 by adding Na$_2$CO$_3$ and NaOH and was extracted twice with CHCl$_3$. The org. layers were dried (Na$_2$SO$_4$) and evaporated off to afford the desired compound (1.59 g).
LC-MS: $t_R$=0.33 min; [M+H]$^+$: 139.21.

28.2. 6-chloro-2-(4-fluoro-phenyl)-pyrimidine-4-carboxylic acid

This compound was prepared in 4 steps from intermediate 28.1 using methods analog to those described in WO 2006/114774 (see Example 1, step 1.3 and Example 24, steps 24.1, 24.2 and 24.3).
LC-MS: $t_R$=0.90 min; [M+H]$^+$: 253.24.

28.3. 4-((S)-2-{[6-Chloro-2-(4-fluoro-phenyl)-pyrimidine-4-carbonyl]-amino}-3-methyl-butyryl)-piperazine-1-carboxylic acid butyl ester This compound was prepared using a method analogous to that of Example 1, step 1.7, intermediate 28.2 replacing intermediate A and intermediate 11.2 replacing intermediate 1.6. The compound was purified by CC (Hept/EA 7/3 to EA).
LC-MS: $t_R$=1.17 min; [M+H]$^+$: 519.95.

28.4. (1α,5α,6β)-3-[6-[(S)-1-(4-Butoxycarbonyl-piperazine-1-carbonyl)-2-methyl-propylcarbamoyl]-2-(4-fluoro-phenyl)-pyrimidin-4-yl]-3-aza-bicyclo[3.1.0]hexane-6-carboxylic acid ethyl ester This compound was prepared using a method analogous to that of Example 1, step 1.8, intermediate 28.3 replacing intermediate 1.7 and intermediate 2.2 replacing intermediate 1.2. The compound was purified by CC (Hept/EA 4/6 to EA)
LC-MS: $t_R$=1.17 min; [M+H]$^+$: 639.51. .

28.5. (1α,5α,6β)-3-[6-[(S)-1-(4-Butoxycarbonyl-piperazine-1-carbonyl)-2-methyl-propylcarbamoyl]-2-(4-fluoro-phenyl)-pyrimidin-4-yl]-3-aza-bicyclo[3.1.0]hexane-6-carboxylic acid Intermediate 28.4 (252 mg) was dissolved in EtOH (1 mL) and 1M NaOH (1 mL). The reaction mixture was stirred at RT for 24 h, acidified with 1M HCl to pH 6 and extracted with EA. The org. phase was washed with brine, dried (MgSO$_4$) and evaporated off to afford 173 mg of the desired product as white powder.

LC-MS: $t_R$=1.09 min; [M+H]$^+$: 610.97.

Example 29

(1α,5α,6β)-3-{6-[(S)-1-(4-Butoxycarbonyl-piperazine-1-carbonyl)-2-methyl-propylcarbamoyl]-2-p-tolyl-pyrimidin-4-yl}-3-aza-bicyclo[3.1.0]hexane-6-carboxylic acid

29.1. 6-chloro-2-p-tolyl-pyrimidine-4-carboxylic acid

This compound was prepared in 4 steps from 4-methylbenzamidine using methods analog to those described in WO 2006/114774 (see Example 1, step 1.3, Example 24, steps 24.1, 24.2 and 24.3).

LC-MS: $t_R$=0.93 min; [M+H]$^+$: 249.28.

29.2. 4-{(S)-2-[(6-Chloro-2-p-tolyl-pyrimidine-4-carbonyl)-amino]-3-methyl-butyryl}-piperazine-1-carboxylic acid butyl ester This compound was prepared using a method analogous to that of Example 1, step 1.7, intermediate 29.1 replacing intermediate A and intermediate 11.2 replacing intermediate 1.6. The compound was purified by CC (Hept/EA 7/3 to EA).

LC-MS: $t_R$=1.19 min; [M+H]$^+$: 515.89.

29.3. (1α,5α,6β)-3-{6-[(S)-1-(4-Butoxycarbonyl-piperazine-1-carbonyl)-2-methyl-propylcarbamoyl]-2-p-tolyl-pyrimidin-4-yl}-3-aza-bicyclo[3.1.0]hexane-6-carboxylic acid ethyl ester This compound was prepared using a method analogous to that of Example 1, step 1.8, intermediate 29.2 replacing intermediate 1.7 and intermediate 2.2 replacing intermediate 1.2. The compound was purified by CC (Hept/EA 1/1 to EA).

LC-MS: $t_R$=1.17 min; [M+H]$^+$: 635.05.

29.4. (1α,5α,6β)-3-{6-[(S)-1-(4-Butoxycarbonyl-piperazine-1-carbonyl)-2-methyl-propylcarbamoyl]-2-p-tolyl-pyrimidin-4-yl}-3-aza-bicyclo[3.1.0]hexane-6-carboxylic acid This compound was prepared using a method analogous to that of Example 28, step 28.5, intermediate 29.3 replacing intermediate 28.4.

LC-MS: $t_R$=1.09 min; [M+H]$^+$: 607.52.

Example 30

(1α,5α,6β)-3-[6-[(S)-1-(4-Butoxycarbonyl-piperazine-1-carbonyl)-2-methyl-propylcarbamoyl]-2-(3-trifluoromethyl-phenyl)-pyrimidin-4-yl]-3-aza-bicyclo[3.1.0]hexane-6-carboxylic acid

30.1. 6-chloro-2-(3-trifluoromethyl-phenyl)-pyrimidine-4-carboxylic acid

This compound was prepared in 4 steps from 3-trifluoromethylbenzamidine using a method analogous to that described in WO 2006/114774 (see Example 1, step 1.3, Example 24, steps 24.1, 24.2 and 24.3).

LC-MS: $t_R$=1.03 min; [M+H]$^+$: 302.69.

30.2. 4-((S)-2-{[6-Chloro-2-(3-trifluoromethyl-phenyl)-pyrimidine-4-carbonyl]-amino}-3-methyl-butyryl)-piperazine-1-carboxylic acid butyl ester This compound was prepared using a method analogous to that of Example 1, step 1.7, intermediate 30.1 replacing intermediate A and intermediate 11.2 replacing intermediate 1.6. The compound was purified by CC (Hept/EA 7/3 to EA).

LC-MS: $t_R$=1.21 min; [M+H]$^+$: 569.88.

30.3. (1α,5α,6β)-3-[6-[(S)-1-(4-Butoxycarbonyl-piperazine-1-carbonyl)-2-methyl-propylcarbamoyl]-2-(3-trifluoromethyl-phenyl)-pyrimidin-4-yl]-3-aza-bicyclo[3.1.0]hexane-6-carboxylic acid ethyl ester This compound was prepared using a method analogous to that of Example 1, step 1.8, intermediate 30.2 replacing intermediate 1.7 and intermediate 2.2 replacing intermediate 1.2. The compound was purified by CC (Hept/EA 1/1 to EA).

LC-MS: $t_R$=1.21 min; [M+H]$^+$: 689.04.

30.4. (1α,5α,6β)-3-[6-[(S)-1-(4-Butoxycarbonyl-piperazine-1-carbonyl)-2-methyl-propylcarbamoyl]-2-(3-trifluoromethyl-phenyl)-pyrimidin-4-yl]-3-aza-bicyclo[3.1.0]hexane-6-carboxylic acid This compound was prepared using a method analogous to that of Example 28, step 28.5, intermediate 30.3 replacing intermediate 28.4.

LC-MS: $t_R$=1.14 min; [M+H]$^+$: 661.06.

Example 31

(1α,5α,6β)-3-{6-[(S)-1-((R)-4-Butoxycarbonyl-3-methyl-piperazine-1-carbonyl)-2-methyl-propylcarbamoyl]-2-phenyl-pyrimidin-4-yl}-3-aza-bicyclo[3.1.0]hexane-6-carboxylic acid

31.1. (R)-4-((S)-2-tert-Butoxycarbonylamino-3-methyl-butyryl)-2-methyl-piperazine-1-carboxylic acid benzyl ester This compound was prepared using a method analogous to that of Example 13, step 13.1, (R)-2-methyl-piperazine-1-carboxylic acid benzyl ester hydrochloride replacing piperazine-1-carboxylic acid benzyl ester. The compound was purified by CC (Hept/EA 6/4).

LC-MS: $t_R$=1.05 min; [M+H]$^+$: 434.08.

31.2. (R)-4-((S)-2-Amino-3-methyl-butyryl)-2-methyl-piperazine-1-carboxylic acid benzyl ester This compound was prepared using a method analogous to that of Example 3, intermediate 31.1 replacing intermediate 1.8.

LC-MS: $t_R$=0.75 min; [M+H]$^+$: 334.13.

31.3. (R)-4-{(S)-2-[(6-Chloro-2-phenyl-pyrimidine-4-carbonyl)-amino]-3-methyl-butyryl}-2-methyl-piperazine-1-carboxylic acid benzyl ester This compound was prepared using a method analogous to that of Example 13, step 13.1, intermediate 31.2 replacing benzyl 1-piperazinecarboxylate and intermediate A replacing Boc-(L)-Val-OH. The compound was purified by CC (Hept/EA 6/4).

LC-MS: $t_R$=1.17 min; [M+H]$^+$: 549.99.

31.4. (1α,5α,6β)-3-{6-[(S)-1-((R)-4-Benzyloxycarbonyl-3-methyl-piperazine-1-carbonyl)-2-methyl-propylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 31.3 replacing intermediate 1.7 and intermediate 2.2 replacing intermediate 1.2. The compound was purified by CC (Hept/EA 1/1) followed by preparative LC-MS (IV).

LC-MS: $t_R$=1.17 min; [M+H]$^+$: 668.97.

31.5. (1α,5α,6β)-3-{6-[(S)-2-Methyl-1-((R)-3-methyl-piperazine-1-carbonyl)-propylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.2, intermediate 31.4 replacing intermediate 1.1.

LC-MS: $t_R$=0.88 min; [M+H]$^+$: 535.00.

31.6. (1α,5α,6β)-3-{6-[(S)-1-((R)-4-Butoxycarbonyl-3-methyl-piperazine-1-carbonyl)-2-methyl-propylcarbamoyl]-2-phenyl-pyrimidin-4-yl}-3-aza-bicyclo[3.1.0]hexane-6-carboxylic acid ethyl ester This compound was prepared using a method analogous to that of Example 13, step 13.6, butylchloroformate replacing ethylchloroformate and intermediate 31.5 replacing intermediate 13.5. The compound was purified by CC (Hept/EA 1/1).

LC-MS: $t_R$=1.17 min; [M+H]$^+$: 635.05.

31.7. (1α,5α,6β)-3-{6-[(S)-1-((R)-4-Butoxycarbonyl-3-methyl-piperazine-1-carbonyl)-2-methyl-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 31.6 replacing intermediate 1.8. The compound was however purified by preparative LC-MS (IV).

LC-MS: $t_R$=1.08 min; [M+H]$^+$: 606.88.

Example 32

(1α,5α,6β)-3-{6-[(S)-1-((R)-4-Benzyloxycarbonyl-3-methyl-piperazine-1-carbonyl)-2-methyl-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 31.4 replacing intermediate 1.8. The compound was however purified by preparative LC-MS (IV).

LC-MS: $t_R$=1.09 min; [M+H]$^+$: 640.68.

Example 33

(1α,5α,6β)-3-{6-[2-(4-Butoxycarbonyl-piperazin-1-yl)-2-oxo-ethylcarbamoyl]-2-phenyl-pyrimidin-4-yl}-3-aza-bicyclo[3.1.0]hexane-6-carboxylic acid 33.1 4-(2-tert-Butoxycarbonylamino-acetyl)-piperazine-1-carboxylic acid butyl ester To a solution of Boc-Glycine (2351 mg) in DCM (150 mL) were added HOBT hydrate (2358 mg) and EDCI hydrochloride (3100 mg) and the mixture was stirred for 30 min at RT. Intermediate 1.4 (2500 mg) was then added and the reaction mixture was stirred at RT overnight. A 1N NaHSO$_4$ aqueous solution was added to the mixture, the formed solid was filtered off and the 2 phases of the filtrate were separated. The org. phase was washed with sat. Na$_2$CO$_3$ solution, dried (MgSO$_4$) and evaporated off to afford 4620 mg of the desired compound as white solid.

LC-MS: $t_R$=0.92 min; [M+H]$^+$: 344.27.

33.2 4-(2-Amino-acetyl)-piperazine-1-carboxylic acid butyl ester

To a solution of intermediate 33.1 (4620 mg) in DCM (20 mL) was added TFA (20 mL). The reaction mixture was stirred at RT for 2 h and the solvents were evaporated off. The crude was redissolved in DCM (20 mL) and washed with 1N NaOH and brine, dried (MgSO$_4$) and evaporated off to afford 3120 mg of the desired compound as yellowish oil.

LC-MS: $t_R$=0.63 min; [M+H]$^+$: 243.49.

33.3 4-{2-[(6-Chloro-2-phenyl-pyrimidine-4-carbonyl)-amino]-acetyl}-piperazine-1-carboxylic acid butyl ester This compound was prepared using a method analogous to that of Example 1, step 1.7, intermediate 33.2 replacing intermediate 1.6. The compound was purified by CC (Hept/EA 1/1).

LC-MS: $t_R$=1.08 min; [M+H]$^+$: 460.10.

33.4 (1α,5α,6β)-3-Aza-bicyclo[3.1.0]hexane-6-carboxylic acid

This compound was prepared using a method analogous to that of Example 1, step 1.2, intermediate 6.1 replacing intermediate 1.1.

LC-MS: $t_R$=0.20 min; [M+H]$^+$: 128.33.

33.5 (1α,5α,6β)-3-{6-[2-(4-Butoxycarbonyl-piperazin-1-yl)-2-oxo-ethylcarbamoyl]-2-phenyl-pyrimidin-4-yl}-3-aza-bicyclo[3.1.0]hexane-6-carboxylic acid This compound was prepared using a method analogous to that of Example 1, step 1.8, intermediate 33.3 replacing intermediate 1.7 and intermediate 33.4 replacing intermediate 1.2.
LC-MS: $t_R$=1.00 min; [M+H]$^+$: 551.05.

Example 34

(1α,5α,6α)-3-{6-[(S)-2-(4-Butoxycarbonyl-piperazin-1-yl)-1-methyl-2-oxo-ethylcarbamoyl]-2-phenyl-pyrimidin-4-yl}-3-aza-bicyclo[3.1.0]hexane-6-carboxylic acid

34.1 4-((S)-2-tert-Butoxycarbonylamino-propionyl)-piperazine-1-carboxylic acid butyl ester This compound was prepared using a method analogous to that of Example 1, step 1.5, Boc-Ala-OH replacing Cbz-(L)Glu(OtBu)-OH. The compound was however not purified and used as crude.
LC-MS: $t_R$=0.95 min; [M+H]$^+$: 358.19.

34.2 4-((S)-2-Amino-propionyl)-piperazine-1-carboxylic acid butyl ester

This compound was prepared using a method analogous to that of Example 33, step 33.2, intermediate 34.1 replacing intermediate 33.1.
LC-MS: $t_R$=0.66 min; [M+H]$^+$: 258.14.

34.3 4(S)-{2-[(6-Chloro-2-phenyl-pyrimidine-4-carbonyl)-amino]-propionyl}-piperazine-1-carboxylic acid butyl ester This compound was prepared using a method analogous to that of Example 1, step 1.7, intermediate 34.2 replacing intermediate 1.6. The compound was purified by CC (Hept/EA 1/1).
LC-MS: $t_R$=1.12 min; [M+H]$^+$: 474.02.

34.4 (1α,5α,6α)-3-{6-(S)-[2-(4-Butoxycarbonyl-piperazin-1-yl)-1-methyl-2-oxo-ethylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 34.3 replacing intermediate 1.7.
LC-MS: $t_R$=1.15 min; [M+H]$^+$: 592.98.

34.5 (1α,5α,6α)-3-{6-[(S)-2-(4-Butoxycarbonyl-piperazin-1-yl)-1-methyl-2-oxo-ethylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 34.4 replacing intermediate 1.8.
LC-MS: $t_R$=1.03 min; [M+H]$^+$: 564.96.

Example 35

(1α,5α,6β)-3-{6-[(S)-2-(4-Butoxycarbonyl-piperazin-1-yl)-1-methyl-2-oxo-ethylcarbamoyl]-2-phenyl-pyrimidin-4-yl}-3-aza-bicyclo[3.1.0]hexane-6-carboxylic acid

35.1 (1α,5α,6β)-3-{6-[(S)-2-(4-Butoxycarbonyl-piperazin-1-yl)-1-methyl-2-oxo-ethylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 34.3 replacing intermediate 1.7 and intermediate 2.2 replacing intermediate 1.2.
LC-MS: $t_R$=1.11 min; [M+H]$^+$: 593.00.

35.2 (1α,5α,6β)-3-{6-[(S)-2-(4-Butoxycarbonyl-piperazin-1-yl)-1-methyl-2-oxo-ethylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 35.1 replacing intermediate 1.8.
LC-MS: $t_R$=0.98 min; [M+H]$^+$: 565.25.

Example 36

(1α,5α,6β)-3-{6-[(S)-1-(4-Butoxycarbonyl-piperazine-1-carbonyl)-propylcarbamoyl]-2-phenyl-pyrimidin-4-yl}-3-aza-bicyclo[3.1.0]hexane-6-carboxylic acid

36.1 4-(S)-(2-tert-Butoxycarbonylamino-butyryl)-piperazine-1-carboxylic acid butyl ester This compound was prepared using a method analogous to that of Example 1, step 1.5, Boc-Abu-OH replacing Cbz-(L)Glu(OtBu)-OH. The compound was however not purified and used as crude.
LC-MS: $t_R$=0.99 min; [M+H]$^+$: 372.11.

36.2 4-(S)-(2-Amino-butyryl)-piperazine-1-carboxylic acid butyl ester

This compound was prepared using a method analogous to that of Example 33, step 33.2, intermediate 36.1 replacing intermediate 33.1.
LC-MS: $t_R$=0.68 min; [M+H]$^+$: 272.19.

36.3 4-(S)-{2-[(6-Chloro-2-phenyl-pyrimidine-4-carbonyl)-amino]-butyryl}-piperazine-1-carboxylic acid butyl ester A solution of Intermediate A (255 mg), DIPEA (0.28 mL) and HATU (619 mg) in DCM (3 mL) was allowed to stir at RT for 10 min. Intermediate 36.2 (324 mg), dissolved in DCM (2 mL) was then added. The mixture was stirred for 2 h at RT. An aq. NaHCO$_3$ solution was added. The org. phase was washed with water, brine, dried (MgSO$_4$) and evaporated off. CC (Hept/EA 2/1) of the crude afforded 380 mg of the desired compound as beige foam.
LC-MS: $t_R$=1.14 min; [M+H]$^+$: 488.02.

36.4 (1α,5α,6β)-3-{6-[(S)-1-(4-Butoxycarbonyl-piperazine-1-carbonyl)-propylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 36.3 replacing intermediate 1.7 and intermediate 2.2 replacing intermediate 1.2.
LC-MS: $t_R$=1.14 min; [M+H]$^+$: 606.93.

36.5 (1α,5α,6β)-3-{6-[(S)-1-(4-Butoxycarbonyl-piperazine-1-carbonyl)-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 36.4 replacing intermediate 1.8.
LC-MS: $t_R$=1.05 min; [M+H]$^+$: 578.96.

Example 37

(1α,5α,6β)-3-{6-[(S)-1-(4-Butoxycarbonyl-piperazine-1-carbonyl)-butylcarbamoyl]-2-phenyl-pyrimidin-4-yl}-3-aza-bicyclo[3.1.0]hexane-6-carboxylic acid

37.1 4-(S)-(2-tert-Butoxycarbonylamino-pentanoyl)-piperazine-1-carboxylic acid butyl ester This compound was prepared using a method analogous to that of Example 1, step 1.5, Boc-L-norvaline replacing Cbz-(L)Glu(OtBu)-OH. The compound was however not purified and used as crude.
LC-MS: $t_R$=1.02 min; [M+H]$^+$: 386.25.

37.2 4-(S)-(2-Amino-pentanoyl)-piperazine-1-carboxylic acid butyl ester

This compound was prepared using a method analogous to that of Example 33, step 33.2, intermediate 37.1 replacing intermediate 33.1.
LC-MS: $t_R$=0.71 min; [M+H]$^+$: 286.17.

37.3 4-(S)-{2-[(6-Chloro-2-phenyl-pyrimidine-4-carbonyl)-amino]-pentanoyl}-piperazine-1-carboxylic acid butyl ester This compound was prepared using a method analogous to that of Example 36, step 36.3, intermediate 37.2 replacing intermediate 36.2. The compound was purified by CC (Hept/EA 6/4).
LC-MS: $t_R$=1.16 min; [M+H]$^+$: 501.98.

37.4 (1α,5α,6β)-3-{6-[(S)-1-(4-Butoxycarbonyl-piperazine-1-carbonyl)-butylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 37.3 replacing intermediate 1.7 and intermediate 2.2 replacing intermediate 1.2.
LC-MS: $t_R$=1.16 min; [M+H]$^+$: 621.05.

37.5 (1α,5α,6β)-3-{6-[(S)-1-(4-Butoxycarbonyl-piperazine-1-carbonyl)-butylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 37.4 replacing intermediate 1.8.
LC-MS: $t_R$=1.07 min; [M+H]$^+$: 592.99.

Example 38

(1α,5α,6β)-3-{6-[(S)-1-(4-Butoxycarbonyl-piperazine-1-carbonyl)-pentylcarbamoyl]-2-phenyl-pyrimidin-4-yl}-3-aza-bicyclo[3.1.0]hexane-6-carboxylic acid

38.1 4-(S)-(2-tert-Butoxycarbonylamino-hexanoyl)-piperazine-1-carboxylic acid butyl ester This compound was prepared using a method analogous to that of Example 1, step 1.5, Boc-NLe-OH replacing Cbz-(L)Glu(OtBu)-OH. The compound was however not purified and used as crude.
LC-MS: $t_R$=1.06 min; [M+H]$^+$: 400.09.

38.2 4-(S)-(2-Amino-hexanoyl)-piperazine-1-carboxylic acid butyl ester

This compound was prepared using a method analogous to that of Example 33, step 33.2, intermediate 38.1 replacing intermediate 33.1.
LC-MS: $t_R$=0.74 min; [M+H]$^+$: 300.20.

38.3 4-(S)-{2-[(6-Chloro-2-phenyl-pyrimidine-4-carbonyl)-amino]-hexanoyl}-piperazine-1-carboxylic acid butyl ester This compound was prepared using a method analogous to that of Example 36, step 36.3, intermediate 38.2 replacing intermediate 36.2. The compound was purified by CC (Hept/EA 2/1).
LC-MS: $t_R$=1.18 min; [M+H]$^+$: 515.94.

38.4 (1α,5α,6β)-3-{6-(S)-[1-(4-Butoxycarbonyl-piperazine-1-carbonyl)-pentylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 38.3 replacing intermediate 1.7 and intermediate 2.2 replacing intermediate 1.2.
LC-MS: $t_R$=1.18 min; [M+H]$^+$: 635.05.

38.5 (1α,5α,6β)-3-{6-[(S)-1-(4-Butoxycarbonyl-piperazine-1-carbonyl)-pentylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 38.4 replacing intermediate 1.8.
LC-MS: $t_R$=1.10 min; [M+H]$^+$: 606.93.

Example 39

(1α,5α,6β)-3-{6-[(S)-1-(4-Butoxycarbonyl-piperazine-1-carbonyl)-3-methyl-butylcarbamoyl]-2-phenyl-pyrimidin-4-yl}-3-aza-bicyclo[3.1.0]hexane-6-carboxylic acid

39.1 4-((S)-2-tert-Butoxycarbonylamino-4-methyl-pentanoyl)-piperazine-1-carboxylic acid butyl ester This compound was prepared using a method analogous to that of Example 1, step 1.5, Boc-Leu-OH replacing Cbz-(L)Glu(OtBu)-OH. The compound was however not purified and used as crude.
LC-MS: $t_R$=1.05 min; [M+H]$^+$: 400.11.

39.2 4-((S)-2-Amino-4-methyl-pentanoyl)-piperazine-1-carboxylic acid butyl ester This compound was prepared using a method analogous to that of Example 33, step 33.2, intermediate 39.1 replacing intermediate 33.1.
LC-MS: $t_R$=0.74 min; [M+H]$^+$: 300.21.

39.3 4-{(S)-2-[(6-Chloro-2-phenyl-pyrimidine-4-carbonyl)-amino]-4-methyl-pentanoyl}-piperazine-1-carboxylic acid butyl ester This compound was prepared using a method analogous to that of Example 36, step 36.3, intermediate 39.2 replacing intermediate 36.2. The compound was purified by CC (Hept/EA 2/1).
LC-MS: $t_R$=1.18 min; [M+H]$^+$: 515.93.

39.4 (1α,5α,6β)-3-{6-(S)-[1-(4-Butoxycarbonyl-piperazine-1-carbonyl)-3-methyl-butylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 39.3 replacing intermediate 1.7 and intermediate 2.2 replacing intermediate 1.2.
LC-MS: $t_R$=1.17 min; [M+H]$^+$: 635.05.

39.5 (1α,5α,6β)-3-{6-[(S)-1-(4-Butoxycarbonyl-piperazine-1-carbonyl)-3-methyl-butylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 39.4 replacing intermediate 1.8.
LC-MS: $t_R$=1.09 min; [M+H]$^+$: 606.91.

Example 40

(1α,5α,6β)-3-{6-[(S)-2-(4-Butoxycarbonyl-piperazin-1-yl)-1-cyclopropylmethyl-2-oxo-ethylcarbamoyl]-2-phenyl-pyrimidin-4-yl}-3-aza-bicyclo[3.1.0]hexane-6-carboxylic acid

40.1 4-((S)-2-tert-Butoxycarbonylamino-3-cyclopropyl-propionyl)-piperazine-1-carboxylic acid butyl ester This compound was prepared using a method analogous to that of Example 1, step 1.5, Boc-beta-cyclopropyl-Ala-OH replacing Cbz-(L)Glu(OtBu)-OH. The compound was however not purified and used as crude.
LC-MS: $t_R$=1.03 min; [M+H]$^+$: 398.07.

40.2 4-((S)-2-Amino-3-cyclopropyl-propionyl)-piperazine-1-carboxylic acid butyl ester This compound was prepared using a method analogous to that of Example 33, step 33.2, intermediate 40.1 replacing intermediate 33.1.
LC-MS: $t_R$=0.72 min; [M+H]$^+$: 298.17.

40.3 4-{(S)-2-[(6-Chloro-2-phenyl-pyrimidine-4-carbonyl)-amino]-3-cyclopropyl-propionyl}-piperazine-1-carboxylic acid butyl ester This compound was prepared using a method analogous to that of Example 36, step 36.3, intermediate 40.2 replacing intermediate 36.2. The compound was purified by CC (Hept/EA 4/1).
LC-MS: $t_R$=1.14 min; [M+H]$^+$: 514.13.

40.4 (1α,5α,6β)-3-{6-[(S)-2-(4-Butoxycarbonyl-piperazin-1-yl)-1-cyclopropylmethyl-2-oxo-ethylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 40.3 replacing intermediate 1.7 and intermediate 2.2 replacing intermediate 1.2.
LC-MS: $t_R$=1.15 min; [M+H]$^+$: 633.03.

40.5 (1α,5α,6β)-3-{6-[(S)-2-(4-Butoxycarbonyl-piperazin-1-yl)-1-cyclopropylmethyl-2-oxo-ethylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 40.4 replacing intermediate 1.8.
LC-MS: $t_R$=1.07 min; [M+H]$^+$: 604.97.

Example 41

(1α,5α,6β)-3-{6-[(S)-2-(4-Butoxycarbonyl-piperazin-1-yl)-1-cyclopropyl-2-oxo-ethylcarbamoyl]-2-phenyl-pyrimidin-4-yl}-3-aza-bicyclo[3.1.0]hexane-6-carboxylic acid

41.1 4-((S)-2-tert-Butoxycarbonylamino-2-cyclopropyl-acetyl)-piperazine-1-carboxylic acid butyl ester This compound was prepared using a method analogous to that of Example 1, step 1.5, Boc-L-cyclopropylglycine replacing Cbz-(L)Glu(OtBu)-OH. The compound was however not purified and used as crude.
LC-MS: $t_R$=0.99 min; [M+H]$^+$: 384.76.

41.2 4-((S)-2-Amino-2-cyclopropyl-acetyl)-piperazine-1-carboxylic acid butyl ester This compound was prepared using a method analogous to that of Example 33, step 33.2, intermediate 41.1 replacing intermediate 33.1.
LC-MS: $t_R$=0.69 min; [M+H]$^+$: 284.69.

41.3 4-{(S)-2-[(6-Chloro-2-phenyl-pyrimidine-4-carbonyl)-amino]-2-cyclopropyl-acetyl}-piperazine-1-carboxylic acid butyl ester This compound was prepared using a method analogous to that of Example 36, step 36.3, intermediate 41.2 replacing intermediate 36.2. The compound was purified by CC (Hept/EA 7/2).
LC-MS: $t_R$=1.14 min; [M+H]$^+$: 500.02.

41.4 (1α,5α,6β)-3-{6-[(S)-2-(4-Butoxycarbonyl-piperazin-1-yl)-1-cyclopropyl-2-oxo-ethylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 41.3 replacing intermediate 1.7 and intermediate 2.2 replacing intermediate 1.2.
LC-MS: $t_R$=1.14 min; [M+H]$^+$: 619.04.

41.5 (1α,5α,6β)-3-{6-[(S)-2-(4-Butoxycarbonyl-piperazin-1-yl)-1-cyclopropyl-2-oxo-ethylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 41.4 replacing intermediate 1.8.
LC-MS: $t_R$=1.05 min; [M+H]$^+$: 590.99.

Example 42

(1α,5α,6β)-3-{6-[(1S,2R)-1-(4-Butoxycarbonyl-piperazine-1-carbonyl)-2-hydroxy-propylcarbamoyl]-2-phenyl-pyrimidin-4-yl}-3-aza-bicyclo[3.1.0]hexane-6-carboxylic acid

42.1 4-((2S,3R)-2-tert-Butoxycarbonylamino-3-hydroxy-butyryl)-piperazine-1-carboxylic acid butyl ester This compound was prepared using a method analogous to that of Example 1, step 1.5, Boc-Thr-OH replacing Cbz-(L)Glu(OtBu)-OH. The compound was however not purified and used as crude.
LC-MS: $t_R$=0.90 min; [M+H]$^+$: 387.95.

42.2 4-((2S,3R)-2-Amino-3-hydroxy-butyryl)-piperazine-1-carboxylic acid butyl ester This compound was prepared using a method analogous to that of Example 33, step 33.2, intermediate 42.1 replacing intermediate 33.1.
LC-MS: $t_R$=0.65 min; [M+H]$^+$: 288.16.

42.3 4-((2S,3R)-2-{[6-(Benzotriazol-1-yloxy)-2-phenyl-pyrimidine-4-carbonyl]-amino}-3-hydroxy-butyryl)-piperazine-1-carboxylic acid butyl ester This compound was prepared using a method analogous to that of Example 1, step 1.7, intermediate 42.2 replacing intermediate 1.6. The compound was however purified by CC (Hept/EA 1/1 to EA)
LC-MS: $t_R$=1.07 min; [M+H]$^+$: 602.95..

42.4 (1α,5α,6β)-3-{6-[(1S,2R)-1-(4-Butoxycarbonyl-piperazine-1-carbonyl)-2-hydroxy-propylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 42.3 replacing intermediate 1.7 and intermediate 2.2 replacing intermediate 1.2.
LC-MS: $t_R$=1.06 min; [M+H]$^+$: 623.00.

42.5 (1α,5α,6β)-3-{6-[(1S,2R)-1-(4-Butoxycarbonyl-piperazine-1-carbonyl)-2-hydroxy-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 42.4 replacing intermediate 1.8.
LC-MS: $t_R$=0.97 min; [M+H]$^+$: 595.00.

Example 43

(1α,5α,6β)-3-{6-[(S)-1-(4-Butoxycarbonyl-piperazine-1-carbonyl)-2,2-dimethyl-propylcarbamoyl]-2-phenyl-pyrimidin-4-yl}-3-aza-bicyclo[3.1.0]hexane-6-carboxylic acid

43.1 4-((S)-2-tert-Butoxycarbonylamino-3,3-dimethyl-butyryl)-piperazine-1-carboxylic acid butyl ester This compound was prepared using a method analogous to that of Example 1, step 1.5, Boc-L-tert-Leucine replacing Cbz-(L)Glu(OtBu)-OH. The compound was however not purified and used as crude.
LC-MS: $t_R$=1.06 min; [M+H]$^+$: 400.11.

43.2 4-((S)-2-Amino-3,3-dimethyl-butyryl)-piperazine-1-carboxylic acid butyl ester This compound was prepared using a method analogous to that of Example 33, step 33.2, intermediate 43.1 replacing intermediate 33.1.
LC-MS: $t_R$=0.75 min; [M+H]$^+$: 300.15.

43.3 4-((S)-2-{[6-(Benzotriazol-1-yloxy)-2-phenyl-pyrimidine-4-carbonyl]-amino}-3,3-dimethyl-butyryl)-piperazine-1-carboxylic acid butyl ester This compound was prepared using a method analogous to that of Example 1, step 1.7, intermediate 43.2 replacing intermediate 1.6. The compound was purified by CC (Hept/EA 1/1).
LC-MS: $t_R$=1.19 min; [M+H]$^+$: 614.97.

43.4 (1α,5α,6β)-3-{6-[(S)-1-(4-Butoxycarbonyl-piperazine-1-carbonyl)-2,2-dimethyl-propylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 43.3 replacing intermediate 1.7 and intermediate 2.2 replacing intermediate 1.2.
LC-MS: $t_R$=1.18 min; [M+H]$^+$: 635.03.

43.5 (1α,5α,6β)-3-{6-[(S)-1-(4-Butoxycarbonyl-piperazine-1-carbonyl)-2,2-dimethyl-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 43.4 replacing intermediate 1.8.

LC-MS: $t_R$=1.06 min; [M+H]$^+$: 607.30.

Example 44

(1α,5α,6α)-3-{6-[(S)-1-(4-Butoxycarbonyl-piperazine-1-carbonyl)-2,2-dimethyl-propylcarbamoyl]-2-phenyl-pyrimidin-4-yl}-3-aza-bicyclo[3.1.0]hexane-6-carboxylic acid

44.1 (1α,5α,6α)-3-{6-[(S)-1-(4-Butoxycarbonyl-piperazine-1-carbonyl)-2,2-dimethyl-propylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 44.3 replacing intermediate 1.7.

LC-MS: $t_R$=1.20 min; [M+H]$^+$: 635.05.

44.2 (1α,5α,6α)-3-{6-[(S)-1-(4-Butoxycarbonyl-piperazine-1-carbonyl)-2,2-dimethyl-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 44.1 replacing intermediate 1.8.

LC-MS: $t_R$=1.10 min; [M+H]$^+$: 606.91.

Example 45

(1α,5α,6β)-3-{6-[(S)-1-Benzyl-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid

45.1 4-((S)-2-tert-Butoxycarbonylamino-3-phenyl-propionyl)-piperazine-1-carboxylic acid butyl ester This compound was prepared using a method analogous to that of Example 1, step 1.5, Boc-L-Phenylalanine replacing Cbz-(L)Glu(OtBu)-OH. The compound was however not purified and used as crude.

LC-MS: $t_R$=1.06 min; [M+H]$^+$: 434.10.

45.2 4-((S)-2-Amino-3-phenyl-propionyl)-piperazine-1-carboxylic acid butyl ester This compound was prepared using a method analogous to that of Example 33, step 33.2, intermediate 45.1 replacing intermediate 33.1.

LC-MS: $t_R$=0.77 min; [M+H]$^+$: 334.19.

45.3 4-((S)-2-{[6-(Benzotriazol-1-yloxy)-2-phenyl-pyrimidine-4-carbonyl]-amino}-3-phenyl-propionyl)-piperazine-1-carboxylic acid butyl ester This compound was prepared using a method analogous to that of Example 1, step 1.7, intermediate 45.2 replacing intermediate 1.6. The compound was purified by CC (Hept/EA 1/1).

LC-MS: $t_R$=1.18 min; [M+H]$^+$: 648.98.

45.4 (1α,5α,6β)-3-{6-[(S)-1-Benzyl-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 45.3 replacing intermediate 1.7 and intermediate 2.2 replacing intermediate 1.2.

LC-MS: $t_R$=1.17 min; [M+H]$^+$: 669.04.

45.5 (1α,5α,6β)-3-{6-[(S)-1-Benzyl-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 45.4 replacing intermediate 1.8.

LC-MS: $t_R$=1.05 min; [M+H]$^+$: 641.30.

Example 46

(1α,5α,6α)-3-{6-[(S)-1-Benzyl-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid

46.1 (1α,5α,6α)-3-{6-[(S)-1-Benzyl-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 45.3 replacing intermediate 1.7.

LC-MS: $t_R$=1.19 min; [M+H]$^+$: 669.07.

46.2 (1α,5α,6α)-3-{6-[(S)-1-Benzyl-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 46.1 replacing intermediate 1.8.

LC-MS: $t_R$=1.09 min; [M+H]$^+$: 640.59.

Example 47

(1α,5α,6β)-3-[6-[(S)-1-(4-Butoxycarbonyl-piperazine-1-carbonyl)-2-methyl-propylcarbamoyl]-2-(2-fluoro-phenyl)-pyrimidin-4-yl]-3-aza-bicyclo[3.1.0]hexane-6-carboxylic acid

47.1. 6-Chloro-2-(2-fluoro-phenyl)-pyrimidine-4-carboxylic acid

This compound was prepared in 4 steps from 2-fluoro-benzamidine using methods analog to those described in WO 2006/114774 (see Example 1, step 1.3, Example 24, steps 24.1, 24.2 and 24.3)

LC-MS: $t_R$=0.89 min; [M+H]$^+$: 253.08. .

47.2. 4-{(S)-(2-[(6-Chloro-2-(2-fluoro-phenyl)-pyrimidine-4-carbonyl)-amino]-3-methyl-butyryl}-piperazine-1-carboxylic acid butyl ester This compound was prepared using a method analogous to that of Example 1, step 1.7, intermediate 47.1 replacing intermediate A and intermediate 11.2 replacing intermediate 1.6. The compound was purified by CC (Hept/EA 3/1 to EA).
LC-MS: $t_R$=1.14 min; [M+H]$^+$: 515.99.

47.3. (1α,5α,6β)-3-[6-[(S)-1-(4-Butoxycarbonyl-piperazine-1-carbonyl)-2-methyl-propylcarbamoyl]-2-(2-fluoro-phenyl)-pyrimidin-4-yl]-3-aza-bicyclo[3.1.0]hexane-6-carboxylic acid ethyl ester This compound was prepared using a method analogous to that of Example 1, step 1.8, intermediate 47.2 replacing intermediate 1.7 and intermediate 2.2 replacing intermediate 1.2. The compound was purified by CC (Hept/EA 1/1 to EA).
LC-MS: $t_R$=1.14 min; [M+H]$^+$: 638.85.

47.4. (1α,5α,6β)-3-[6-[(S)-1-(4-Butoxycarbonyl-piperazine-1-carbonyl)-2-methyl-propylcarbamoyl]-2-(2-fluoro-phenyl)-pyrimidin-4-yl]-3-aza-bicyclo[3.1.0]hexane-6-carboxylic acid This compound was prepared using a method analogous to that of Example 28, step 28.5, intermediate 47.3 replacing intermediate 28.4.
LC-MS: $t_R$=1.05 min; [M+H]$^+$: 610.97.

Example 48

(1α,5α,6β)-3-{6-[(S)-1-(4-Butoxycarbonyl-piperazine-1-carbonyl)-2-cyano-ethylcarbamoyl]-2-phenyl-pyrimidin-4-yl}-3-aza-bicyclo[3.1.0]hexane-6-carboxylic acid

48.1 4-((S)-2-tert-Butoxycarbonylamino-3-cyano-propionyl)-piperazine-1-carboxylic acid butyl ester This compound was prepared using a method analogous to that of Example 1, step 1.5, Boc-beta-cyano-Ala-OH replacing Cbz-(L)Glu(OtBu)-OH. The compound was however not purified and used as crude.
LC-MS: $t_R$=0.96 min; [M+H]$^+$: 382.96.

48.2 4-((S)-2-Amino-3-cyano-propionyl)-piperazine-1-carboxylic acid butyl ester This compound was prepared using a method analogous to that of Example 33, step 33.2, intermediate 48.1 replacing intermediate 33.1.
LC-MS: $t_R$=0.67 min; [M+H]$^+$: 283.15.

48.3 4-{(S)-2-[(6-Chloro-2-phenyl-pyrimidine-4-carbonyl)-amino]-3-cyano-propionyl}-piperazine-1-carboxylic acid butyl ester This compound was prepared using a method analogous to that of Example 1, step 1.7, intermediate 48.2 replacing intermediate 1.6. The compound was purified by CC (Hept/EA 4/1).
LC-MS: $t_R$=1.08 min; [M+H]$^+$: 498.97.

48.4 (1α,5α,6β)-3-{6-[(S)-1-(4-Butoxycarbonyl-piperazine-1-carbonyl)-2-cyano-ethylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 48.3 replacing intermediate 1.7 and intermediate 2.2 replacing intermediate 1.2.
LC-MS: $t_R$=1.10 min; [M+H]$^+$: 617.98.

48.5 (1α,5α,6β)-3-{6-[(S)-1-(4-Butoxycarbonyl-piperazine-1-carbonyl)-2-cyano-ethylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 48.4 replacing intermediate 1.8.
LC-MS: $t_R$=1.01 min; [M+H]$^+$: 590.05.

Example 49

(1α,5α,6β)-3-{6-[(S)-1-(4-Butoxycarbonyl-piperazine-1-carbonyl)-3-(1H-tetrazol-5-yl)-propylcarbamoyl]-2-phenyl-pyrimidin-4-yl}-3-aza-bicyclo[3.1.0]hexane-6-carboxylic acid

49.1 (1α,5α,6β)-3-{6-[(S)-1-(4-Butoxycarbonyl-piperazine-1-carbonyl)-3-(1H-tetrazol-5-yl)-propylcarbamoyl]-2-phenyl-pyrimidin-4-yl}-3-aza-bicyclo[3.1.0]hexane-6-carboxylic acid ethyl ester To intermediate 48.4 (24 mg) was added trimethylsilylazide (7 mg) followed by TBAF 3H$_2$O (7 mg). The reaction mixture was stirred overnight at 80° C. EA was added and the mixture was washed with water, dried (MgSO$_4$) and evaporated off to obtain 22 mg of the desired compound as slightly brown oil.
LC-MS: $t_R$=1.05 min; [M+H]$^+$: 675.18.

49.2 (1α,5α,6β)-3-{6-[(S)-1-(4-Butoxycarbonyl-piperazine-1-carbonyl)-3-(1H-tetrazol-5-yl)-propylcarbamoyl]-2-phenyl-pyrimidin-4-yl}-3-aza-bicyclo[3.1.0]hexane-6-carboxylic acid This compound was prepared using a method analogous to that of Example 1, step 1.9, intermediate 49.1 replacing intermediate 1.8.
LC-MS: $t_R$=0.97 min; [M+H]$^+$: 647.14.

Example 50

(1α,5α,6α)-3-{6-[(R)-2-(4-Butoxycarbonyl-piperazin-1-yl)-1-(diethoxy-phosphorylmethyl)-2-oxo-ethylcarbamoyl]-2-phenyl-pyrimidin-4-yl}-3-aza-bicyclo[3.1.0]hexane-6-carboxylic acid ethyl ester

50.1. (R)-2-tert-Butoxycarbonylamino-3-(diethoxy-phosphoryl)-propionic acid methyl ester Boc-3-iodo-L-Ala-OMe (9.4 g) was dissolved in triethyl phosphite (100 mL). The mixture was heated at 130° C. overnight and evaporated to dryness to give a yellow oil (8.37 g). The compound was used in the next step without further purification.
LC-MS: $t_R$=0.85 min; [M+H]$^+$: 340.09

50.2. (R)-2-tert-Butoxycarbonylamino-3-(diethoxy-phosphoryl)-propionic acid

An aq. solution of lithium hydroxide hydrate (2.07 g in 5 mL) was added to a solution of intermediate 50.1 (8.37 g) in THF (99 mL). The reaction mixture was stirred at RT overnight and DCM and an aq. HCl solution (1M, 60 mL) was added. The phases were separated and the aq. phase was extracted with DCM (3×). The org. phases were combined, dried ($Na_2SO_4$) and evaporated off to give 5.8 g of the desired product as a white powder.
LC-MS: $t_R$=0.77 min; $[M+H]^+$: 326.13.

50.3. 4-[(R)-2-tert-Butoxycarbonylamino-3-(diethoxy-phosphoryl)-propionyl]-piperazine-1-carboxylic acid butyl ester To a solution of intermediate 50.2 (7.37 g) in DCM (95 mL), THF (24 mL) and DIPEA (16.3 mL) were added HOBT (3.83 g) and EDC-HCl (4.78 g), and the reaction mixture was stirred at RT for 10 min. Subsequently, piperazine-1-carboxylic acid butyl ester (5.31 g) was added and the mixture was stirred at RT for 2.5 h. The reaction mixture was diluted with DCM, the org. phase washed with sat. aq. $NaHCO_3$ and the aq. phase re-extracted with DCM. The combined org. phases were washed with brine, dried over $Na_2SO_4$, and concentrated to dryness. Purification by CC (EtOAc/MeOH 1:0 to 9:1) gave 7.66 g of the desired product.
LC-MS: $t_R$=0.94 min; $[M+H]^+$: 494.00

50.4 4-[(R)-2-Amino-3-(diethoxy-phosphoryl)-propionyl]-piperazine-1-carboxylic acid butyl ester hydrochloride salt To a solution of intermediate 50.3 (7.66 g) in EtOAc (7.75 mL) was added HCl (15.5 mL, 4M in dioxane) and the reaction mixture stirred at RT until reaction completion. The mixture was concentrated to dryness and the residue dried overnight to give 6.59 g of the desired product, which was used without further purification.
LC-MS: $t_R$=0.73 min; $[M+H]^+$: 394.43

50.5. 4-[(R)-2-[(6-Chloro-2-phenyl-pyrimidine-4-carbonyl)-amino]-3-(diethoxy-phosphoryl)-propionyl]-piperazine-1-carboxylic acid butyl ester To a solution of intermediate A (477 mg) in DCM (30 mL) was added intermediate 50.4 (800 mg) followed by DIPEA (0.42 mL) and PyBOP (1.16 g), and the reaction mixture was stirred at RT for 1 h. The reaction mixture was diluted with DCM, washed with 1N $NaHSO_4$ (1×), aq. sat. $NaHCO_3$ (1×) and brine (1×). Each aq. layer was afterwards extracted with DCM (2×). The combined org. layers were dried over $MgSO_4$ and evaporated to dryness. The compound was purified by CC (DCM/MeOH 99:1 to 95:5) to give 678 mg of the desired product.
LC-MS: $t_R$=1.14 min; $[M+H]^+$: 610.73.

50.6. (1α,5α,6α)-3-{6-[(R)-2-(4-Butoxycarbonyl-piperazin-1-yl)-1-(diethoxy-phosphoryl-methyl)-2-oxo-ethylcarbamoyl]-2-phenyl-pyrimidin-4-yl}-3-aza-bicyclo[3.1.0]hexane-6-carboxylic acid ethyl ester This compound was prepared using a method analogous to that of Example 1, step 1.8, intermediate 50.5 replacing intermediate 1.7. The compound was purified by CC (DCM/MeOH 99:1 to 96:4)
LC-MS: $t_R$=1.17 min; $[M+H]^+$: 729.83. .

Example 51

(1α,5α,6α)-3-{6-[(R)-2-(4-Butoxycarbonyl-piperazin-1-yl)-2-oxo-1-phosphonomethyl-ethylcarbamoyl]-2-phenyl-pyrimidin-4-yl}-3-aza-bicyclo[3.1.0]hexane-6-carboxylic acid ethyl ester A suspension of intermediate 50.6 (203 mg) in 4M HCl in dioxane (3.5 mL) was stirred at 45° C. for 1 d. The reaction mixture was diluted with toluene and evaporated to dryness. Purification of 45 mg crude material by prep HPLC (VI) gave 28 mg of the desired product.
LC-MS: $t_R$=1.00 min; $[M+H]^+$: 672.90.

Example 52

(1α,5α,6α)-3-{6-[(R)-1-(Bis-acetoxymethoxy-phosphorylmethyl)-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid ethyl ester A brown solution of Example 51 (50 mg) and $Et_3N$ (0.041 mL) in NMP (0.6 mL) was stirred 20 min at RT. Then bromomethyl acetate (0.092 mL) was added followed by NaI (13 mg). The resulting suspension was stirred for 22 h at 45° C. The reaction mixture was diluted with toluene and washed with 5× water. Each. aq. layer was afterwards extracted with toluene (2×). The combined org. layers were dried over $MgSO_4$ and evaporated to dryness. Preparative TLC (DCM/MeOH 97:3) gave 9 mg of the desired product.
LC-MS: $t_R$=1.16 min; $[M+H]^+$: 817.38.

Example 53

N,N'-Bis-((S)-1-Ethoxycarbonylethyl)-(R)-2-[(4-[(1α,5α,6α)-6-ethoxycarbonyl-3-aza-bicyclo[3.1.0]hex-3-yl]-2-phenyl-pyrimidin-6-carbonyl)-amino]-3-oxo-3-(4-butoxy-carbonyl-piperazin-1-yl)-propyl-phosphonic acid diamide A mixture of Example 51 (100 mg), HCl H-Ala-OEt (68 mg) and $NEt_3$ (0.124 mL) in abs. pyridine (1 mL) was heated to 60° C. for 10 min. Then, a mixture of 2,2'-dipyridyl disulfide (114 mg) and $PPh_3$ (136 mg) in abs. pyridine (0.5 mL) prestirred at RT for 5 min was added, and the reaction mixture heated at 60° C. for 3 d. The reaction mixture was diluted with brine 10 ml and extracted with DCM (3×). The combined organic layers were dried over $MgSO_4$ and concentrated to dryness. The residue was purified by CC (Heptan/EA 1:1 to 0:1) to give 14 mg of the desired product.
LC-MS: $t_R$=0.99 mM; $[M+H]^+$: 871.39.

Example 54

(1α,5α,6α)-3-{6-[(R)-1-(Bis-ethoxycarbonyloxymethoxy-phosphorylmethyl)-2-(4-butoxycarbonyl-piperazin-1-yl)-2-oxo-ethylcarbamoyl]-2-phenyl-pyrimidin-4-yl}-3-aza-bicyclo[3.1.0]hexane-6-carboxylic acid ethyl ester This compound was prepared using a method analogous to that of Example 52, chloromethyl ethyl carbonate (prepared as described in WO2004092189) replacing bromomethyl acetate.
LC-MS: $t_R$=1.22 mM; $[M+H]^+$: 877.37.

Biological Tests
P2Y$_{12}$ Receptor Binding Assay
Procedure
Chinese Hamster Ovary (CHO) cells with recombinant expression of the human P2Y$_{12}$ receptor were cultured in 24 well cell-culture plates. Cells were washed three times with binding buffer (50 mM Tris pH 7.4, 100 mM NaCl, 1 mM EDTA, 0.5% BSA). The cells were then incubated with 0.5 ml per well binding buffer containing tritium-labeled 2-methyl-thio-adenosine 5'-diphosphate (2-methyl-S-ADP) (between 100,000 and 300,000 dpm per well) and various concentrations of test compounds. After incubation at RT for 2 hours, cells were washed three times with binding buffer. Then, cells were solubilized by addition of 0.5 ml solubilization buffer (SDS, NaOH, EDTA). The content of each well was then transferred into beta-counter vials and 2.0 ml of Ultima Gold Scintillation liquid was added. After quantification of the cell-associated signal, extent of inhibition was calculated relative to maximal possible inhibition demonstrated by addition of excess of cold 2-methyl-S-ADP.
Results Obtained for the Compounds of Formula I
The following results could be obtained for the Example compounds of formula I using the procedure described above for the P2Y$_{12}$ receptor binding assay:

| Example No. | IC$_{50}$ at P2Y$_{12}$ receptor binding assay (nM) |
| --- | --- |
| 1 | 10 |
| 2 | 3.7 |
| 3 | 8.7 |
| 4 | 15 |
| 5 | 6.2 |
| 6 | 7.3 |
| 7 | 7.5 |
| 8 | 7.0 |
| 9 | 8.0 |
| 10 | 6.6 |
| 11 | 14 |
| 12 | 70 |
| 13 | 96 |
| 14 | 60 |
| 15 | 15 |
| 16 | 34 |
| 17 | 13 |
| 18 | 75 |
| 19 | 12 |
| 20 | 20 |
| 21 | 10 |
| 22 | 38 |
| 23 | 266 |
| 24 | 13 |
| 25 | 13 |
| 26 | 59 |
| 27 | 151 |
| 28 | 7 |
| 29 | 18 |
| 30 | 250 |
| 31 | 53 |
| 32 | 477 |
| 33 | 68 |
| 34 | 229 |
| 35 | 51 |
| 36 | 96 |
| 37 | 123 |
| 38 | 136 |
| 39 | 124 |
| 40 | 143 |
| 41 | 22 |
| 42 | 50 |
| 43 | 330 |
| 44 | 903 |
| 45 | 255 |
| 46 | 961 |
| 47 | 12 |
| 48 | 74 |
| 49 | <3.2 |
| 50 | 383 |
| 51 | 2.5 |
| 52 | 4 |
| 53 | 110 |
| 54 | 15 |

The invention claimed is:
1. A compound of formula I

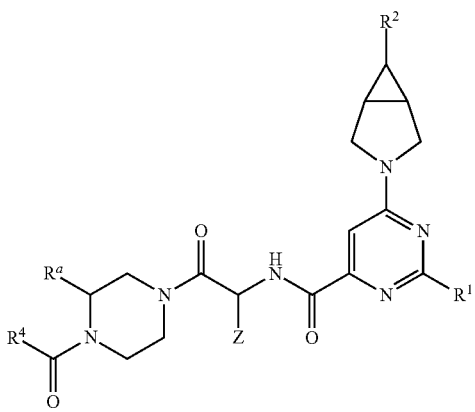

wherein
R$^1$ represents phenyl which is unsubstituted or mono-, di- or tri-substituted, wherein the substituents are independently selected from the group consisting of halogen, (C$_1$-C$_4$)alkyl and (C$_1$-C$_3$)fluoroalkyl;
Z represents hydrogen, (C$_1$-C$_4$)alkyl, cyclopropyl, cyclopropylmethyl, hydroxy-(C$_1$-C$_3$)alkyl, carboxy-(C$_1$-C$_3$) alkyl, cyano-(C$_1$-C$_3$)alkyl, P(O)(R$^6$)$_2$—(C$_1$-C$_3$)alkyl, 1H-tetrazol-5-yl-(C$_1$-C$_3$)alkyl or benzyl;
R$^2$ represents cyano, —COOH, —CONH$_2$, —COOR$^3$, hydroxy-(C$_1$-C$_3$)alkyl, (C$_1$-C$_2$)alkoxy-(C$_1$-C$_2$)alkyl, carboxy-(C$_1$-C$_3$)alkyl, 1H-tetrazol-5-yl or —NHR$^5$;
with the proviso that, if R$^2$ represents —COOR$^3$, Z represents carboxy-(C$_1$-C$_3$)alkyl or P(O)(R$^6$)$_2$—(C$_1$-C$_3$) alkyl;
R$^a$ represents hydrogen or methyl;
R$^3$ represents (C$_1$-C$_4$)alkyl;
R$^4$ represents (C$_1$-C$_6$)alkoxy or benzyloxy;
R$^5$ represents hydrogen or tert-butoxycarbonyl;
R$^6$ represents hydroxy, (C$_1$-C$_4$)alkoxy, R$^7$—OCH$_2$O— or R$^8$—(C$_1$-C$_4$)alkyl-NH—;
R$^7$ represents (C$_1$-C$_4$)alkylcarbonyl or (C$_1$-C$_4$)alkoxycarbonyl; and
R$^8$ represents (C$_1$-C$_4$)alkoxycarbonyl;
or a salt of such a compound.
2. The compound of formula I according to claim 1, wherein
R$^1$ represents phenyl which is unsubstituted or mono-substituted with fluorine, methyl or trifluoromethyl;
Z represents hydrogen, (C$_1$-C$_4$)alkyl, cyclopropyl, 1-hydroxy-ethyl, 2-carboxy-ethyl, cyano-methyl, or 2-(1H-tetrazol-5-yl)-ethyl;

R² represents cyano, —COOH, —CONH₂, hydroxy-methyl, methoxy-methyl, carboxy-methyl, 2-carboxy-ethyl, 1H-tetrazol-5-yl or —NHR⁵;
Rᵃ represents hydrogen;
R⁴ represents (C₁-C₆)alkoxy; and
R⁵ represents hydrogen or tert-butoxycarbonyl;
or a salt of such a compound.

3. The compound of formula I according to claim 1, wherein R¹ represents phenyl which is unsubstituted or mono-substituted with halogen, (C₁-C₂)alkyl or trifluoromethyl;
or a salt of such a compound.

4. The compound of formula I according to claim 1, wherein Z represents hydrogen, (C₁-C₄)alkyl, cyclopropyl, cyclopropylmethyl, hydroxy-(C₁-C₂)alkyl, carboxy-(C₁-C₂)alkyl, cyano-(C₁-C₂)alkyl, P(O)(R⁶)₂—(C₁-C₂)alkyl, 1H-tetrazol-5-yl-(C₁-C₂)alkyl or benzyl;
or a salt of such a compound.

5. The compound of formula I according to claim 1, wherein Z represents P(O)(R⁶)₂—(C₁-C₂)alkyl;
or a salt of such a compound.

6. The compound of formula I according to claim 1, wherein R² represents cyano, —COOH, —CONH₂, hydroxy-methyl, methoxy-methyl, carboxy-methyl, 2-carboxy-ethyl, 1H-tetrazol-5-yl or —NHR⁵;
or a salt of such a compound.

7. The compound of formula I according to claim 1, wherein Rᵃ represents hydrogen;
or a salt of such a compound.

8. The compound of formula I according to claim 1, wherein R⁴ represents (C₁-C₆)alkoxy;
or a salt of such a compound.

9. The compound of formula I according to claim 5, wherein R⁶ represents hydroxy, R⁷—OCH₂O— or R⁸—(C₁-C₄)alkyl-NH—;
or a salt of such a compound.

10. The compound of formula I according to claim 9, wherein R⁷ represents (C₁-C₂)alkylcarbonyl or (C₁-C₂)alkoxycarbonyl;
or a salt of such a compound.

11. The compound of formula I according to claim 1, which is selected from the group consisting of:
(1α,5α,6α)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid;
(1α,5α,6β)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid;
(1α,5α,6α)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid ethyl ester;
(1α,5α,6β)-3-{6-[(S)-1-(4-Butoxycarbonyl-piperazine-1-carbonyl)-3-carboxy-propylcarbamoyl]-2-phenyl-pyrimidin-4-yl}-3-aza-bicyclo[3.1.0]hexane-6-carboxylic acid ethyl ester;
4-((S)-2-{[6-((1α,5α,6α)-6-tert-Butoxycarbonylamino-3-aza-bicyclo[3.1.0]hex-3-yl)-2-phenyl-pyrimidine-4-carbonyl]-amino}-4-carboxy-butyryl)-piperazine-1-carboxylic acid butyl ester;
4-((S)-2-{[6-((1α,5α,6β)-6-tert-Butoxycarbonylamino-3-aza-bicyclo[3.1.0]hex-3-yl)-2-phenyl-pyrimidine-4-carbonyl]-amino}-4-carboxy-butyryl)-piperazine-1-carboxylic acid butyl ester;
4-((S)-2-{[6-((1α,5α,6α)-6-Amino-3-aza-bicyclo[3.1.0]hex-3-yl)-2-phenyl-pyrimidine-4-carbonyl]-amino}-4-carboxy-butyryl)-piperazine-1-carboxylic acid butyl ester;
4-((S)-2-{[6-((1α,5α,6β)-6-Amino-3-aza-bicyclo[3.1.0]hex-3-yl)-2-phenyl-pyrimidine-4-carbonyl]-amino}-4-carboxy-butyryl)-piperazine-1-carboxylic acid butyl ester;
4-((S)-4-Carboxy-2-{[6-((1α,5α,6α)-6-hydroxymethyl-3-aza-bicyclo[3.1.0]hex-3-yl)-2-phenyl-pyrimidine-4-carbonyl]-amino}-butyryl)-piperazine-1-carboxylic acid butyl ester;
4-((S)-4-Carboxy-2-{[6-((1α,5α,6α)-6-methoxymethyl-3-aza-bicyclo[3.1.0]hex-3-yl)-2-phenyl-pyrimidine-4-carbonyl]-amino}-butyryl)-piperazine-1-carboxylic acid butyl ester;
(1α,5α,6β)-3-{6-[(S)-1-(4-Butoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid;
(1α,5α,6α)-3-{6-[(S)-1-(4-Butoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid;
(1α,5α,6β)-3-{6-[(S)-1-(4-Ethoxycarbonyl-piperazine-1-carbonyl)-2-methyl-propylcarbamoyl]-2-phenyl-pyrimidin-4-yl}-3-aza-bicyclo[3.1.0]hexane-6-carboxylic acid;
(1α,5α,6β)-3-{6-[(S)-2-Methyl-1-(4-propoxycarbonyl-piperazine-1-carbonyl)-propylcarbamoyl]-2-phenyl-pyrimidin-4-yl}-3-aza-bicyclo[3.1.0]hexane-6-carboxylic acid;
(1α,5α,6β)-3-{6-[(S)-2-Methyl-1-(4-pentyloxycarbonyl-piperazine-1-carbonyl)-propylcarbamoyl]-2-phenyl-pyrimidin-4-yl}-3-aza-bicyclo[3.1.0]hexane-6-carboxylic acid;
(1α,5α,6β)-3-{6-[(S)-1-(4-Hexyloxycarbonyl-piperazine-1-carbonyl)-2-methyl-propylcarbamoyl]-2-phenyl-pyrimidin-4-yl}-3-aza-bicyclo[3.1.0]hexane-6-carboxylic acid;
4-((S)-2-{[6-((1α,5α,6α)-6-Carbamoyl-3-aza-bicyclo[3.1.0]hex-3-yl)-2-phenyl-pyrimidine-4-carbonyl]-amino}-3-methyl-butyryl)-piperazine-1-carboxylic acid butyl ester;
4-((S)-2-{[6-((1α,5α,6α)-6-Cyano-3-aza-bicyclo[3.1.0]hex-3-yl)-2-phenyl-pyrimidine-4-carbonyl]-amino}-3-methyl-butyryl)-piperazine-1-carboxylic acid butyl ester;
4-[(S)-3-Methyl-2-({2-phenyl-6-[(1α,5α,6α)-6-(1H-tetrazol-5-yl)-3-aza-bicyclo[3.1.0]hex-3-yl]-pyrimidine-4-carbonyl}-amino)-butyryl]-piperazine-1-carboxylic acid butyl ester;
4-((S)-2-{[6-((1α,5α,6β)-6-Carbamoyl-3-aza-bicyclo[3.1.0]hex-3-yl)-2-phenyl-pyrimidine-4-carbonyl]-amino}-3-methyl-butyryl)-piperazine-1-carboxylic acid butyl ester;
4-((S)-2-{[6-((1α,5α,6β)-6-Cyano-3-aza-bicyclo[3.1.0]hex-3-yl)-2-phenyl-pyrimidine-4-carbonyl]-amino}-3-methyl-butyryl)-piperazine-1-carboxylic acid butyl ester;
4-[(S)-3-Methyl-2-({2-phenyl-6-[(1α,5α,6β)-6-(1H-tetrazol-5-yl)-3-aza-bicyclo[3.1.0]hex-3-yl]-pyrimidine-4-carbonyl}-amino)-butyryl]-piperazine-1-carboxylic acid butyl ester;

4-((S)-2-{[6-((1α,5α,6β)-6-Amino-3-aza-bicyclo[3.1.0]
hex-3-yl)-2-phenyl-pyrimidine-4-carbonyl]-amino}-3-
methyl-butyryl)-piperazine-1-carboxylic acid butyl
ester;
4-((S)-2-{[6-((1α,5α,6α)-6-Carboxymethyl-3-aza-bicy-
clo[3.1.0]hex-3-yl)-2-phenyl-pyrimidine-4-carbonyl]-
amino}-3-methyl-butyryl)-piperazine-1-carboxylic
acid butyl ester;
4-((S)-2-{[6-((1α,5α,6β)-6-Carboxymethyl-3-aza-bicy-
clo[3.1.0]hex-3-yl)-2-phenyl-pyrimidine-4-carbonyl]-
amino}-3-methyl-butyryl)-piperazine-1-carboxylic
acid butyl ester;
4-[(S)-2-({6-[(1α,5α,6β)-6-(2-Carboxy-ethyl)-3-aza-bi-
cyclo[3.1.0]hex-3-yl]-2-phenyl-pyrimidine-4-carbo-
nyl}-amino)-3-methyl-butyryl]-piperazine-1-carboxy-
lic acid butyl ester;
4-[(S)-2-({6-[(1α,5α,6α)-6-(2-Carboxy-ethyl)-3-aza-bi-
cyclo[3.1.0]hex-3-yl]-2-phenyl-pyrimidine-4-carbo-
nyl}-amino)-3-methyl-butyryl]-piperazine-1-carboxy-
lic acid butyl ester;
(1α,5α,6β)-3-[6-[(S)-1-(4-Butoxycarbonyl-piperazine-1-
carbonyl)-2-methyl-propylcarbamoyl]-2-(4-fluoro-
phenyl)-pyrimidin-4-yl]-3-aza-bicyclo[3.1.0]hexane-6-
carboxylic acid;
(1α,5α,6β)-3-{6-[(S)-1-(4-Butoxycarbonyl-piperazine-1-
carbonyl)-2-methyl-propylcarbamoyl]-2-p-tolyl-pyri-
midin-4-yl}-3-aza-bicyclo[3.1.0]hexane-6-carboxylic
acid;
(1α,5α,6β)-3-[6-[(S)-1-(4-Butoxycarbonyl-piperazine-1-
carbonyl)-2-methyl-propylcarbamoyl]-2-(3-trifluo-
romethyl-phenyl)-pyrimidin-4-yl]-3-aza-bicyclo[3.1.0]
hexane-6-carboxylic acid;
(1α,5α,6β)-3-{6-[(S)-1-((R)-4-Butoxycarbonyl-3-me-
thyl-piperazine-1-carbonyl)-2-methyl-propylcarbam-
oyl]-2-phenyl-pyrimidin-4-yl}-3-aza-bicyclo[3.1.0]
hexane-6-carboxylic acid;
(1α,5α,6β)-3-{6-[(S)-1-((R)-4-Benzyloxycarbonyl-3-
methyl-piperazine-1-carbonyl)-2-methyl-propylcar-
bamoyl]-2-phenyl-pyrimidin-4-yl}-3-aza-bicyclo
[3.1.0]hexane-6-carboxylic acid;
(1α,5α,6β)-3-{6-[2-(4-Butoxycarbonyl-piperazin-1-yl)-
2-oxo-ethylcarbamoyl]-2-phenyl-pyrimidin-4-yl}-3-
aza-bicyclo[3.1.0]hexane-6-carboxylic acid;
(1α,5α,6α)-3-{6-[(S)-2-(4-Butoxycarbonyl-piperazin-1-
yl)-1-methyl-2-oxo-ethylcarbamoyl]-2-phenyl-pyrimi-
din-4-yl}-3-aza-bicyclo[3.1.0]hexane-6-carboxylic
acid;
(1α,5α,6β)-3-{6-[(S)-2-(4-Butoxycarbonyl-piperazin-1-
yl)-1-methyl-2-oxo-ethylcarbamoyl]-2-phenyl-pyrimi-
din-4-yl}-3-aza-bicyclo[3.1.0]hexane-6-carboxylic
acid;
(1α,5α,6β)-3-{6-[(S)-1-(4-Butoxycarbonyl-piperazine-1-
carbonyl)-propylcarbamoyl]-2-phenyl-pyrimidin-4-
yl}-3-aza-bicyclo[3.1.0]hexane-6-carboxylic acid;
(1α,5α,6β)-3-{6-[(S)-1-(4-Butoxycarbonyl-piperazine-1-
carbonyl)-butylcarbamoyl]-2-phenyl-pyrimidin-4-yl}-
3-aza-bicyclo[3.1.0]hexane-6-carboxylic acid;
(1α,5α,6β)-3-{6-[(S)-1-(4-Butoxycarbonyl-piperazine-1-
carbonyl)-pentylcarbamoyl]-2-phenyl-pyrimidin-4-
yl}-3-aza-bicyclo[3.1.0]hexane-6-carboxylic acid;
(1α,5α,6β)-3-{6-[(S)-1-(4-Butoxycarbonyl-piperazine-1-
carbonyl)-3-methyl-butylcarbamoyl]-2-phenyl-pyrimi-
din-4-yl}-3-aza-bicyclo[3.1.0]hexane-6-carboxylic
acid;
(1α,5α,6β)-3-{6-[(S)-2-(4-Butoxycarbonyl-piperazin-1-
yl)-1-cyclopropylmethyl-2-oxo-ethylcarbamoyl]-2-
phenyl-pyrimidin-4-yl}-3-aza-bicyclo[3.1.0]hexane-6-
carboxylic acid;
(1α,5α,6β)-3-{6-[(S)-2-(4-Butoxycarbonyl-piperazin-1-
yl)-1-cyclopropyl-2-oxo-ethylcarbamoyl]-2-phenyl-
pyrimidin-4-yl}-3-aza-bicyclo[3.1.0]hexane-6-car-
boxylic acid;
(1α,5α,6β)-3-{6-[(1S,2R)-1-(4-Butoxycarbonyl-pipera-
zine-1-carbonyl)-2-hydroxy-propylcarbamoyl]-2-phe-
nyl-pyrimidin-4-yl}-3-aza-bicyclo[3.1.0]hexane-6-car-
boxylic acid;
(1α,5α,6β)-3-{6-[(S)-1-(4-Butoxycarbonyl-piperazine-1-
carbonyl)-2,2-dimethyl-propylcarbamoyl]-2-phenyl-
pyrimidin-4-yl}-3-aza-bicyclo[3.1.0]hexane-6-car-
boxylic acid;
(1α,5α,6α)-3-{6-[(S)-1-(4-Butoxycarbonyl-piperazine-
1-carbonyl)-2,2-dimethyl-propylcarbamoyl]-2-phenyl-
pyrimidin-4-yl}-3-aza-bicyclo[3.1.0]hexane-6-car-
boxylic acid;
(1α,5α,6β)-3-{6-[(S)-1-Benzyl-2-(4-butoxycarbonyl-
piperazin-1-yl)-2-oxo-ethylcarbamoyl]-2-phenyl-pyri-
midin-4-yl}-3-aza-bicyclo[3.1.0]hexane-6-carboxylic
acid;
(1α,5α,6α)-3-{6-[(S)-1-Benzyl-2-(4-butoxycarbonyl-
piperazin-1-yl)-2-oxo-ethylcarbamoyl]-2-phenyl-pyri-
midin-4-yl}-3-aza-bicyclo[3.1.0]hexane-6-carboxylic
acid;
(1α,5α,6β)-3-[6-[(S)-1-(4-Butoxycarbonyl-piperazine-1-
carbonyl)-2-methyl-propylcarbamoyl]-2-(2-fluoro-
phenyl)-pyrimidin-4-yl]-3-aza-bicyclo[3.1.0]hexane-6-
carboxylic acid;
(1α,5α,6β)-3-{6-[(S)-1-(4-Butoxycarbonyl-piperazine-1-
carbonyl)-2-cyano-ethylcarbamoyl]-2-phenyl-pyrimi-
din-4-yl}-3-aza-bicyclo[3.1.0]hexane-6-carboxylic
acid;
(1α,5α,6β)-3-{6-[(S)-1-(4-Butoxycarbonyl-piperazine-1-
carbonyl)-3-(1H-tetrazol-5-yl)-propylcarbamoyl]-2-
phenyl-pyrimidin-4-yl}-3-aza-bicyclo[3.1.0]hexane-6-
carboxylic acid;
(1α,5α,6α)-3-{6-[(R)-2-(4-Butoxycarbonyl-piperazin-1-
yl)-1-(diethoxy-phosphorylmethyl)-2-oxo-ethylcar-
bamoyl]-2-phenyl-pyrimidin-4-yl}-3-aza-bicyclo
[3.1.0]hexane-6-carboxylic acid ethyl ester;
(1α,5α,6α)-3-{6-[(R)-2-(4-Butoxycarbonyl-piperazin-1-
yl)-2-oxo-1-phosphonomethyl-ethylcarbamoyl]-2-phe-
nyl-pyrimidin-4-yl}-3-aza-bicyclo[3.1.0]hexane-6-car-
boxylic acid ethyl ester;
(1α,5α,6α)-3-{6-[(R)-1-(Bis-(acetoxymethoxy)-phos-
phorylmethyl)-2-(4-butoxycarbonyl-piperazin-1-yl)-2-
oxo-ethylcarbamoyl]-2-phenyl-pyrimidin-4-yl}-3-aza-
bicyclo[3.1.0]hexane-6-carboxylic acid ethyl ester;
N,N'-Bis-((S)-1-Ethoxycarbonylethyl)-(R)-2-[(4-[(1α,
5α,6α)-6-ethoxycarbonyl-3-aza-bicyclo[3.1.0]hex-3-
yl]-2-phenyl-pyrimidin-6-carbonyl)-amino]-3-oxo-3-
(4-butoxy-carbonyl-piperazin-1-yl)-propyl-phosphonic
acid diamide; and
(1α,5α,6α)-3-{6-[(R)-1-(Bis-(ethoxycarbony-
loxymethoxy)-phosphorylmethyl)-2-(4-butoxycarbo-
nyl-piperazin-1-yl)-2-oxo-ethylcarbamoyl]-2-phenyl-
pyrimidin-4-yl}-3-aza-bicyclo[3.1.0]hexane-6-
carboxylic acid ethyl ester;
or a salt of such a compound.

12. A pharmaceutical composition containing at least one compound of formula I as defined in claim 1, or a pharmaceutically acceptable salt thereof, and one or more pharmaceutically acceptable carriers, diluents or excipients.

13. A method for the treatment of myocardial infarction, arterial thrombosis, transient ischaemic attacks, peripheral vascular disease and stable and unstable angina comprising the administration to a patient in need thereof an effective amount of a compound of formula I according to claim 1, in free or pharmaceutically acceptable salt of such a compound.

14. A method for the treatment of myocardial infarction, arterial thrombosis, transient ischaemic attacks, peripheral vascular disease and stable and unstable angina comprising the administration to a patient in need thereof an effective amount of a compound according to claim 11, in free or pharmaceutically acceptable salt of such a compound.

15. A method for the treatment of thrombosis comprising the administration to a patient in need thereof an effective amount of a compound of formula I according to claim 1, in free or pharmaceutically acceptable salt of such a compound.

16. A method for the treatment of thrombosis comprising the administration to a patient in need thereof an effective amount of a compound according to claim 11, in free or pharmaceutically acceptable salt of such a compound.

* * * * *